US008865748B2

(12) United States Patent
Shalwitz et al.

(10) Patent No.: US 8,865,748 B2
(45) Date of Patent: Oct. 21, 2014

(54) COMPOUNDS AND COMPOSITIONS FOR STABILIZING HYPOXIA INDUCIBLE FACTOR-2 ALPHA AS A METHOD FOR TREATING CANCER

(75) Inventors: Robert Shalwitz, Bexley, OH (US); Joseph H. Gardner, Cincinnati, OH (US)

(73) Assignee: Akebia Therapeutics Inc., Cambridge, MA (US)

( * ) Notice: Subject to any disclaimer, the term of this patent is extended or adjusted under 35 U.S.C. 154(b) by 0 days.

(21) Appl. No.: 13/489,400

(22) Filed: Jun. 5, 2012

(65) Prior Publication Data

US 2012/0316204 A1  Dec. 13, 2012

Related U.S. Application Data

(60) Provisional application No. 61/493,534, filed on Jun. 6, 2011.

(51) Int. Cl.
*A61K 31/44* (2006.01)
*C07D 213/81* (2006.01)

(52) U.S. Cl.
CPC .................... *C07D 213/81* (2013.01)
USPC ........................................................ 514/350

(58) Field of Classification Search
CPC ...................................................... C07D 213/82
USPC ...................................................... 514/350
See application file for complete search history.

(56) References Cited

U.S. PATENT DOCUMENTS

| 4,016,287 | A | 4/1977 | Eberhardt et al. |
| 5,397,799 | A | 3/1995 | Kress et al. |
| 5,405,613 | A | 4/1995 | Rowland et al. |
| 5,620,995 | A | 4/1997 | Weidemann et al. |
| 5,658,933 | A | 8/1997 | Weidemann et al. |
| 6,020,350 | A | 2/2000 | Weidemann et al. |
| 6,159,379 | A | 12/2000 | Means et al. |
| 6,420,427 | B1 | 7/2002 | Takahashi et al. |
| 7,811,595 | B2 | 10/2010 | Kawamoto et al. |
| 8,323,671 | B2 | 12/2012 | Wu et al. |
| 8,343,952 | B2 | 1/2013 | Wu et al. |
| 2004/0235082 | A1 | 11/2004 | Fourney et al. |
| 2004/0254215 | A1 | 12/2004 | Arend et al. |
| 2006/0142389 | A1 | 6/2006 | Aurell et al. |
| 2007/0105899 | A1 | 5/2007 | Suzuki et al. |
| 2010/0331303 | A1 | 12/2010 | Kawamoto et al. |
| 2010/0331374 | A1 | 12/2010 | Wu et al. |
| 2012/0329836 | A1 | 12/2012 | Marsh et al. |

FOREIGN PATENT DOCUMENTS

| CA | 2098158 | 12/1993 |
| CA | 2253282 | 11/1997 |
| EP | 2 044 005 B1 | 10/2010 |
| JP | 1997-221476 | 8/1997 |
| JP | 2001-48786 | 2/2001 |
| JP | 2006-11127 | 11/2006 |
| WO | WO 97/41103 A1 | 11/1997 |
| WO | WO 97/44333 A1 | 11/1997 |
| WO | WO 99/19296 A1 | 4/1999 |
| WO | WO 99/48870 A1 | 9/1999 |
| WO | WO 02/074980 A2 | 9/2002 |
| WO | WO 02/074981 A2 | 9/2002 |
| WO | WO 02/083688 A1 | 10/2002 |
| WO | WO 03/028663 A2 | 4/2003 |
| WO | WO 03/032972 A1 | 4/2003 |
| WO | WO 03/049686 A2 | 6/2003 |
| WO | WO 03/053997 A2 | 7/2003 |
| WO | WO 2004/035812 A2 | 4/2004 |
| WO | WO 2004/048383 A1 | 6/2004 |
| WO | WO 2005/007192 A2 | 1/2005 |
| WO | WO 2005/115984 A1 | 12/2005 |
| WO | WO 2005/118836 A2 | 12/2005 |
| WO | WO 2006/019831 A1 | 2/2006 |
| WO | WO 2006/030977 A1 | 3/2006 |
| WO | WO 2006/114213 A1 | 11/2006 |
| WO | WO 2007/038571 A2 | 4/2007 |
| WO | WO 2007/047194 A2 | 4/2007 |
| WO | WO 2007/070359 A2 | 6/2007 |
| WO | WO 2007/082899 A1 | 7/2007 |
| WO | WO 2007/084667 A1 | 7/2007 |
| WO | WO 2007/088571 A1 | 8/2007 |
| WO | WO 2007/103905 A2 | 9/2007 |
| WO | WO 2007/136990 A2 | 11/2007 |
| WO | WO 2007/150011 A2 | 12/2007 |
| WO | WO 2008/089051 A1 | 7/2008 |
| WO | WO 2008/089052 A2 | 7/2008 |
| WO | WO 2008/130508 A1 | 10/2008 |
| WO | WO 2008/130527 A1 | 10/2008 |
| WO | WO 2008/137060 A1 | 11/2008 |

(Continued)

OTHER PUBLICATIONS

Roda J. M. et al., "Stabilization of HIF-2alpha Induces sVEGFR-1 Production from Tumor-Associated Macrophages and Decreases Tumor Growth in a Murine Melanoma Model," J. Immunol. 2012; 189:3168-3177.

Alesso et al., "Improving resins for solid phase synthesis: incorporation of 1-[2-(2-methoxyethoxy)ethoxy]4-vinyl-benzene" *Tetrahedron*: 59, 7163-7169 (2003).

Anderson et al., "Antileukemic Activity of Derivatives of 1,2-Dimethyl-3,4-bis(hydroxymethyl)-5-phenylpyrrole Bis(N-methylcarbamate)" *J Med. Chem.*: vol. 22(8), 977-980 (1979).

Annex et al., "Growth Factor-Induced Therapeutic Angiogenesis in the Heart: Protein Therapy," *Cardiovascular Research*, 65(3):649-655 (2005).

(Continued)

*Primary Examiner* — John Mabry
(74) *Attorney, Agent, or Firm* — Richard S. Echler

(57) ABSTRACT

Disclosed herein is {[5-(3-fluorophenyl)-3-hydroxypyridine-2-carbonyl]-amino}acetic acid and the ester and amide prodrugs thereof, that can stabilize hypoxia inducible factor-2 alpha (HIF-2α) and thereby provide a method for treating cancer. Further disclosed are compositions which comprise {[5-(3-fluorophenyl)-3-hydroxypyridine-2-carbonyl]-amino}acetic acid and/or a prodrug thereof which can be used to treat cancer.

18 Claims, 18 Drawing Sheets

(56) References Cited

FOREIGN PATENT DOCUMENTS

| WO | WO 2008/144266 A1 | 11/2008 |
|----|----|----|
| WO | WO 2009/019656 A1 | 2/2009 |
| WO | WO 2009/037570 A2 | 3/2009 |
| WO | WO 2009/039321 A1 | 3/2009 |
| WO | WO 2009/039323 A1 | 3/2009 |
| WO | WO 2009/043093 A1 | 4/2009 |
| WO | WO 2009/049112 A1 | 4/2009 |
| WO | WO 2009/067790 A1 | 6/2009 |
| WO | WO 2009/070644 A1 | 6/2009 |
| WO | WO 2009/073497 A2 | 6/2009 |
| WO | WO 2009/073669 A1 | 6/2009 |
| WO | WO 2009/086044 A1 | 7/2009 |
| WO | WO 2009/086592 A1 | 7/2009 |
| WO | WO 2009/089547 A1 | 7/2009 |
| WO | WO2012170439 A1 | 12/2012 |
| WO | WO2012170442 A1 | 12/2012 |

OTHER PUBLICATIONS

Ardelt et al., "Estradiol Regulates Angiopoietin-1 mRNA Expression Through Estrogen Receptor-α in a Rodent Experimental Stroke Model," *Stroke*, 36:337-341 (2005).

Auerbach et al., "Angiogenesis Assays: A Critical Overview," *Clinical Chemistry*, 49:32-40 (2003).

Barany et al., "Solid-phase Peptide Synthesis: A Silver Anniversary Report, "*Int. J Peptide Protein Res.*, 30(6):705-739 (1987).

Bartlett et al., "Molecular Recognition in Chemical and Biological Problems, " *Special Pub., Royal Chem. Soc.*, 78, 182-196 Caveat: A Program to Facilitate the Structure-derived Design of Biologically Active Molecules (Apr. 1989).

Böhm, "The Computer Program LUDI: A New Method for the Novo Design of Enzyme Inhibitors," *J Computer-Aided Molecular Design*,6:61-78 (1992).

Branden et al., "Introduction to Protein Structure Second Edition," Garland Publising Inc., New York, 1999, pp. 374-375.

Bussolino, "Molecular Mechanisms of Blood Vessel Formation," *Trends Biochem. Sci.*,22(7):251-256 (1997).

Cunliffe et al., "Novel Inhibitors of Prolyl 4-Hydroxylase. 3. Inhibition by the Substrate Analogue N-Oxaloglycine and Its Derivatives," *J Med. Chem.* 35:2652-2658 (1992).

Elson et al., "Induction of Hypervascularity Without Leakage or Inflammation in Transgenic Mice Overexpressing Hypoxia-Indicible Factor-1α," *Genes & Dev.*,15:2520-2532 (2001).

Flower, "Modelling G-protein-coupled receptors for drug design," *Biochimica et Biophysica Acta*, 1422:207-234 (1999).

Folkman et al., "Tumor Angiogenesis," *The Molecular Basis of Cancer*, Mendelsohn et al., eds., W. B. Saunders, Chapter 10, pp. 206-232 (1995).

Franklin et al., "Approaches to the Design of Anti-Fibrotic Drugs," *Biochem. Soc. Trans.*, 19(4):812-5 (Nov. 1991).

Goodford, "A Computational Procedure for Determining Energetically Favorable Binding Sites on Biologically Important Macromolecules," *J. Med. Chem.*, 28(7):849-857 (1985).

Goodsell et al., "Automated Docking of Substrates to Proteins by Simulated Annealing," *Proteins: Structure, Function, and Genetics*, 8:195-202 (1990).

Ivan et al., "Biochemical purification and pharmacological inhibition of a mammalian prolyl hydroxylase acting on hypoxia-inducible factor," *Proceedings of the National Academy of Science*;99(21) 13459-13464, Oct. 15, 2002.

Jones et al., "Molecular Recognition of Receptor Sites Using a Genetic Algorithm with a Description of Desolvation," *J. Mol. Biol.*, 245:43-53 (1995).

Kaelin, "Proline Hydroxylation and Gene Expression," *Annu. Rev. Biochem.*, 74:115-125 (2005).

Kawashima et al., "Suppressive effect of quinolinic acid an hippuric acid on bone marrow erythroid growth and lymphocyte blast formation in uremia," *Advances in Experimental Medicine and Biology*, (1987), vol. 223, p. 69-72.

Krantz, "Erythropoietin," *Blood*, 77:419-434 (1991).

Kuntz et al., "A Geometric Approach to Macromolecule—Ligand Interactions," *J. Mol. Biol.*, 161:269-288 (1982).

Lee et al., "Structure of Human FIH-1 Reveals a Unique Active Site Pocket and Interaction Sites for HIF-1 and von Hippel Lindau," *JBC*, 278:7558-7563 (2003).

Li et al., "PR39, A Peptide Regulator of Angiogenesis," *Nat Med.*, 6(1):49-55 (2000).

Mancini et al., "Effect of Erythropoietin on Exercise Capacity in Patients with Moderate to Severe Chronic Heart Failure," *Circulation*, 107:294-299 (2003).

McDonough et al., "Cellular Oxygen Sensing: Crystal Structure of Hypoxia-Inducible Factor Prolyl Hydroxylase (PHD2)," *PNAS*, 103(26):9814-9819 (2006).

Miranker et al., "Functionality Maps of Binding Sites: A Multiple Copy Simultaneous Search Method," *Proteins: Structure, Function and Genetics*, 11:29-34 (1991).

Nguyen et al., "Cellular Interactions in Vascular Growth and Differentiation," *Int. Review of Cytology*, 204:1-48 (2001).

Nishibata et al., "Automatic Creation of Drug Candidate Structures Based on Receptor Structure. Starting Point for Artificial Lead Generation," *Tetrahedron*, 47(43):8985-8990 (1991).

O'Reilly et al., "Angiostatin: A Novel Angiogenesis Inhibitor that Mediates the Suppression of Metastases by a Lewis Lung Carcinoma," *Cell*, 79:315-328 (1994).

O'Reilly et al., "Endostatin: An Endogenous Inhibitor of Angiogenesis and Tumor Growth," *Cell*, 88:277-285 (1997).

Peyssonnaux et al., "HIF-1α Expression Regulates the Bactericidal Capacity of Phagocytes," *J. Clinical Invest.*, 115(7):1806-1815, Jul. 1, 2005.

Schoneberg et al., "Structural Basis of G Protein-Coupled Receptor Function," *Molecular and Cellular Endocrinology*, 151:181-193 (1999).

Semenza, "Signal Transduction to Hypoxia-inducible Factor 1," *Biochem. Pharmacol*, 64:993-998 (2002).

Semenza, "Regulation of Erythropoietin Porduction: New Insights into Molecular Mechanisms of Oxygen Homeostasis," *Hematol. Oncol. Clin. North Am.*, 8:863-884 (1994).

Semenza et al., "Transcriptional Regulation of Genes Encoding Glycolytic Enzymes by Hypoxia-Inducible Factor 1," *J. Biol. Chem.*, 269:23757-23763 (1994).

Sexton, "Recent advances in our understanding of peptide hormone receptors and RAMPS," *Current Opinion in Drug Discovery and Development*, 2(5):440-448 (1999).

Sheehan, "3-Hydroxypicolinic Acid and Some of its Derivatives," *J. Organic Chemistry* 3(3):636-638 (1996).

Teicher et al., "Potentiation of Cytotoxic Cancer Therapies by TNP-470 Alone and with Other Anti-Angiogenic Agents," *Int. J. Cancer*, 57:920-925 (1994).

Tzschucke et al., "Fluorous-Silica-Supported Perfluoro-Tagged Palladium Complexes Catalyze Suzuki Coupling in Water" *Helvetica Chimica Acta*; vol. 87 2882-2889 (2004).

Vickerstaffe et al., "Fully Automated Polymer-Assisted Synthesis of 1,5-Biaryl Pyrazoles," *J. Comb. Chem.*, 2004, 6, 332-33.

Vincent et al., "Angiogenesis is Induced in a Rabbit Model of Hindlimb Ischemia by Naked DNA Encoding an HIF-1α/VP16 Hybrid Transcription Factor," *Circulation*, 102:2255-2261 (2000).

Warnecke et al., "Activation of the Hypoxia-Inducible Factor Pathway and Stimulation of Angiogenesis by Application of Prolyl Hydroxylase Inhibitors," *FASEB Journal*, 17:1186-1188 (2003).

Warshakoon et al., "Design and synthesis of substituted pyridine derivatives as HIF-1 alpha prolyl dydroxylase inhibiters," *Bioorg. Med. Chem. Lett.*, Nov. 1, 2006; 16(21):5616-20.

Wax et al., "SM-20 is a Novel 20-kd Protein Whose Expression in the Arterial Wall is Restricted to Smooth Muscle," *Lab. Invest.*, 74(4):797-808 (1996).

Weidner et al., "Tumor Angiogenesis and Metastasis—Correlation in Invasive Breast Carcinoma," *New Eng. J Med.*, 324(1):1-8 (1991).

Wright et al., "Activation of the Prolyl Hydroxylase Oxygen-Sensor Results in Induction of GLUT1, Heme Oxygenase-1, and Nitric-Oxide Synthase Proteins and Confers Protection from Metabolic Inhibition to Cardiomyocytes," *J. Bio. Chem.*, 278(22):20235-20239 (2003).

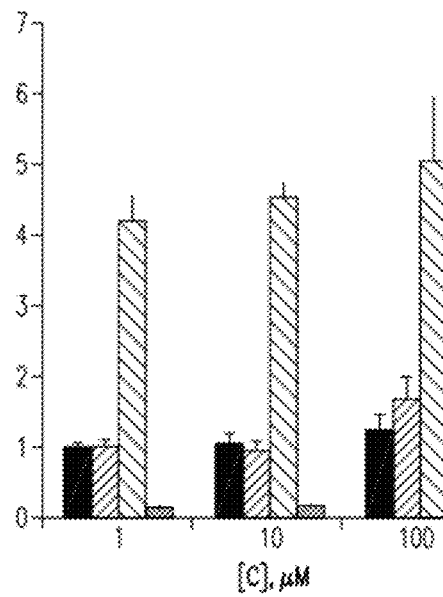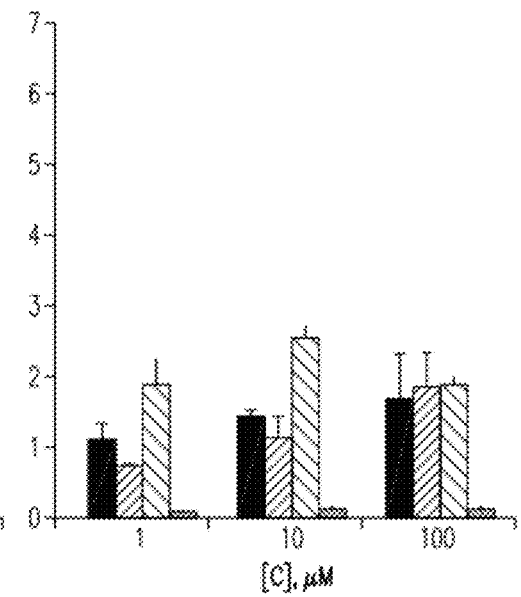
FIG. 1a  FIG. 1b
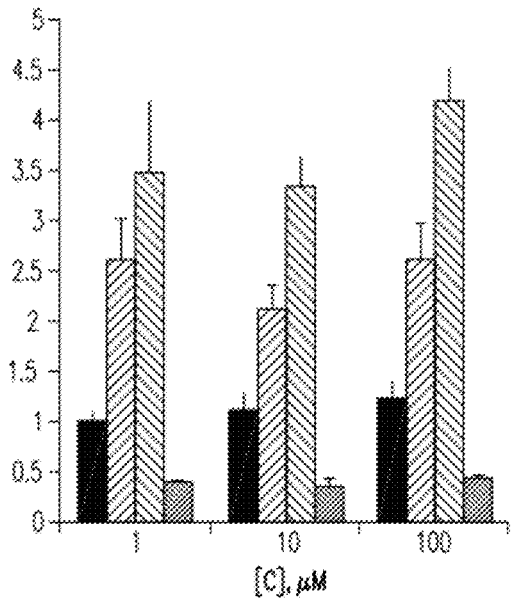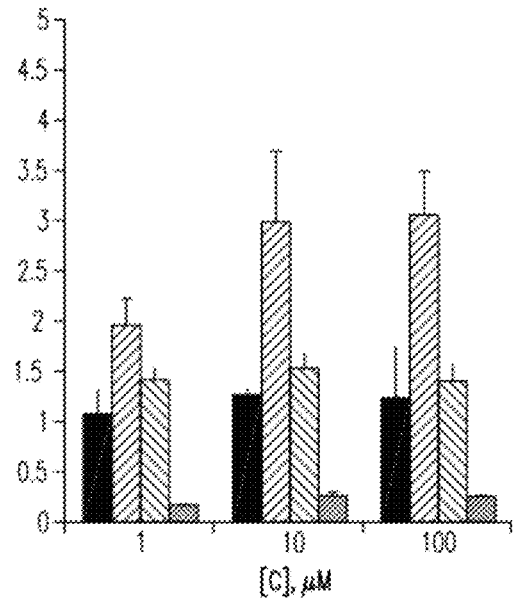
FIG. 2a  FIG. 2b

COMPOUNDS AND COMPOSITIONS FOR STABILIZING HYPOXIA INDUCIBLE FACTOR-2 ALPHA AS A METHOD FOR TREATING CANCER

PRIORITY

This application claims the benefit of Provisional Application Ser. No. 61/493,534, filed on Jun. 6, 2011, the entirety of which is incorporated herein by reference.

FIELD

Disclosed herein is {[5-(3-fluorophenyl)-3-hydroxypyridine-2-carbonyl]-amino}acetic acid and the ester and amide prodrugs thereof, that can stabilize hypoxia inducible factor-2 alpha (HIF-2α) and thereby provide a method for treating cancer. Further disclosed are compositions which comprise {[5-(3-fluorophenyl)-3-hydroxypyridine-2-carbonyl]-amino}acetic acid and/or a prodrug thereof which can be used to treat cancer.

BACKGROUND

Nobel Prize winner Dr. Judah Folkman first proposed in 1971 that all cancer tumors were angiogenesis-dependent and therefore targeting angiogenesis was a potential means for treating cancer. Angiogenesis is the growth of new capillaries from pre-existent microvasculature. A wide range of pathological conditions, from atherosclerosis to cancer, are associated with either excessive or deficient angiogenesis.

It is now widely accepted that tumor growth beyond a few cubic millimeters cannot occur without the induction of a new vascular supply. Therefore, inhibition of new vasculature (antiangiognesis) can provide a non-chemotherapy or non-radiation therapy approach to the treatment of cancer by denying tumors the nutrient supply necessary for the tumors to grow. Although normally quiescent, endothelial cells are responsible for the formation of new vasculature in response to various stimuli. These stimuli can have their genesis in many forms.

The endothelial cells which form new vascular networks in tumors respond to angiogenic stimuli produced by the tumor itself. The best known of these stimuli is vascular endothelial growth factor (VEGF). Found to be ubiquitous in human tumors, increasing levels of VEGF correlate with an increasing rate of tumor growth. Therefore, suppression of VEGF represents a method for controlling the growth rate of tumors (primary and metastatic) and offers a possible means for shrinking existing tumors.

Therefore, there is a long felt need for compounds, compositions, and methods for suppressing VEGF expression by tumor cells.

BRIEF DESCRIPTION OF THE FIGURES

FIG. 1A depicts the reduction in mRNA expression of VEGF in wild type murine embryonic fibroblasts under normoxia (21% $O_2$) vs. cells under hypoxic conditions (1% $O_2$) at various concentrations of HIF-2α stabilizer, {[5-(3-fluorophenyl)-3-hydroxypyridine-2-carbonyl]-amino}acetic acid. The disclosed HIF-2α stabilizer was tested at 1, 10 and 100 μM concentrations vs. control. The data indicate the relative amounts of VEGF mRNA and are as follows from left to right normoxia control (solid black), HIF2-α stabilizer normoxia, hypoxia control and HIF2-α stabilizer hypoxia. The amount of VEGF mRNA present is dramatically reduced at all concentrations of HIF-2α stabilizer under hypoxic conditions (far right data for each concentration).

FIG. 1B depicts the reduction in mRNA expression of VEGF in murine fibroblasts embryonic having deletion of HIF1-α, i.e., HIF-1α$^{-/-}$ fibroblasts under normoxia (21% $O_2$) vs. cells under hypoxic conditions (1% $O_2$) at various concentrations of HIF-2α stabilizer, {[5-(3-fluorophenyl)-3-hydroxypyridine-2-carbonyl]-amino}acetic acid. The disclosed HIF-2α stabilizer was tested at 1, 10 and 100 μM concentrations vs. control. The data indicate the relative amount of VEGF mRNA and are as follows from left to right normoxia control (solid black), HIF-α stabilizer normoxia, hypoxia control and HIF2-α stabilizer hypoxia. The amount of VEGF mRNA present is dramatically reduced at all concentrations of HIF-2α stabilizer under hypoxic conditions even in mice having deletion of HIF1-α (far right data for each concentration).

FIG. 2A depicts the reduction in mRNA expression of phosphoglycerate kinase (PGK) in wild type murine embryonic fibroblasts under normoxia (21% $O_2$) vs. cells under hypoxic conditions (1% $O_2$) at various concentrations of HIF-2α stabilizer, {[5-(3-fluorophenyl)-3-hydroxypyridine-2-carbonyl]-amino}acetic acid. The disclosed HIF-2α stabilizer was tested at 1, 10 and 100 μM concentrations vs. control. The data indicate the relative amounts of PGK present and are as follows from left to right normoxia control (solid black), HIF2-α stabilizer normoxia, hypoxia control and HIF2-α stabilizer hypoxia. The amount of phosphoglycerate kinase (PGK) mRNA present is dramatically reduced at all concentrations of HIF-2α stabilizer under hypoxic conditions.

FIG. 2B depicts the reduction in mRNA expression of phosphoglycerate kinase (PGK) in murine fibroblasts embryonic having deletion of HIF1-α, i.e., HIF-1α$^{-/-}$ fibroblasts under normoxia (21% $O_2$) vs. cells under hypoxic conditions (1% $O_2$) at various concentrations of HIF-2α stabilizer, {[5-(3-fluorophenyl)-3-hydroxypyridine-2-carbonyl]-amino}acetic acid. The disclosed HIF-2α stabilizer was tested at 1, 10 and 100 μM concentrations vs. control. The data indicate the relative amounts of PGK present and are as follows from left to right normoxia control (solid black), HIF2-α stabilizer normoxia, hypoxia control and HIF2-α stabilizer hypoxia (Bar D, lightest gray). The amount of phosphoglycerate kinase (PGK) mRNA present is dramatically reduced at all concentrations of HIF-2α stabilizer under hypoxic conditions even in mice having deletion of HIF1-α (far right data for each concentration).

FIG. 3 indicates that the disclosed HIF-2α stabilizer reduces tumor growth alone (Δ) comparable to GM-CSF alone (■) and the inhibition of tumor growth is additive when the disclosed HIF-2α stabilizer is used in combination with GM-CSF (X) vs. phosphate buffered saline (PBS) (control) (♦).

FIG. 12B—a 3-day increase in median survival (which was defined as the time to a tumor diameter of 20 mm$^3$) in mice treated with disclosed HIF-2α stabilizer ($p=0.023$).

DETAILED DESCRIPTION

Figure 3:
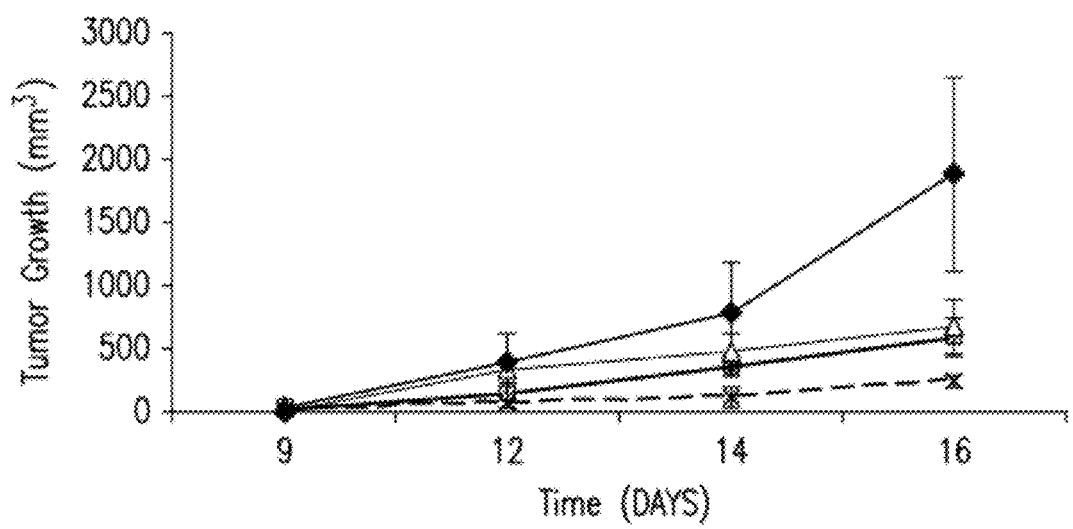
FIG. 3 depicts the reduction in tumor growth in C57BL/6 mice bearing B16F10 melanoma tumors as compared to treatment with granulocyte-macrophage colony-stimulating factor (GM-CSF).

The materials, compounds, compositions, articles, and methods described herein may be understood more readily by reference to the following detailed description of specific aspects of the disclosed subject matter and the Examples included therein. Before the present materials, compounds, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

GENERAL DEFINITIONS

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

A weight percent of a component, unless specifically stated to the contrary, is based on the total weight of the formulation or composition in which the component is included.

By "effective amount" as used herein means "an amount of one or more of the disclosed compounds, effective at dosages and for periods of time necessary to achieve the desired or therapeutic result." An effective amount may vary according to factors known in the art, such as the disease state, age, sex, and weight of the human or animal being treated. Although particular dosage regimes may be described in examples herein, a person skilled in the art would appreciate that the dosage regime may be altered to provide optimum therapeutic response. For example, several divided doses may be administered daily or the dose may be proportionally reduced as indicated by the exigencies of the therapeutic situation. In addition, the compositions of this disclosure can be administered as frequently as necessary to achieve a therapeutic amount.

"Admixture" or "blend" is generally used herein means a physical combination of two or more different components "Excipient" is used herein to include any other compound that may be contained in or combined with one or more of the disclosed inhibitors that is not a therapeutically or biologically active compound. As such, an excipient should be pharmaceutically or biologically acceptable or relevant (for example, an excipient should generally be non-toxic to the subject). "Excipient" includes a single such compound and is also intended to include a plurality of excipients.

"Excipient" is used herein to include any other compound that may be contained in or combined with one or more of the disclosed inhibitors that is not a therapeutically or biologically active compound. As such, an excipient should be pharmaceutically or biologically acceptable or relevant (for example, an excipient should generally be non-toxic to the subject). "Excipient" includes a single such compound and is also intended to include a plurality of excipients.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., vascular leakage). It is understood that this is typically in relation to some standard or expected value, in other words it is relative, but that it is not always necessary for the standard or relative value to be referred to.

The term "treat" or other forms of the word such as "treated" or "treatment" is used herein to mean that administration of a compound of the present invention mitigates a disease or a disorder in a host and/or reduces, inhibits, or eliminates a particular characteristic or event associated with a disorder (e.g., vascular leakage). Thus, the term "treatment" includes, preventing a disorder from occurring in a host, particularly when the host is predisposed to acquiring the disease, but has not yet been diagnosed with the disease; inhibiting the disorder; and/or alleviating or reversing the disorder. Insofar as the methods of the present invention are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present invention may occur prior to onset of a disease. The term does not imply that the disease state be completely avoided.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "a chemotherapeutic agent" includes mixtures of two or more such chemotherapeutic agents, reference to "the compound" includes mixtures of two or more such compounds, for example, salts thereof, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

"VEGF-dependent cancer," "VEGF dependent cancers," VEGF-dependent tumor" or "VEGF dependent tumors" refers to cancers that rely on VEGF to proliferate.

For the purposes of the present disclosure the term "$C_1$-$C_4$ linear, $C_3$-$C_4$ branched or $C_3$-$C_4$ cyclic alkyl" includes the following units methyl ($C_1$), ethyl ($C_2$), n-propyl ($C_3$), iso-propyl ($C_3$), cyclopropyl ($C_3$), n-butyl ($C_4$), sec-butyl ($C_4$), iso-butyl ($C_4$), tert-butyl ($C_4$) and cyclobutyl ($C_4$).

Disclosed herein are compounds having the formula:

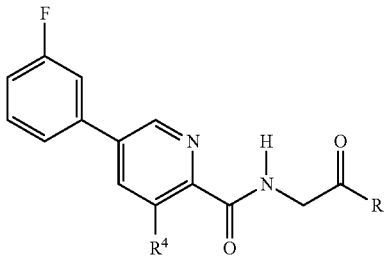

wherein R is chosen from:
i) —OR$^1$;
ii) —NR$^2$R$^3$; or
iii) —OM$^1$;

R$^1$ is:
i) hydrogen; or
ii) $C_1$-$C_6$ linear, $C_3$-$C_6$ branched or $C_3$-$C_6$ cyclic alkyl;

R$^2$ and R$^3$ are independently:
i) hydrogen;
ii) $C_1$-$C_6$ linear, $C_3$-$C_6$ branched or $C_3$-$C_6$ cyclic alkyl; or
iii) R$^2$ and R$^3$ can be taken together to form a ring having from 2 to 7 carbon atoms and from 1 to 3 heteroatoms chosen from nitrogen, oxygen and sulfur including the nitrogen atom to which R$^2$ and R$^3$ are bonded.

M$^1$ represents a cation as further described herein below.

R$^4$ is chosen from:
i) —OH; or
ii) —OM$^2$;

wherein M$^2$ is a cation as further described herein below.

The disclosed compound {[5-(3-fluorophenyl)-3-hydroxypyridine-2-carbonyl]-amino}acetic acid having the formula:

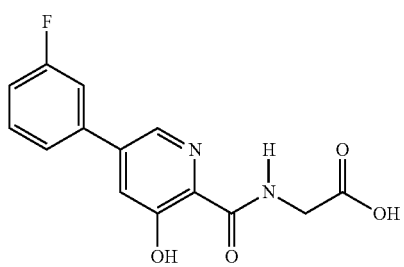 [SMILES: O=C(O)CNC(=O)c1ncc(-c2cccc(F)c2)cc1O]

has been found to stabilize hypoxia inducible factor two-alpha (HIF-2α) and, as further disclosed herein, exhibits anti-angiogenic behavior by inducing production of the endogenous Vascular Endothelial Growth Factor inhibitor, s-VEGF-1.

Also disclosed are pharmaceutically acceptable salts of the disclosed stabilizer having the formula:

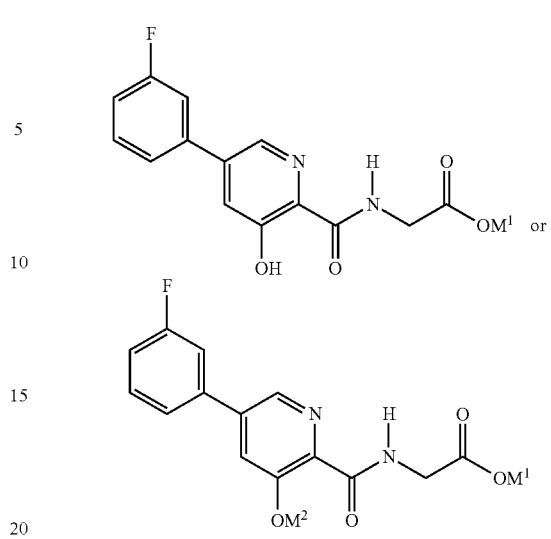

wherein M$^1$ and M$^2$ are each independently a mono-, di-, or tri-valent cation, i.e., M$^+$, M$^{2+}$, or M$^{3+}$.

One aspect of the disclosed salts relates to the stabilizer in the form of the mono-valent salt having the formula:

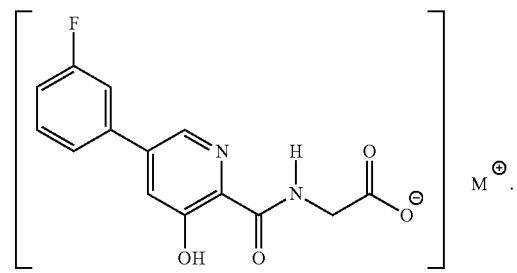

One embodiment of this aspect relates to the disclosed stabilizer wherein M$^1$ is an inorganic cation. One iteration of relates to inorganic cations chosen from sodium, lithium, potassium, ammonium, and silver. Non-limiting examples include:

i) sodium {[5-(3-fluorophenyl)-3-hydroxypyridine-2-carbonyl]-amino}acetate;
ii) potassium {[5-(3-fluorophenyl)-3-hydroxypyridine-2-carbonyl]-amino}acetate; and
iii) ammonium {[5-(3-fluorophenyl)-3-hydroxypyridine-2-carbonyl]-amino}acetate.

Another embodiment of this aspect relates to the disclosed stabilizer wherein M$^1$ is an organic cation. One embodiment of relates to organic cations that are amines, for example, salts having the formula:

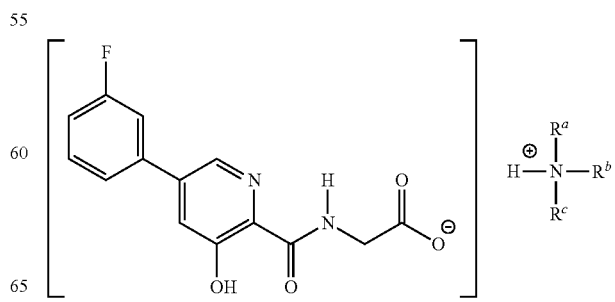

$R^a$, $R^b$ and $R^c$ are each independently:
  i) hydrogen;
  ii) substituted or unsubstituted $C_1$-$C_{12}$ linear, $C_3$-$C_{12}$ branched, or $C_3$-$C_{12}$ cyclic alkyl;
  iii) substituted or unsubstituted benzyl;
wherein one or more of $R^a$, $R^b$ and $R^c$ can be independently substituted by one or more units chosen from:
  i) $C_1$-$C_{12}$ linear, $C_3$-$C_{12}$ branched, or $C_3$-$C_{12}$ cyclic alkoxy;
  ii) $C_1$-$C_{12}$ linear, $C_3$-$C_{12}$ branched, or $C_3$-$C_{12}$ cyclic haloalkoxy;
  iii) halogen;
  iv) hydroxyl;
  v) thio; or
  vi) one or more of $R^a$, $R^b$ and $R^c$ can contain one or more units capable of forming a cation, anion, or zwitterions.

One iteration of this embodiment relates to cations wherein each of $R^a$, $R^b$ and $R^c$ are hydrogen or $C_1$-$C_{12}$ linear alkyl. Non-limiting examples include methyl ammonium [$HN^+H_2(CH_3)$], dimethyl ammonium [$HN^+H(CH_3)_2$], trimethyl ammonium [$HN^+(CH_3)_3$], ethyl ammonium [$HN^+H_2(CH_2CH_3)$], diethyl ammonium [$HN^+H(CH_2CH_3)_2$], triethyl ammonium [$HN^+(CH_2CH_3)_3$], dimethylethyl ammonium [$HN^+(CH_3)_2(CH_2CH_3)$], and methyldiethyl ammonium [$HN^+(CH_3)(CH_2CH_3)_2$].

Another iteration of this embodiment relates to cations wherein one or more of $R^a$, $R^b$ and $R^c$ are chosen from hydrogen, unsubstituted $C_1$-$C_{12}$ linear, $C_3$-$C_{12}$ branched, or $C_3$-$C_{12}$ cyclic alkyl or substituted $C_1$-$C_{12}$ linear, $C_3$-$C_{12}$ branched, or $C_3$-$C_{12}$ cyclic alkyl. One embodiment relates to organic cations having one or more $C_1$-$C_{12}$ linear, $C_3$-$C_{12}$ branched, or $C_3$-$C_{12}$ cyclic alkyl chains substituted with hydroxy. Non-limiting examples include 2-hydroxyethyl ammonium (cation of monoethanolamine, cholinate) [$HN^+H_2(CH_2CH_2OH)$], methyl-2-hydroxyethyl ammonium [$H_2N^+(CH_3)(CH_2CH_2OH)$], di-(2-hydroxyethyl) ammonium [$H_2N^+(CH_2CH_2OH)_2$], tri-(2-hydroxyethyl) ammonium [$HN^+(CH_2CH_2OH)_3$], and tris-(hydroxymethyl)methyl ammonium (cation of tris-(hydroxymethyl)aminomethane) [$H_3N^+C[(CH_2OH)_3]$]. Also included are cations formed from amino sugars, for example, amino sugars having the formula $H_2N^+(CH_3)CH_2[(CHOH)_nCH_2OH]$ wherein n is from 1 to 7. A non-limiting example of an amino sugar suitable for forming an organic cation is meglumine (1-deoxy-1-methylamino-sorbitol).

A further iteration of this embodiment relates to cations formed from amino acids. Non-limiting examples include lysine, ornithine, arginine, glutamine, and the like.

Another aspect of organic amines suitable for forming salts of the disclosed stabilizer include amines wherein one or more of $R^a$, $R^b$ and $R^c$ are taken together to form a heterocyclic ring that can comprise from 3 to 20 atoms and optionally one or more heteroatoms chosen from nitrogen, oxygen and sulfur. Non-limiting examples include piperazine, piperidine, morpholine, thiomorpholine, and the like.

Another organic amine suitable for use as a cation forming compound includes benzathine. Benzathine can be a mono- or di-cation, for example, salts of N-benzyl-2-(benzylamino)ethanaminium having the formula:

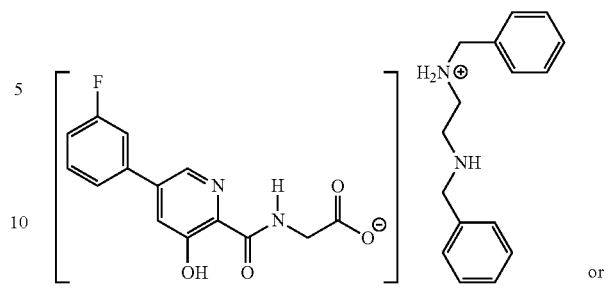

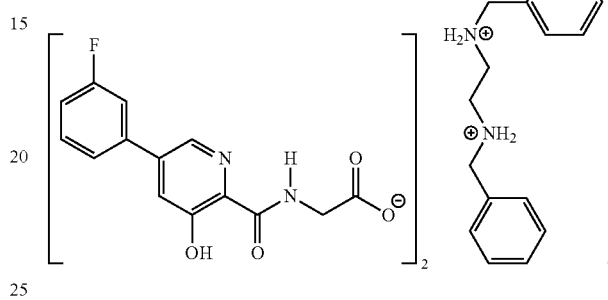

Another aspect of the disclosed salts relates to the stabilizer in the form of the di-valent salt having the formula:

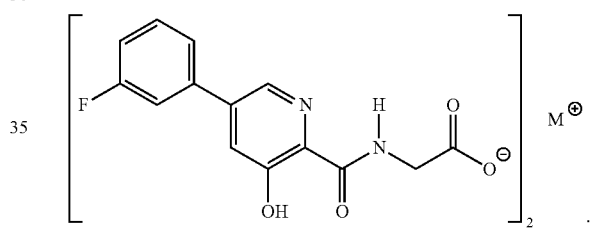

One embodiment of this aspect relates to the disclosed stabilizer wherein $M^1$ is an inorganic cation. One iteration of relates to inorganic cations chosen from calcium, magnesium, barium, and the like. Non-limiting examples include:
  i) calcium bis{[5-(3-fluorophenyl)-3-hydroxypyridine-2-carbonyl]-amino}acetate;
  ii) magnesium bis{[5-(3-fluorophenyl)-3-hydroxypyridine-2-carbonyl]-amino}acetate; and
  iii) barium bis{[5-(3-fluorophenyl)-3-hydroxypyridine-2-carbonyl]-amino}acetate.

Another aspect of the pharmaceutically acceptable salts relates to salts wherein R is $OM^1$ and $R^4$ is $OM^2$, for example, salts having the formula:

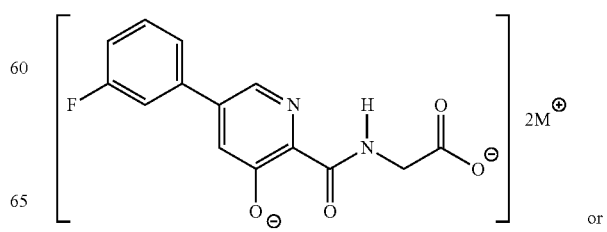

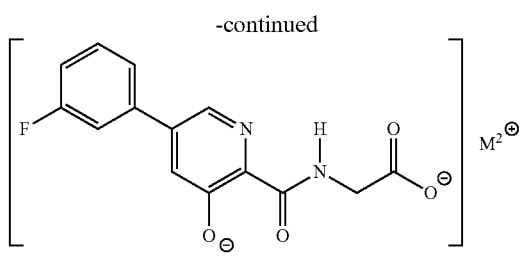

A first embodiment relates to salts comprising a plurality of mono-valent inorganic cations. For example:
i) disodium {[5-(3-fluorophenyl)-3-oxidopyridine-2-carbonyl]-amino}acetate;
ii) dipotassium {[5-(3-fluorophenyl)-3-oxidopyridine-2-carbonyl]-amino}acetate;
iii) diammonium {[5-(3-fluorophenyl)-3-oxidopyridine-2-carbonyl]-amino}acetate;
iv) sodium potassium {[5-(3-fluorophenyl)-3-oxidopyridine-2-carbonyl]-amino}acetate;
v) sodium ammonium {[5-(3-fluorophenyl)-3-oxidopyridine-2-carbonyl]-amino}acetate; and
vi) potassium ammonium {[5-(3-fluorophenyl)-3-oxidopyridine-2-carbonyl]-amino}acetate.

In another embodiment, organic amines capable for forming di-cationic species, for example, benzathine as disclosed herein can be used to form suitable pharmaceutically acceptable salts of the disclosed stabilizer.

In addition, disclosed herein are prodrugs that are converted to the active compound {[5-(3-fluorophenyl)-3-hydroxypyridine-2-carbonyl]-amino}acetic acid in vivo. The disclosed prodrugs have the formula:

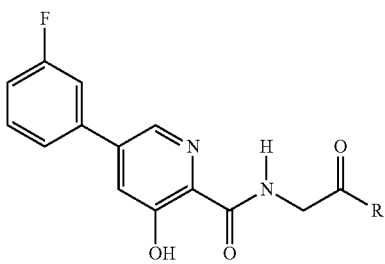

wherein R is chosen from:
i) —OR$^1$; or
ii) —NR$^2$R$^3$;
R$^1$ is C$_1$-C$_6$ linear, C$_3$-C$_6$ branched or C$_3$-C$_6$ cyclic alkyl; and R$^2$ and R$^3$ are independently:
i) hydrogen;
ii) C$_1$-C$_6$ linear, C$_3$-C$_6$ branched or C$_3$-C$_6$ cyclic alkyl; or
iii) R$^1$ and R$^2$ can be taken together to form a ring having from 2 to 7 carbon atoms and from 1 to 3 heteroatoms chosen from nitrogen, oxygen and sulfur including the nitrogen atom to which R$^1$ and R$^2$ are bonded.

One aspect of the disclosed prodrugs relates to compounds that are esters, i.e., R$^1$ is C$_1$-C$_6$ linear, C$_3$-C$_6$ branched or C$_3$-C$_6$ cyclic alkyl. In one embodiment, R$^1$ is methyl (C$_1$) thereby providing the prodrug methyl {[5-(3-fluorophenyl)-3-hydroxypyridine-2-carbonyl]amino}acetate. In another embodiment, R$^1$ is ethyl (C$_2$) thereby providing the prodrug ethyl {[5-(3-fluorophenyl)-3-hydroxypyridine-2-carbonyl]amino}acetate.

In a further embodiment, R$^1$ is chosen from C$_3$-C$_4$ linear, branched or cyclic alkyl, for example, n-propyl (C$_3$), iso-propyl (C$_3$), cyclopropyl (C$_3$), n-butyl (C$_4$), sec-butyl (C$_4$), iso-butyl (C$_4$), tert-butyl (C$_4$) and cyclobutyl (C$_4$).

Another aspect of the disclosed prodrugs relates to compounds that are amides, i.e., R is —NR$^2$R$^3$. In one embodiment of this aspect, R$^2$ and R$^3$ are both hydrogen wherein R is —NH$_2$ thereby affording the prodrug 5-(3-fluorophenyl)-N-(2-amino-2-oxoethyl)-3-hydroxypyridin-2-yl amide. In another embodiment, R$^1$ is methyl (C$_1$) and R$^2$ is hydrogen thereby affording the prodrug 5-(3-fluorophenyl)-N-(2-methylamino-2-oxoethyl)-3-hydroxypyridin-2-yl amide. A yet another embodiment, R$^1$ and R$^2$ are both methyl (C$_1$) thereby affording the prodrug 5-(3-fluorophenyl)-N-(2-dimethylamino-2-oxoethyl)-3-hydroxypyridin-2-yl amide.

In a further embodiment of this aspect, R$^2$ and R$^3$ are each independently hydrogen, ethyl, n-propyl (C$_3$), iso-propyl (C$_3$), cyclopropyl (C$_3$), n-butyl (C$_4$), sec-butyl (C$_4$), iso-butyl (C$_4$), tert-butyl (C$_4$) or cyclobutyl (C$_4$). Non-limiting examples of prodrugs according to this aspect include 5-(3-fluorophenyl)-N-(2-diethylamino-2-oxoethyl)-3-hydroxypyridin-2-yl amide; 5-(3-fluorophenyl)-N-(2-propylamino-2-oxoethyl)-3-hydroxypyridin-2-yl amide; 5-(3-fluorophenyl)-N—(N-ethyl-N-isopropylamino-2-oxoethyl)-3-hydroxypyridin-2-yl amide; 5-(3-fluorophenyl)-N-(2-diisopropylamino-2-oxoethyl)-3-hydroxypyridin-2-yl amide; 5-(3-fluorophenyl)-N-(2-cyclopropylamino-2-oxoethyl)-3-hydroxypyridin-2-yl amide; and 5-(3-fluorophenyl)-N-(2-butylamino-2-oxoethyl)-3-hydroxypyridin-2-yl amide.

In a still further embodiment of this aspect, R$^1$ and R$^2$ can be taken together to form a ring having from 2 to 7 carbon atoms and from 1 to 3 heteroatoms chosen from nitrogen, oxygen and sulfur including the nitrogen atom to which R$^1$ and R$^2$ are bonded. In a first iteration of this embodiment, R$^1$ and R$^2$ are taken together with the nitrogen atom to which they are bonded to form a ring chosen from aziridinyl (C$_2$), azetidinyl (C$_3$), pyrrolidinyl (C$_4$) and piperidinyl (C$_4$).

In a further iteration of this embodiment, R$^1$ and R$^2$ are taken together with the nitrogen atom to which they are bonded to form a ring comprising a second heteroatom chosen from nitrogen, oxygen and sulfur. Non-limiting examples of these rings include thiazolyl (C$_3$), isothiazolyl (C$_3$), oxazolyl (C$_3$), isoxazolyl (C$_3$), imidazolyl (C$_3$), morpholinyl (C$_4$) and piperazinyl (C$_5$).

The disclosed HIF-2α stabilizer, 6, and ester prodrugs, for example, compound 5, can be prepared by the process outlined in Scheme I and further described in Example 1 herein below.

Scheme I

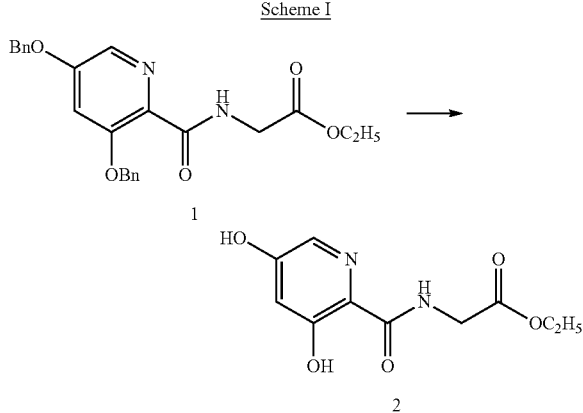

Reagents and conditions: (a) H$_2$: Pd/C, EtOH, rt, 16 hr.

-continued

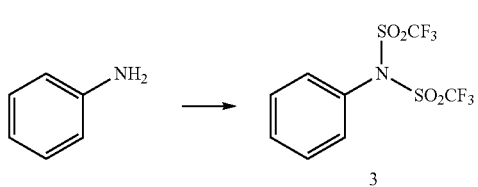

Reagents and conditions: (b) (CF₃O₂S)₂O, Et₃N, CH₂Cl₂;, rt, 16 hr.

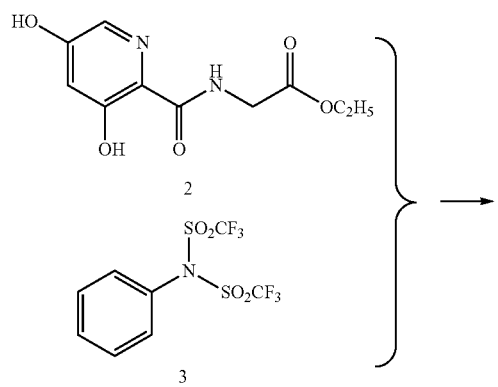

Reagents and conditions: (c) Et₃N, Na₂CO₃, EtOH, rt, 16 hr.

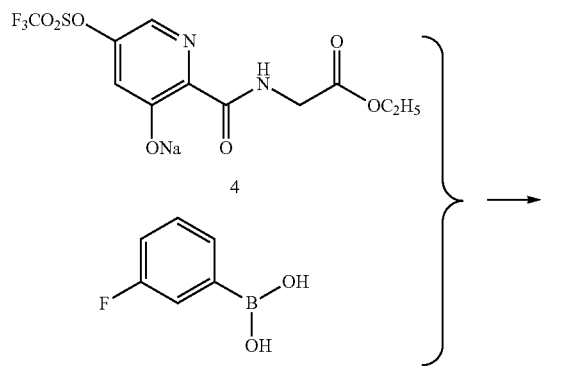

Reagents and conditions: (d) Pd(dppf)Cl₂, K₃PO₄, H₂O, dioxane; 85° C., 16 hr.

-continued

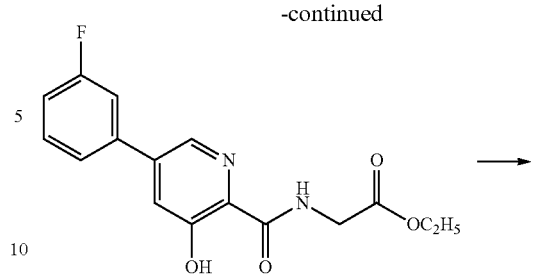

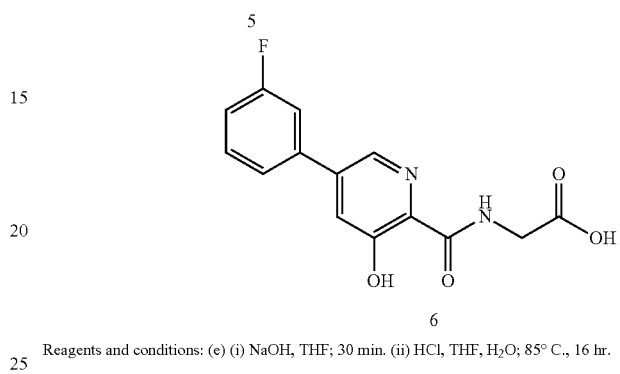

Reagents and conditions: (e) (i) NaOH, THF; 30 min. (ii) HCl, THF, H₂O; 85° C., 16 hr.

Example 1

{[5-(3-Fluorophenyl)-3-hydroxypyridine-2-carbonyl]amino}acetic acid (6)

In the reactions described herein below, unless otherwise stated, temperatures are given in degrees Celsius (° C.); operations were carried out at room or ambient temperature, "room temperature," "rt," or "RT" (typically a range of from about 18° C. to about 25° C.; evaporation of solvent was carried out using a rotary evaporator under reduced pressure (typically, 4.5-30 mm Hg) with a bath temperature of up to 60° C.; the course of reactions was typically followed by thin layer chromatography (TLC); products exhibited satisfactory $^1$H NMR, HPLC, and/or LC-MS (GC-MS) data; and the following conventional abbreviations are also used: L (liter(s)), mL (milliliters), mmol (millimoles), g (grams), and mg (milligrams). Unless specified otherwise, all solvents and reagents were purchased from suppliers and used without further purification. Reactions were conducted under a blanket of nitrogen unless otherwise stated. Compounds were visualized under UV lamp (254 nm). $^1$H NMR spectra were recorded on a 300 MHz NMR.

Preparation of [(3,5-dihydroxypyridine-2-carbonyl)-amino]-acetic acid ethyl ester (2): To a 20 L round-bottomed flask was charged nitrogen and palladium on carbon (10% Pd/C) (100 g, 60% wet paste) and ethanol (12 L), followed by the addition of [(3,5-bis-benzyloxypyridine-2-carbonyl)-amino]-acetic acid ethyl ester, 1, (1000 g, 2.378 mol). The resulting mixture was subjected to a vacuum-nitrogen purge cycle three times and a vacuum-hydrogen purge cycle three times. A hydrogen atmosphere was introduced and the reaction mixture was stirred at 1-25° C. until the completion of the reaction by TLC analysis. The reaction typically lasted 2 to 3 hours and a vigorous stirring was important to complete the reaction. The reaction system was then subjected to a vacuum-nitrogen purge cycle to remove hydrogen from the system. The reaction mixture was filtered and the filter-cake was washed with ethanol (2 L). The combined filtrate was concentrated on a rotary evaporator at up to 45° C. bath temperature to a constant weight to provide 558 g (97.7% yield) of the desired product as an off-white solid. MP: 138-

140° C.; MS (ESI+): m/z 241 (M+1); $^1$H NMR (300 MHz, DMSO-d$_6$) δ 12.28 (s, 1H), 10.79 (s, 1H), 9.09-9.05 (t, J=6 Hz, 1H), 7.76-7.71 (d, J=2.4 Hz, 1H), 6.68-6.67 (d, J=2.1 Hz, 1H), 4.15-4.08 (q, J=6.9 Hz, 2H), 4.02-4.00 (d, J=6.3 Hz, 2H), 1.22-1.17 (t, J=6.9 Hz, 2H).

Preparation of N-phenylbis(trifluormethane-sulfinimide) (3): To a 10 L found-bottomed flask was charged aniline (232.5 g, 2.5 mol), triethylamine (505 g, 5 mol) and dichloromethane (5 L). The resulting mixture was cooled with an ice bath. Trifluoromethanesulfonic anhydride (1410 g, 5 mol) in dichlolormethane (1 L) was added dropwise. The reaction mixture was allowed to warm to RT and stirred overnight. The reaction was then added to crushed ice (4 kg) while stirring. The resulting biphasic mixture was separated. The organic layer was washed with brine (2 L×2), dried over Na$_2$SO$_4$, filtered and concentrated to form a crude solid product. The crude solid was washed with ethanol to produce 767 g (86% yield) of the desired product as a white solid. MP: 96-98° C.; $^1$H NMR (300 MHz, CDCl$_3$) δ 7.64-7.51 (m, 3H), 7.44-7.42 (m, 2H).

Preparation of [(3-hydroxy-5-trifluoromethanesulfonyloxypyridine-2-carbonyl)-amino]-acetic acid ethyl ester sodium salt (4): To a 20 L round-bottomed flask was charged [(3,5-dihydroxy-pyridine-2-carbonyl)-amino]-acetic acid ethyl ester, 2, (860 g, 3.58 mol) and ethanol (11 L). The mixture was stirred to form a solution at 10 to 20° C. Triethylamine (602 mL, 4.3 mol) was added. The resulting mixture was cooled to 0-5° C. and N-phenylbis(trifluormethane-sulfinimide), 3, (1406 g, 3.94 mol) was added. After addition, the reaction mixture was warmed to 35 to 40° C. and stirred overnight. TLC analysis indicated that the reaction was complete. The reaction mixture was then concentrated by rotary evaporation at up to 40° C. bath temperature. The residue (oily solid) was treated with toluene (4.5 L) and concentrated to approximately 4.5 L. The toluene solvent swap was repeated until residue ethanol level became less than 0.5% by $^1$H NMR analysis. The toluene solution was treated with 10% w/w aqueous Na$_2$CO$_3$ solution (5.5 L, 1.3 eq.). The resulting slurry was filtered and the filter cake was washed with water (2×2 L) and then a mixture of toluene/TBME (1:2) (2×2 L). The solid product was dried to afford 1156 g (82% yield) of the desired product as a white solid. MS (ESI+): m/z 373 (M+1); $^1$H NMR (300 MHz, DMSO-d$_6$) δ 12.13 (1H, s), 7.43-7.42 (d, J=2.1 Hz, 1H), 6.72-6.71 (d, J=2.1 Hz, 2H), 4.12-4.05 (m, 4H), 1.21-1.15 (t, J=6.9 Hz, 3).

Preparation of {[5-(3-fluorophenyl)-3-hydroxypyridine-2-carbonyl]amino}acetic acid ethyl ester (5): To a 5 L round-bottomed flask was charged [(3-hydroxy-5-trifluoromethane-sulfonyloxypyridine-2-carbonyl)-amino]-acetic acid ethyl ester sodium salt, 4, (310 g, 0.78 mol), 1,4-dioxane (3 L) and water (150 mL). The solution was subjected to a vacuum-nitrogen purge cycle, followed by the addition of potassium phosphate (50 g, 0.234 mol) and 3-fluorophenylboronic acid (163 g, 1.17 mol). After addition, the vacuum-nitrogen purge cycle was repeated once. 1,1-Bis(diphenyl-phosphino)ferrocenepalladium (II) chloride CH$_2$Cl$_2$ complex (72 g, 0.088 mol, 0.11 eq.) was then added. After another vacuum-nitrogen purge cycle, the reaction mixture was then heated to 75 to 85° C. The progress of the reaction was monitored by TLC. The reaction was complete after 14-16 hours. The reaction was cooled to 15 to 25° C. and concentrated by rotary evaporation at up to 45° C. bath temperature until solvent collection had ceased. The residue was treated with an aqueous solution of HCl (1M, 1.5 L) and ethyl acetate (1.5 L) and stirred for 30 minutes at room temperature. The layers were then separated. The organic layer was washed with water (1.5 L), brine (1.5 L), dried over Na$_2$SO$_4$, filtered and concentrated. The crude product was purified by silica gel column chromatography (hexane/ethylacetate/acetic acid: 3:1:0.01 by vol/vol) to afford 226 g (90% yield) of the desired product. MS (ESI+): m/z 319 (M+1); $^1$H NMR (300 MHz, CDCl$_3$) δ 11.88 (s, 1H), 8.44 (s, 1H), 8.32-0.31 (d, J=1.5 Hz, 1H), 7.51-7.44 (m, 2H), 7.40-7.37 (m, 1H), 7.32-7.27 (m, 1H), 7.17-7.13 (t, J=6.6 Hz, 1H), 4.33-4.25 (m, 4H), 1.36-1.31 (t, J=7.2 Hz, 3H).

Preparation of {[5-(3-fluorophenyl)-3-hydroxypyridine-2-carbonyl]amino}acetic acid (6): To a slurry of {[5-(3-fluorophenyl)-3-hydroxypyridine-2-carbonyl]amino}acetic acid ethyl ester, 5, (226 g, 0.71 mol) in THF (1 L) at room temperature was added an aqueous solution of sodium hydroxide (1 M, 2 L) while maintaining the internal reaction temperature below 25° C. The progress of the reaction was monitored by TLC. After 20-30 minutes, the reaction was completed. The pH of the reaction solution was adjusted using concentrated HCl to 5-5.5 while maintaining the internal temperature below 25° C. The reaction mixture was filtered to remove insoluble matter and the filtrate was concentrated by rotary evaporation at up to 40° C. bath temperature until all THF was removed. The resulting solid was collected by vacuum filtration and washed with water (1 L). The solid was then dissolved in a mixture of water (1.5 L) and THF (1.5 L) at room temperature. The pH was adjusted from approximately 5 to approximately 2-2.25 with concentrated HCl. The resulting mixture was stirred for 30 minutes, after which time the pH was confirmed in the range of 2-2.5. The biphasic mixture was concentrated by rotary evaporation at up to 40° C. bath temperature until the removal of THF ceased. The resulting solid was filtered, washed with water (2×1 L), and dried to afford 115 g (55.8% yield) of the desired product as a white solid. MP: 182-184° C.; MS (ESI−): m/z 289 (M−1); $^1$H NMR (300 MHz, DMSO-d$_6$) δ 12.90 (s, 1H), 12.38 (s, 1H), 9.39-9.37 (t, J=6.3 Hz, 1H), 8.55 (s, 1H), 7.80-7.67 (m, 2H), 7.59-7.52 (m, 1H), 7.34-7.27 (m, 1H), 4.02-3.99 (m, 2H), 3.51 (s, 1H).

The amide prodrugs of the disclosed HIF-2α stabilizer can be prepared by the process outlined in Scheme II and further described in Example 2 herein below.

Scheme II

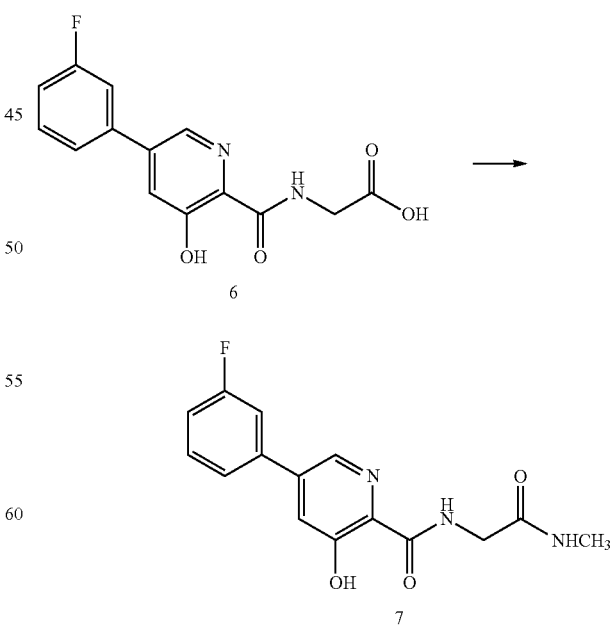

Reagents and conditions: (a) CH$_3$NH$_2$HCl, EDCI, HOBt, DIPEA, DMF; 0° C. to rt, 2 days

Example 2

5-(3-Fluorophenyl)-N-(2-methylamino-2-oxoethyl)-3-hydroxypyridin-2-yl amide (7)

Preparation of 5-(3-fluorophenyl)-N-(2-methylamino-2-oxoethyl)-3-hydroxypyridin-2-yl amide (7): To a solution of {[5-(3-fluorophenyl)-3-hydroxypyridine-2-carbonyl]-amino}acetic acid, 6, (2.9 g, 10 mmol) in DMF (50 mL) at room temperature under $N_2$ is added 1-(3-dimethylaminopropyl)-3-ethylcarbodiimide (EDCI) (2.33 g, 14.4 mmol), 1-hydroxybenzotriazole (HOBt) (1.35 g, 10 mmol) and diisopropylethylamine (DIPEA) (15.65 mL, 30 mmol). The reaction is stirred for 5 minutes then methylamine hydrochloride (0.9 g, 130 mmol) is added. After stirring for 2 days, the solvent is removed under reduced pressure and the residue partitioned between $CH_2Cl_2$ and $H_2O$. The organic layer is separated, washed with sat. NaCl, dried ($Na_2SO_4$), filtered and concentrated under reduced pressure. The crude product is purified over silica (MeOH:$CH_2Cl_2$ 1:99) to afford the desired compound.

The following describes a further process for preparing the disclosed HIF-2α stabilizer and prodrugs thereof. In Scheme III the process for preparing an example of an ester prodrug is outlined and described in Example 3.

Scheme III

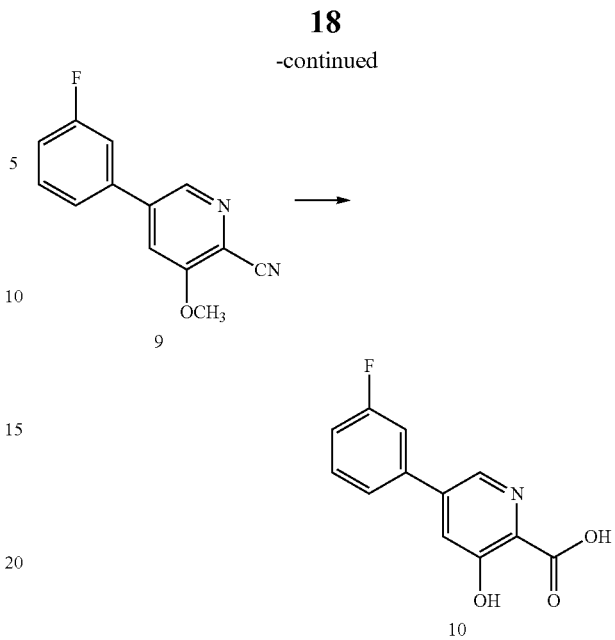

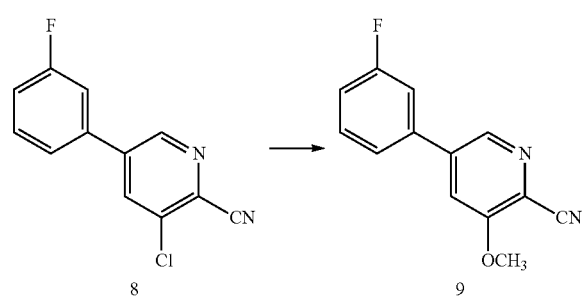

Reagents and conditions: (a) $K_2CO_3$, $PdCl_2(dppf)$, DMF, $H_2O$; 45° C., 18 hr.

Reagents and conditions: (b) NaOCH$_3$, CH$_3$OH; reflux, 20 hr.

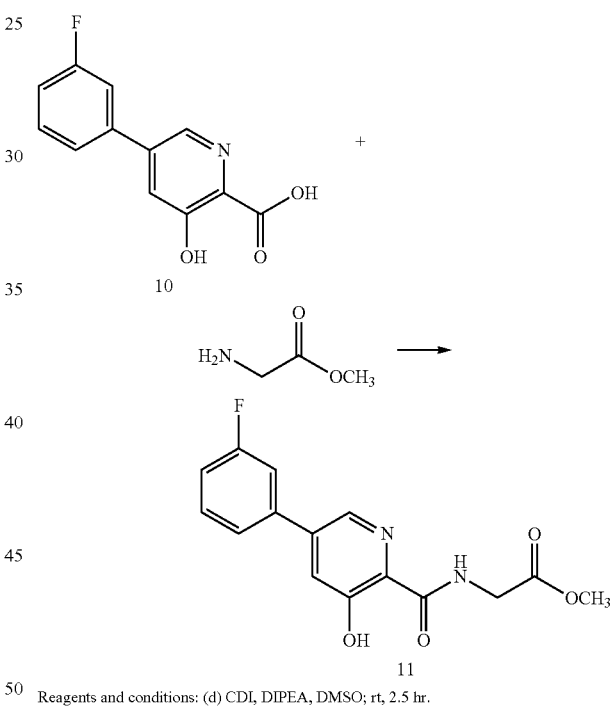

Reagents and conditions: (c) 48% HBr; reflux, 20 hr.

Reagents and conditions: (d) CDI, DIPEA, DMSO; rt, 2.5 hr.

Example 3

Methyl {[5-(3-fluorophenyl)-3-hydroxypyridin-2-carbonyl]amino}acetate (11)

Preparation of 5-(3-fluorophenyl)-3-chloro-2-cyanopyridine (8): To a 100 mL round bottom flask that is adapted for magnetic stirring and equipped with a nitrogen inlet is charged (3-fluorophenyl)boronic acid (4.48 g, 32 mmol), 3,5-dichloro-2-cyanopyridine (5.8 g, 34 mmol), $K_2CO_3$ (5.5 g, 40 mmol), [1,1'-bis(diphenyphosphino)ferrocene]dichloro-palladium(II) [PdCl$_2$(dppf)] (0.1 g, 0.13 mmol), dimethylformamide (50 mL) and water (5 mL). The reaction solution is agitated and heated to 45° C. and held at that temperature for 18 hours after which the completeness of the reaction can be determined by the absence of the starting material 3,5-dichloro-2-cyanopyridine via TLC using ethyl acetate/methanol (4:1) as the mobile phase and UV 435 nm to visualize any remaining starting material. The reaction solution is then cooled to room temperature and the contents partitioned between ethyl acetate (250 mL) and saturated aqueous NaCl (100 mL). The organic phase is isolated and washed a second time with saturated aqueous NaCl (100 mL). The organic phase is dried for 4 hours over MgSO$_4$, the MgSO$_4$ is removed by filtration and the solvent is removed under reduced pressure. The residue that remains is then slurried in methanol (50 mL) at room temperature for 20 hours. The resulting solid is collected by filtration and washed with cold methanol (50 mL) then hexanes (60 mL) and dried to afford desired product.

Preparation of 5-(3-fluorophenyl)-3-methoxy-2-cyanopyridine (9): To a 500 mL round bottom flask adapted for magnetic stirring and fitted with a reflux condenser and nitrogen inlet is charged 5-(3-fluorophenyl)-3-chloro-2-cyanopyridine, 8, (9.28 g, 40 mmol), sodium methoxide (13.8 mL, 60 mmol) and methanol (200 mL). With stirring, the reaction solution is heated to reflux for 20 hours. The reaction can be determined to be complete due to the disappearance of 5-(3-fluorophenyl)-3-chloro-2-cyanopyridine as measured by TLC analysis using hexane/ethyl acetate (6:3) as the mobile phase and UV 435 nm to visualize the reaction components. The reaction mixture is cooled to room temperature and combined with water (500 mL). The mixture is cooled to 0° C. to 5° C. and stirred for 3 hours. The resulting solid is collected by filtration and washed with water, then hexane. The resulting cake is then dried in vacuo at 40° C. to afford the desired product.

Preparation of 5-(3-fluorophenyl)-3-hydroxypyridine-2-carboxylic acid (10): To a 50 mL round bottom flask adapted for magnetic stirring and fitted with a reflux condenser is charged 5-(3-fluorophenyl)-3-methoxy-2-cyanopyridine, 9, (0.912 g, 4 mmol) and a 48% aqueous solution of HBr (10 mL). While being stirred, the reaction solution is heated to reflux for 20 hours. The reaction can be determined to be complete due to the disappearance of 5-(3-fluorophenyl)-3-methoxy-2-cyanopyridine as measured by TLC analysis using hexane/ethyl acetate (6:3) as the mobile phase and UV 435 nm to visualize the reaction components. The reaction is then cooled to 0° C. to 5° C. with stirring and the pH is adjusted to approximately 2 by the slow addition of 50% aqueous NaOH. Stirring is then continued at 0° C. to 5° C. for 3 hours. The resulting solid is collected by filtration and washed with water, then hexane. The resulting cake is dried in vacuo at 40° C. to afford the desired product.

Preparation of methyl {[5-(3-fluorophenyl)-3-hydroxypyridin-2-carbonyl]amino}-acetate (11): To a 50 mL round bottom flask adapted for magnetic stirring and fitted with a nitrogen inlet tube is charged 5-(3-fluorophenyl)-3-hydroxypyridine-2-carboxylic acid, 10, (0.932 gm, 4 mmol), N,N'-carbonyldiimidazole (CDI) (0.97 g, 6 mmol) and dimethyl sulfoxide (5 mL). The reaction mixture is stirred at 45° C. for about 1 hour then cooled to room temperature. Glycine methyl ester hydrochloride (1.15 g, 12 mmol) is added followed by the dropwise addition of diisopropylethylamine (3.2 mL, 19 mmol). The mixture is then stirred for 2.5 hours at room temperature after which water (70 mL) is added. The contents of the reaction flask is cooled to 0° C. to 5° C. and 1N HCl is added until the solution pH is approximately 2. The solution is extracted with dichloromethane (100 mL) and the organic layer dried over MgSO$_4$ for 16 hours. Silica gel (3 g) is added and the solution slurried for 2 hours after which the solids are removed by filtration. The filtrate is concentrated to dryness under reduced pressure and the resulting residue is slurried in methanol (10 mL) for two hours. The resulting solid is collected by filtration and washed with cold methanol (20 mL) then hexane and the resulting cake is dried to afford the desired product.

Ester prodrug methyl {[5-(3-fluorophenyl)-3-hydroxypyridin-2-yl]amino}acetate, 11, can be converted to the disclosed HIF-2α stabilizer, {[5-(3-Fluorophenyl)-3-hydroxypyridine-2-carbonyl]amino}acetic acid, 6, by the procedure outlined in Scheme I step (e) and described in Example 1.

Scheme IV herein below outlines and Example 4 describes a further non-limiting example of a procedure for an amide prodrug of the disclosed HIF-2α stabilizer.

Scheme IV

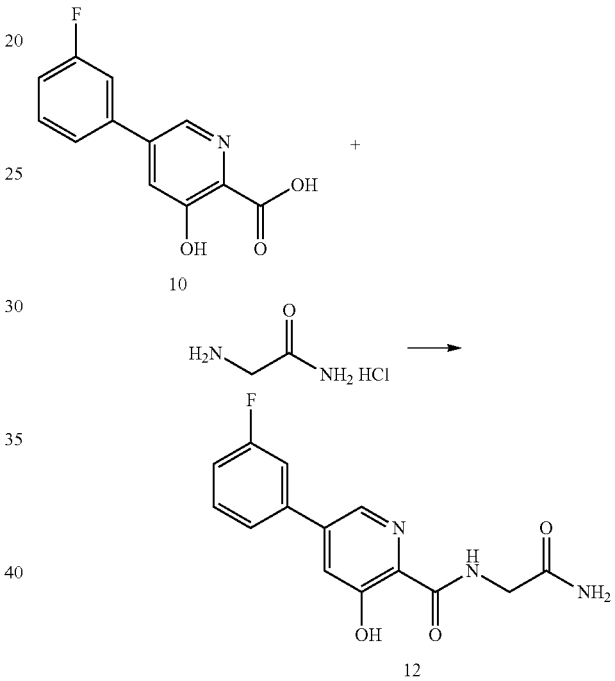

Reagents and conditions: (a) EDCI, HOBt, DIPEA, DMF; rt.

Example 4

5-(3-Fluorophenyl)-N-(2-amino-2-oxoethyl)-3-hydroxylpyridin-2-yl amide (12)

Preparation of 5-(3-fluorophenyl)-N-(2-amino-2-oxoethyl)-3-hydroxylpyridin-2-yl amide (6): To a solution of 5-(3-fluorophenyl)-3-hydroxypyridine-2-carboxylic acid, 10, (699 mg, 3 mmol) in DMF (20 mL) at room temperature under N$_2$ is added 1-(3-dimethyl-aminopropyl)-3-ethylcarbodiimide (EDCI) (0.925 g, 5.97 mmol) and 1-hydroxybenzo-triazole (HOBt) (0.806 g, 5.97 mmol). The resulting solution is stirred for 15 minutes then 2-aminoacetamide hydrochloride (0.66 g, 5.97 mmol) and diisopropylethylamine (1.56 ml, 8.96 mmol) are added. The reaction is monitored by TLC and when the reaction is complete the reaction mixture is concentrated under reduced pressure and H$_2$O added. The desired product can be isolated by normal work-up.

The present disclosure also includes pharmaceutically acceptable salts of the disclosed stabilizer. The following is a non-limiting example of the preparation of a pharmaceutically acceptable salt as depicted in Scheme V.

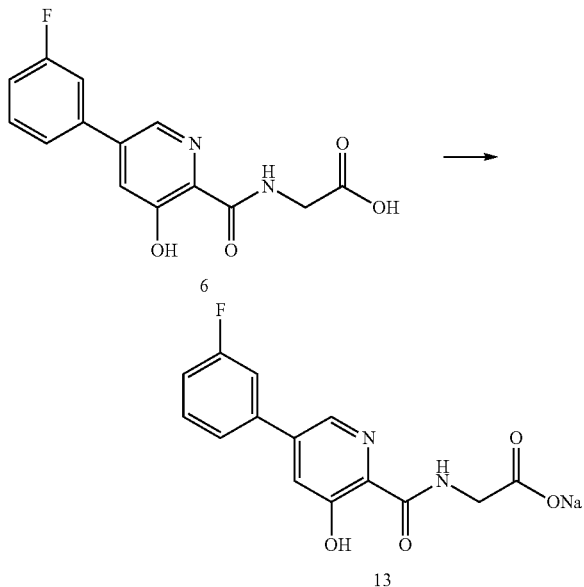

Scheme V

Example 5

Sodium {[5-(3-fluorophenyl)-3-hydroxypyridine-2-carbonyl]amino}acetate (13)

To a vial containing NaHCO$_3$ (41.09 mg) is added a solution of {[5-(3-fluoro-phenyl)-3-hydroxypyridine-2-carbonyl]-amino}acetic acid (6) in acetone (0.64 mL of a 400 mg sample in 5.12 mL). The solution is stirred and the desired product isolated by concentration in vacuo.

Methods

It is well known that cancer growth and metastasis is not exclusively controlled by the aberrant regulation of metastasis promoting or suppressing genes in cancer cells. The interaction between cancer cells and the stromal cells has been shown to promote cancer growth and metastasis. The macrophages found within tumors, referred to as tumor-associated macrophages (TAMs), are a pivotal member of stromal cells (See, Leek R D, Harris A L, "Tumour associated macrophages in breast cancer," *J Mamm Gland Biol Neoplasia* 7: 177-189, 2002 and Lewis C E, Murdoch C., "Macrophage responses to hypoxia: implications for tumor progression and anti-cancer therapies." *Am J Pathol* 167: 627-635, 2005). TAMs are derived from peripheral blood monocytes recruited into the tumor. Upon activation by cancer cells, the TAMs can release a diversity of factors inter alia, growth factors, proteolytic enzymes, cytokines, and inflammatory mediators. Many of these factors are key agents in promoting metastasis of cancer cells; in fact, extensive TAM infiltration has been shown to correlate with cancer metastasis and poor prognosis in a variety of human carcinomas. TAMs promote cancer metastasis through several mechanisms including tumor angiogenesis, tumor growth, and tumor cell migration and invasion. As such, control over the various factors released and/or stimulated by TAMs, i.e., VEGF is an important method for reducing, stopping, or preventing tumor growth and cancer cell metastasis.

Secretion of vascular endothelial growth factor (VEGF) by tumor-infiltrating macrophages in response to the hypoxic tumor microenvironment is well known to induce blood vessel formation (angiogenesis), which leads to increased tumor growth and metastasis. It has been previously demonstrated that, in addition to producing VEGF, mononuclear phagocytes stimulated with granulocyte-macrophage colony-stimulating factor (GM-CSF) under hypoxic conditions also secrete high levels of a soluble form of the VEGF receptor (sVEGFR-1), which neutralizes VEGF and inhibits biological activity (Eubank T D, et al., "GM-CSF induces expression of soluble VEGF receptor-1 from human monocytes and inhibits angiogenesis in mice," *Immunity,* 2004; 21(6): 8331-842). In addition, it was found that hypoxia-inducible factor-1 alpha (HIF-1α) controls macrophage production of VEGF, while hypoxia-inducible factor-2 alpha (HIF-2α) controls macrophage production of sVEGFR-1, thereby demonstrating opposing roles for the HIFs in the regulation of angiogenesis. Moreover, HIF-1α exhibits pro-angiogenic behavior via its effects on VEGF and HIF-2α exhibits anti-angiogenic behavior by inducing production of the endogenous VEGF inhibitor, sVEGFR-1 (Eubank T D, et al., "Opposing roles for HIF-1 {alpha} and HIF-2 {alpha} in the regulation of angiogenesis by mononuclear phagocytes," *Blood,* 2011; 117(1): 323-332). Therefore, there are specific and independent roles for HIF-1α and HIF-2α in the regulation of angiogenesis and tumor growth.

The hypoxia inducible factors HIF-1α and HIF-2α are constitutively transcribed; however, both are rapidly degraded by a process that begins with hydroxylation of key HIF proline amino acids. There are three known isoforms of the prolyl hydroxylase domain (PHD) proteins (i.e., 4-prolyl hydroxylase enzymes) each of which acts to degrade different HIF's. For example, PHD2 hydroxylates HIF-1α whereas PHD3 hydroxylates HIF-2α. Because stabilization of HIF-1α increases VEGF, inhibition of PHD2 increases angiogenesis. In contrast, stabilization of HIF-2α decreases VEGF via macrophage production of sVEGFR-1 and inhibition of PHD3 suppresses angiogenesis and provides a method for treating cancer. (Prolyl hydroxylation generates a binding site for a ubiquitin ligase complex containing the von Hippel-Lindau (VHL) tumor suppressor protein, which results in HIFα destruction. In addition, the HIFα transcriptional activation function is modulated further by asparagine hydroxylation by FIH (factor-inhibiting HIF), which affects recruitment of the coactivators p300 and CBP. As such, hydroxylation of HIF by PHD begins an irreversible process that depletes cellular levels of HIF.)

Disclosed herein are methods for affecting tumor growth by stabilizing HIF-2α. Without wishing to be limited by theory, {[5-(3-fluorophenyl)-3-hydroxypyridine-2-carbonyl]-amino}acetic acid stabilizes HIF-2α by inhibiting PHD3, thereby allowing greater quantities of the VEGF suppressor sVEGFR-1 to be secreted by macrophages and (and possibly other cells in the tumor inclusive of cancer cells and other stromal cells).

In addition to the known regulation of sVEGFR-1, the HIF-2α stabilizer, {[5-(3-fluorophenyl)-3-hydroxypyridine-2-carbonyl]-amino}acetic acid, unexpectedly downregulated VEGF in hypoxic embryonic fibroblasts (see FIG. 1). This effect was retained in embryonic fibroblasts lacking HIF-1α.

Disclosed herein are methods for affecting tumor growth by stabilizing HIF-2α. Without wishing to be limited by theory, {[5-(3-fluorophenyl)-3-hydroxypyridine-2-carbonyl]-amino}acetic acid stabilizes HIF-2α by inhibiting PHD3, thereby unexpectedly suppressing VEGF production in tumor cells (inclusive of cancer cells and stromal cells).

In recent years, the Warburg hypothesis has re-gained attention due to discoveries linking impaired mitochondrial function as well as impaired respiration to the growth, division and expansion of tumor cells. The body often kills damaged cells by apoptosis, a mechanism of self-destruction that involves mitochondria, but this mechanism may fail in cancer cells where the mitochondria are shut down. The reactivation of mitochondria in cancer cells could restart their apoptosis program. In addition to being simply a response to impaired respiration, ramping up glycolysis in tumor cells could also provide the carbon-containing building blocks required for cell replication.

In addition to downregulating VEGF the HIF-2α stabilizer {[5-(3-fluorophenyl)-3-hydroxypyridine-2-carbonyl]-amino}acetic acid unexpectedly down-regulated PGK a key glycolytic enzyme in hypoxic embryonic fibroblasts (see FIG. 2). This effect was retained in embryonic fibroblasts lacking HIF-1α.

Disclosed herein are methods for affecting tumor growth by stabilizing HIF-2α. Without wishing to be limited by theory, {[5-(3-fluorophenyl)-3-hydroxypyridine-2-carbonyl]-amino}acetic acid stabilizes HIF-2α by inhibiting PHD3, thereby unexpectedly suppressing PGK production in tumor cells.

The disclosed HIF-2α stabilizer and prodrugs thereof can be used to prevent, abate, minimize, control, and/or lessen tumor growth and/or tumor metastasis in humans and animals. The disclosed HIF-2α stabilizer and prodrugs thereof can also be used to slow the rate of primary tumor growth. The disclosed HIF-2α stabilizer and prodrugs thereof when administered to a subject in need of treatment can be used to stop the spread of cancer cells. As such, the HIF-2α stabilizer and prodrugs thereof disclosed herein can be administered as part of a combination therapy with one or more drugs or other pharmaceutical agents. When used as part of the combination therapy, the decrease in metastasis and reduction in primary tumor growth afforded by the disclosed HIF-2α stabilizer and prodrugs thereof allows for a more effective and efficient use of any pharmaceutical or drug therapy being used to treat the patient. In addition, control of metastasis by the disclosed HIF-2α stabilizer and prodrugs thereof affords the subject a greater ability to limit the disease in one location.

Figure 10:
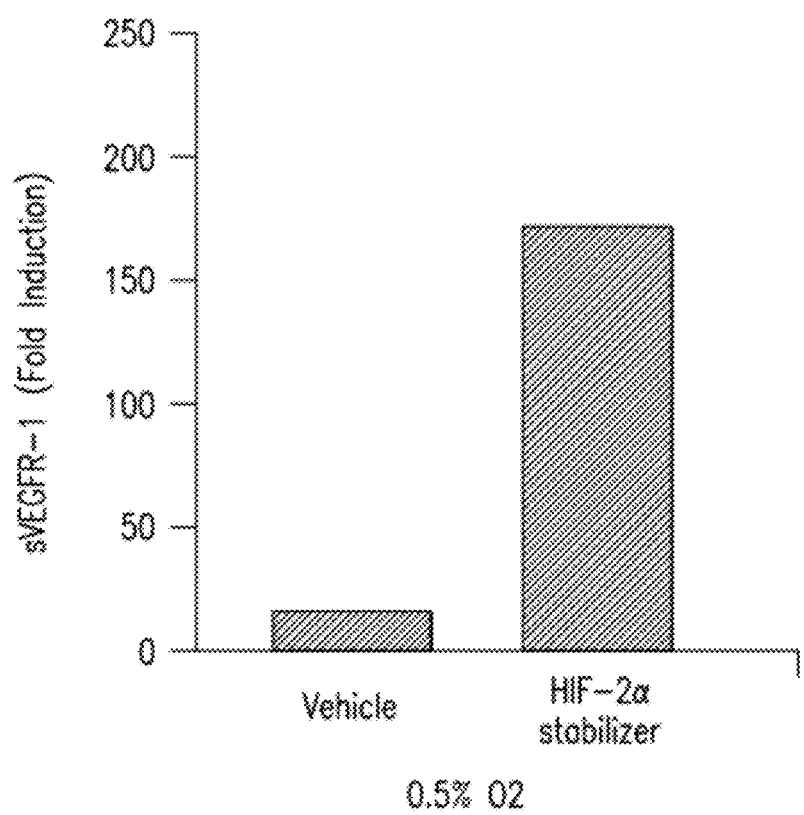
FIG. 10 depicts the induction of s-VEGFR-1 in human peripheral blood monocytes at 10 μM versus control (vehicle).

The disclosed compound, {[5-(3-fluorophenyl)-3-hydroxypyridine-2-carbonyl]-amino}acetic acid, salts thereof, and ester and amide prodrug have anti-tumorigenic properties in that the compounds:

1. Cause cells under hypoxic conditions to have a significant reduction in the amount of Vascular Endothelial Growth Factor (VEGF) that is present, thereby removing one factor that stimulates angiogenesis in the tumor microenvironment, and hence, reduces the ability of tumor cells to use angiogenesis as a means of providing nutrients for growth. This fact is evidenced in FIGS. 1A and 1B;

2. Causes cells under hypoxic conditions to display a significant reduction in the amount of phosphoglycerate kinase present in the cell, wherein tumor cells have been shown not to use oxidative phosphorylation as a source of energy, but instead glycolysis. This therefore removes or reduces the tumor cell's ability to produce energy for growth. This fact is evidenced in FIGS. 2A and 2B; and 3. Causes the stimulation of s-VEGFR1 (soluble VEGF) which is a competing receptor for VEGF and hence reduces the amount of VEGF that can stimulate angiogenesis. This fact is evidenced in FIG. 10.

As such, the disclosed compounds provide a three-pronged attack against tumor cells; overcoming PGK, and thus obviating a primary source of energy, reducing VEGF and thus providing for a reduced capacity of tumor cells to gain nutrients and blood supply via angiogenesis, and by increasing s-VEGF which further reduces the ability of tumors to induce angiogenesis.

Disclosed herein are methods for preventing metastasis of malignant tumors or other cancerous cells as well as to reduce the rate of tumor growth. The methods comprise administering an effective amount of one or more of the disclosed compounds to a subject diagnosed with a malignant tumor or cancerous cells or to a subject having a tumor or cancerous cells. For example, a method for treating a subject diagnosed with a malignant tumor or cancerous cells, comprising administering to the subject an effective amount of {[5-(3-fluorophenyl)-3-hydroxypyridine-2-carbonyl]amino}acetic acid. In another example, a method for treating a subject having a malignant tumor or cancerous cells, comprising administering to the subject an effective amount of {[5-(3-fluorophenyl)-3-hydroxypyridine-2-carbonyl]amino}acetic acid.

Disclosed herein is a method for stabilizing hypoxia inducible factor-2 alpha (HIF-2α), comprising administering to a subject an effective amount of the disclosed HIF-2α stabilizer and/or prodrugs thereof. For example, a method for stabilizing hypoxia inducible factor-2 alpha (HIF-2α), comprising administering to a subject an effective amount of {[5-(3-fluorophenyl)-3-hydroxypyridine-2-carbonyl]amino}acetic acid.

Further disclosed herein is a method for treating cancer, comprising administering to a subject an effective amount of the disclosed HIF-2α stabilizer and/or prodrugs thereof. For example, a method for treating cancer, comprising administering to a subject an effective amount of {[5-(3-fluorophenyl)-3-hydroxypyridine-2-carbonyl]amino}acetic acid.

Also disclosed herein is a method for decreasing tumor angiogenesis in a subject having cancer, comprising administering to a subject an effective amount of the disclosed HIF-2α stabilizer and/or prodrugs thereof. For example, a method or decreasing tumor angiogenesis in a subject having cancer, comprising administering to a subject an effective amount of {[5-(3-fluorophenyl)-3-hydroxypyridine-2-carbonyl]amino}acetic acid.

Yet further disclosed herein is a method for decreasing tumor angiogenesis in a subject diagnosed with cancer, comprising administering to a subject an effective amount of the disclosed HIF-2α stabilizer and/or prodrugs thereof. For example, a method for decreasing tumor angiogenesis in a subject diagnosed with cancer, comprising administering to a subject an effective amount of {[5-(3-fluorophenyl)-3-hydroxypyridine-2-carbonyl]amino}acetic acid.

Still further disclosed herein is a method for decreasing vascular endothelial growth factor (VEGF) in a cell in vitro, in vivo or ex vivo by inhibiting the binding of VEGF to VEGFRs, comprising administering to the cell an effective amount of the disclosed HIF-2α stabilizer and/or prodrugs thereof. In one embodiment, the cell is a cancer cell. In another embodiment, the cell is a human cell. In as still further embodiment, the cell is a human cancer cell. For example, a method for decreasing vascular endothelial growth factor (VEGF) in a cell in vitro, in vivo or ex vivo, comprising administering to the cell an effective amount of {[5-(3-fluorophenyl)-3-hydroxypyridine-2-carbonyl]amino}acetic acid.

Also further disclosed herein is a method for increasing secretion of soluble vascular endothelial growth factor receptor-1 (sVEGF-1) from a cell in vitro, in vivo or ex vivo, comprising administering to the cell an effective amount of the disclosed HIF-2α stabilizer and/or prodrugs thereof. In one embodiment, the cell is a tumor associated cell. In another embodiment, the cell is a human tumor associated cell. In as still further embodiment, the cell is a human cancer cell. For example, a method for increasing secretion of soluble vascular endothelial growth factor receptor-1 (sVEGF-1) from a cell in vitro, in vivo or ex vivo, comprising administering to the cell an effective amount of {[5-(3-fluorophenyl)-3-hydroxypyridine-2-carbonyl]amino}acetic acid.

Still yet further disclosed is a method for controlling tumor growth in a subject, comprising administering to the subject an effective amount of the disclosed HIF-2α stabilizer and/or a prodrug thereof.

Disclosed herein is the use of the disclosed HIF-2α stabilizer and/or a prodrug thereof for making a medicament for treating cancer. For example, the use of {[5-(3-fluorophenyl)-3-hydroxypyridine-2-carbonyl]amino}acetic acid for making a medicament for treating cancer.

Further disclosed herein is the use of the disclosed HIF-2α stabilizer and/or prodrugs thereof for making a medicament for preventing metastasis of malignant tumors or other cancerous cells and for slowing tumor growth. For example, the use of {[5-(3-fluorophenyl)-3-hydroxypyridine-2-carbonyl]amino}acetic acid for making a medicament for preventing metastasis of malignant tumors or other cancerous cells and for slowing tumor growth.

Disclosed herein is the use of the disclosed HIF-2α stabilizer and/or a prodrug thereof for treating cancer. For example, the use of {[5-(3-fluorophenyl)-3-hydroxypyridine-2-carbonyl]amino}acetic acid for treating cancer.

Further disclosed herein is the use of the disclosed HIF-2α stabilizer and/or a prodrug thereof for preventing metastasis of malignant tumors or other cancerous cells and for slowing tumor growth. For example, the use of {[5-(3-fluorophenyl)-3-hydroxypyridine-2-carbonyl]amino}acetic acid for preventing metastasis of malignant tumors or other cancerous cells and for slowing tumor growth.

Further still disclosed herein is the use of the disclosed HIF-2α stabilizer and/or a prodrug thereof for decreasing tumor angiogenesis. For example, the use of {[5-(3-fluorophenyl)-3-hydroxypyridine-2-carbonyl]amino}acetic acid for treating decreasing tumor angiogenesis.

Further still disclosed herein is the use of the disclosed HIF-2α stabilizer and/or a prodrug thereof for making a medicament for decreasing tumor angiogenesis. For example, the use of {[5-(3-fluorophenyl)-3-hydroxypyridine-2-carbonyl]amino}acetic acid for making a medicament for treating decreasing tumor angiogenesis.

Still yet further disclosed herein is a method for treating cancer, comprising administering to a subject an effective amount of the disclosed HIF-2α stabilizer and/or prodrugs thereof and an effective amount of one or more chemotherapeutic agents, wherein the disclosed HIF-2α stabilizer and/or prodrugs thereof and the one or more chemotherapeutic agents are administered in any order. For example, a method for treating cancer, comprising administering to a subject an effective amount of {[5-(3-fluorophenyl)-3-hydroxypyridine-2-carbonyl]amino}acetic acid and an effective amount of one or more chemotherapeutic agents. Non-limiting examples of chemotherapeutic agents include taxol, IL-2, gemcitabine, erlotinib, doxil, irinortecan, and bevacizumab.

Still also yet further disclosed herein is a method for preventing metastasis of cancer cells, comprising administering to a subject having cancer an effective amount of the disclosed HIF-2α stabilizer and/or prodrugs thereof and an effective amount of one or more chemotherapeutic agents, wherein the disclosed HIF-2α stabilizer and/or prodrugs thereof and the one or more chemotherapeutic agents are administered in any order. For example, a method for preventing metastasis of cancer cells, comprising administering to a subject having cancer an effective amount of {[5-(3-fluorophenyl)-3-hydroxypyridine-2-carbonyl]amino}acetic acid and an effective amount of one or more chemotherapeutic agents. Non-limiting examples of chemotherapeutic agents include taxol, IL-2, gemcitabine, erlotinib, doxil, irinortecan, and bevacizumab.

Also still yet further disclosed herein is a method for treating a subject diagnosed with cancer, comprising administering to a subject diagnosed with cancer an effective amount of the disclosed HIF-2α stabilizer and/or prodrugs thereof and an effective amount of one or more chemotherapeutic agents, wherein the disclosed HIF-2α stabilizer and/or prodrugs thereof and the one or more chemotherapeutic agents are administered in any order. For example, a method for treating a subject diagnosed with cancer, comprising administering to a subject diagnosed with cancer an effective amount of {[5-(3-fluorophenyl)-3-hydroxypyridine-2-carbonyl]amino}acetic acid and an effective amount of one or more chemotherapeutic agents. Non-limiting examples of chemotherapeutic agents include taxol, IL-2, gemcitabine, erlotinib, doxil, irinortecan, and bevacizumab. The following are non-limiting examples of cancers that can be treated by the disclosed methods and compositions: Acute Lymphoblastic; Acute Myeloid Leukemia; Adrenocortical Carcinoma; Adrenocortical Carcinoma, Childhood; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Central Nervous System Embryonal Tumors; Cerebellar Astrocytoma; Cerebral Astrocytoma/Malignant Glioma; Craniopharyngioma; Ependymoblastoma; Ependymoma; Medulloblastoma; Medulloepithelioma; Pineal Parenchymal Tumors of Intermediate Differentiation; Supratentorial Primitive Neuroectodermal Tumors and Pineoblastoma; Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma; Cerebral Astrocytoma/Malignant Glioma, Childhood; Cervical Cancer; Chordoma, Childhood; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer; Histiocytosis, Langerhans Cell; Hodgkin Lymphoma; Hypopharyngeal Cancer; Hypothalamic and Visual Pathway Glioma; Intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macroglobulinemia, Waldenstrom; Malignant Fibrous Histiocytoma of Bone and Osteosarcoma; Medulloblastoma; Melanoma; Melanoma, Intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis Fungoides; Myelodysplastic Syndromes; Myelodysplastic/-Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Pineal Parenchymal Tumors of Intermediate Differentiation; Pineoblastoma and Supratentorial Primitive Neuroectodermal Tumors; Pituitary Tumor; Plasma Cell Neoplasm/Multiple Myeloma; Pleuropulmonary Blastoma; Primary Central Nervous System Lymphoma; Prostate Cancer; Rectal Cancer; Renal Cell (Kidney) Cancer; Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sezary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenström Macroglobulinemia; and Wilms Tumor.

Also disclosed herein are methods for treating cancer, comprising administering to a subject an effective amount of a compound of the formula:

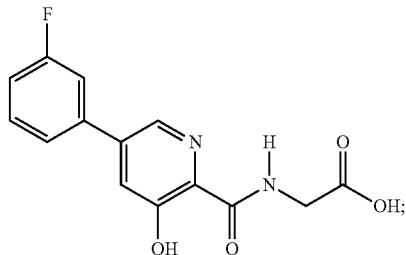 [SMILES: O=C(O)CNC(=O)c1ncc(-c2cccc(F)c2)cc1O]

or a pharmaceutically acceptable salt thereof.

The cancer can be any cancer described herein, including VEGF-dependent cancers. Because oxygen diffusion distance is approximately 150 nm, cells that comprise a solid tumor that grows beyond 2 mm$^3$ cannot proliferate without access to nearby vasculature to exchange oxygen and waste. In this instance, low oxygen stabilizes HIF-1α in the tumor cells and produces vascular endothelial growth factor (VEGF), which is a proliferating factor for endothelial cells in which blood vessels are comprised. Because VEGF is the key regulator of angiogenesis, the sequestration of VEGF by the soluble form of VEGF receptor-1 (sVEGFR-1) regulates angiogenesis. The inhibition of prolyl hydroxylase 3 (PHD3) by one or more of the compounds disclosed herein stabilizes HIF-2α. While tumor cells themselves do not produce sVEGFR-1, the compounds disclosed herein can increase the production of sVEGFR-1 from the monocytes and macrophages which arrive at the tumors in response to inflammatory signals. Thus, any tumors that rely on VEGF to proliferate are potential targets for the compounds disclosed herein because their activity can, in part, increase sVEGFR-1 production.

Compositions

Disclosed herein are compositions which can be used to treat cancer in a subject, treat cancer in a subject diagnosed with cancer, to prevent tumor growth in a subject, to prevent metastasis of cancer cells in a subject, the compositions comprising an effective amount of one or more of the compounds disclosed herein. Further disclosed herein are compositions that can be used to treat tumors in a human or other mammal.

One aspect relates to a composition comprising:
  a) an effective amount of one or more the disclosed HIF-2α stabilizer and/or prodrugs thereof; and
  b) one or more pharmaceutically acceptable ingredients.
Another aspect relates a composition comprising:
  a) an effective amount of one or more the disclosed HIF-2α stabilizer and/or prodrugs thereof; and
  b) an effective amount of one or more additional chemotherapeutic agent;
  wherein the disclosed compounds and the one or more additional chemotherapeutic agent can be administered together or in any order.
One embodiment relates to a composition comprising:
  a) an effective amount of one or more the disclosed HIF-2α stabilizer and/or prodrugs thereof; and
  b) an effective amount of taxol;
  wherein the disclosed compounds and taxol can be administered together or in any order.
Another embodiment relates to a composition comprising:
  a) an effective amount of one or more the disclosed HIF-2α stabilizer and/or prodrugs thereof; and
  b) an effective amount of gemcitabine;
  wherein the disclosed compounds and gemcitabine can be administered together or in any order.
A further embodiment relate to a composition comprising:
  a) an effective amount of one or more the disclosed HIF-2α stabilizer and/or prodrugs thereof; and
  b) an effective amount of erlotinib;
  wherein the disclosed compounds and erlotinib can be administered together or in any order.
A yet further embodiment relate to a composition comprising:
  a) an effective amount of one or more the disclosed HIF-2α stabilizer and/or prodrugs thereof; and
  b) an effective amount of doxil;
  wherein the disclosed compounds and doxil can be administered together or in any order.

A still further embodiment relate to a composition comprising:
a) an effective amount of one or more the disclosed HIF-2α stabilizer and/or prodrugs thereof; and
b) an effective amount of irinortecan;
wherein the disclosed compounds and irinortecan can be administered together or in any order.

A still yet further embodiment relate to a composition comprising:
a) an effective amount of one or more the disclosed HIF-2α stabilizer and/or prodrugs thereof; and
b) an effective amount of bevacizumab;
wherein the disclosed compounds and bevacizumab can be administered together or in any order.

A "chemotherapeutic agent" or "chemotherapeutic compound" is a chemical compound useful in the treatment of cancer. Chemotherapeutic cancer agents that can be used in combination with those disclosed herein include, but are not limited to, mitotic inhibitors (vinca alkaloids). These include vincristine, vinblastine, vindesine and Navelbine™ (vinorelbine-5'-noranhydroblastine). In yet other embodiments, chemotherapeutic cancer agents include topoisomerase I inhibitors, such as camptothecin compounds. As used herein, "camptothecin compounds" include Camptosar™ (irinotecan HCL), Hycamtin™ (topotecan HCL) and other compounds derived from camptothecin and its analogues. Another category of chemotherapeutic cancer agents that may be used in the methods and compositions of the present disclosure are podophyllotoxin derivatives, such as etoposide, teniposide and mitopodozide. The present disclosure further encompasses other chemotherapeutic cancer agents known as alkylating agents, which alkylate the genetic material in tumor cells. These include without limitation cisplatin, cyclophosphamide, nitrogen mustard, trimethylene thiophosphoramide, carmustine, busulfan, chlorambucil, belustine, uracil mustard, chlomaphazin, and dacarbazine. The present disclosure encompasses antimetabolites as chemotherapeutic agents. Examples of these types of agents include cytosine arabinoside, fluorouracil, methotrexate, mercaptopurine, azathioprime, and procarbazine. An additional category of chemotherapeutic cancer agents that may be used in the methods and compositions of the present disclosure include antibiotics. Examples include without limitation doxorubicin, bleomycin, dactinomycin, daunorubicin, mithramycin, mitomycin, mytomycin C, and daunomycin. There are numerous liposomal formulations commercially available for these compounds. The present disclosure further encompasses other chemotherapeutic cancer agents including without limitation anti-tumor antibodies, dacarbazine, azacytidine, amsacrine, melphalan, ifosfamide and mitoxantrone.

The disclosed compounds herein can be administered alone or in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cisplatin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the present disclosure include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including α and β) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the disclosed compounds include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin;

teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is 5-fluorouracil, taxol, or leucovorin.

Procedures

Otto Warburg (Warburg O. "On the origin of cancer cells," Science 123 (3191): 309-14 (1956)) first observed that most cancer cells produce energy by using anaerobic glycolysis rather than the more energy efficient aerobic conditions of normal cells. Xu has reported (Xu R-H et al., "Inhibition of Glycolysis in Cancer Cells: A Novel Strategy to Overcome Drug Resistance Associated with Mitochondrial Respiratory Defect and Hypoxia." Cancer Res. 65:(2), 613-621 (2005)) that hypoxia is an important factor that contributes to the "Warburg Effect" allowing cancer cells to grow and form tumor masses that outpace the normal generation of new vasculature.

This rapid expansion of tumors leaves the cancerous cells in a microenvironment with limited blood supply, and, thus, a limited ability to grow using aerobic conditions. In order to maintain a sufficient energy source, tumor cells maintain hypoxic conditions in their microenvironment and thereby use the resulting increased glycolytic activity as a means for energy production, as well as a method for stimulating angiogenesis. Vander Heiden (Van Heiden, M. G., et al., "Evidence for an Alternative Glycolytic Pathway in Rapidly Proliferating Cells," Science, 329, 1492-1499 (2010)) reported that proliferating cells, which includes cancer cells, "primarily metabolize glucose by glycolysis, whereas most normal cells completely catabolize glucose by oxidative phosphorylation."

Phosphoglycerate kinase is a transferase enzyme that in one of the final steps of glycolysis serves to a transfer a phosphate group to ADP thereby forming ATP which is the ubiquitous source of metabolic energy. Without wishing to be limited by theory, decreasing the concentration of the enzyme phosphoglycerate kinase in hypoxic cells would provide a method of making the anaerobic glycolysis pathway unavailable to proliferating cells, i.e., cancer cells as an energy source. Further without wishing to be limited by theory, by inhibiting or reducing the hypoxic environment found in tumor cells, the amount of vascular endothelial growth factor (VEGF) which is produced in response to the hypoxic microenvironment is reduced thereby having the effect of decreasing the formation of new vasculature that would aid in cancer cell proliferation.

Without wishing to be limited by theory, anaplasia is a characteristic of cancer cells. Because cancer cells remain in a highly energized metabolic microenvironment, i.e., hypoxic environment, cancer cells lack the ability to enter a more quiescent stage whereby the cells can become mature, for example, to begin to differentiate in the manner of normal cells. Moreover, suppressing PGK concentrations in the tumor mass microenvironment can serve as a method of reducing or eliminating the conditions present in the cancer cell induced hypoxic environment resulting in slowing or stopping tumor growth.

Soluble VEGF receptor-1 (sVEGFR1) is a truncated approximately 110-kDa splice variant of the 180-kDa membrane-spanning VEGFR1. As reported by Wu (Wu F. T. H et al., "A systems biology perspective on sVEGFR1: its biological function, pathogenic role & therapeutic use," J. Cell Mol Med. 2010 Mar. 14(3): 528-552) the anti-angiogenic effects have not been well-elucidated, but are believed to include: (1) sequestration of VEGF ligands, much like VEGFR1 does, and effectively reducing VEGF-mediated activation of pro-angiogenic receptors; and (2) heterodimerization with full-length VEGFR monomers to render the receptor dimer inactive, since sVEGFR1 lacks the intracellular tyrosine kinase domain needed to transphosphorylate its full-length partner. The precise molecular mechanisms by which sVEGFR1 exerts inhibitory effects on VEGF-dependent signaling are unclear. Nevertheless, two mechanisms have been proposed: (1) direct ligand trapping of VEGF family members (including VEGF-A and P1GF), i.e., lowering the effective concentrations of free VEGF available for receptor activation; and (2) heterodimerization with surface VEGFRs to form dominant-negative complexes, i.e., lowering the effective density of unoccupied VEGFR available for ligand activation.

Without being limited by theory, stabilization of HIF-2α by the disclosed stabilizer results in an increased concentration of soluble vascular endothelial growth factor (sVEGFR-1) which results in a reduced concentration of VEGF. FIG. 1A depicts the reduction in mRNA expression of VEGF in wild type murine embryonic fibroblasts under normoxia (21% $O_2$) [Bar A, black] and wild type murine embryonic fibroblasts under hypoxic conditions (1% $O_2$) [Bar C, light gray] at various concentrations of HIF-2α stabilizer, {[5-(3-fluorophenyl)-3-hydroxypyridine-2-carbonyl]-amino}acetic acid. Under hypoxic conditions, there is a dramatic reduction in VEGF mRNA at 1, 10 and 100 μM concentrations [Bar D, lightest gray] vs. hypoxia control [Bar C].

FIG. 1B depicts the reduction in mRNA expression of VEGF in fibroblasts having deletion of HIF1-α, i.e., HIF-1α$^{-/-}$ fibroblasts under normoxia (21% $O_2$) [Bar A, black] and fibroblasts having deletion of HIF1-α, i.e., HIF-1α$^{-/-}$ fibroblasts under hypoxic conditions (1% $O_2$) [Bar C, light gray] at various concentrations of HIF-2α stabilizer, {[5-(3-fluorophenyl)-3-hydroxypyridine-2-carbonyl]-amino}acetic acid. Under hypoxic conditions, there is a dramatic reduction in VEGF mRNA at 1, 10 and 100 μM concentrations [Bar D, lightest gray] vs. hypoxia control [Bar C].

FIG. 2A depicts the reduction in mRNA expression of phosphoglycerate kinase PGK) in wild type murine embryonic fibroblasts under normoxia (21% $O_2$) [Bar A, black] and wild type murine embryonic fibroblasts under hypoxic conditions (1% $O_2$) [Bar C, light gray] at various concentrations of HIF-2α stabilizer, {[5-(3-fluorophenyl)-3-hydroxypyridine-2-carbonyl]-amino}acetic acid. Under hypoxic conditions, there is a dramatic reduction in PGK mRNA at 1, 10 and 100 μM concentrations [Bar D, lightest gray] vs. hypoxia control [Bar C].

FIG. 2B depicts the reduction in mRNA expression of phosphoglycerate kinase (PGK) in fibroblasts having deletion of HIF1-α, i.e., HIF-1α$^{-/-}$ fibroblasts under normoxia (21% $O_2$) [Bar A, black] and fibroblasts having deletion of HIF1-α, i.e., HIF-1α$^{-/-}$ fibroblasts under hypoxic conditions (1% $O_2$) [Bar C, light gray] at various concentrations of HIF-2α stabilizer, {[5-(3-fluorophenyl)-3-hydroxypyridine-2-carbonyl]-amino}acetic acid. Under hypoxic conditions, there is a dramatic reduction in PGK mRNA at 1, 10 and 100 μM concentrations [Bar D, lightest gray] vs. hypoxia control [Bar C].

The effectiveness of the disclosed HIF-2α stabilizer as a treatment for melanoma was studied.

Quantitative PCR Analysis of Gene Expression

Total RNA was isolated from tissues and cells by using TRIzol™ Reagent (Invitrogen) and the RNeasy kit (Qiagen), respectively. 1 μg RNA was used for reverse transcription using SuperScript II First-Strand Synthersis System (Invitrogen). cDNA's were amplified in a SYR Green or TaqMan Universal Master Mix (Applied Biosystems). Quantitative PCR (qPCR) was performed on ABI Prism 7700 sequence detection system. PCR conditions are: 10 min at 95° C., 40 cycles of 15 seconds at 95° C. and 1 minute at 60° C. The relative amount of mRNA was calculated after normalization to β-actin.

Cell Culture, Immortalization of Fibroblasts

Cells were cultured in DMEM (#11965-092, Invitrogen) supplemented with 10% fetal bovine serum (Invitrogen), 100 U/mL penicillin and 100 mg/mL streptomycin. For glucose deprivation, DMEM without glucose (#11966-025, Invitrogen) was used.

Mouse embryonic fibroblasts (MEFs) were isolated from E12.5 embryos and immortalized by stable transfection with SV40 large T antigen.

Murine Melanoma Tumor Model.

Mice were injected with $1 \times 10^5$ B16F10 murine melanoma cells murine subcutaneously on the left flank. Once tumors become palpable (approximately 5 days), mice were randomly allocated to receive treatment with either: 20% polyethylene glycol (PEG) in 5% dextran (vehicle control for the disclosed HIF-2α stabilizer) and PBS (vehicle control for GM-CSF), 20% PEG and GM-CSF (100 ng per mouse in a 50 μL volume), the disclosed HIF-2α stabilizer (17.5 mg/kg in a 100 μL volume) and PBS, or the disclosed HIF-2α stabilizer and GM-CSF (same doses). The PBS and GM-CSF were administered intratumorally, while the 20% PEG and the disclosed HIF-2α stabilizer were administered intraperitoneally. Mice were treated 3 times per week until tumors reached a size of 20 mm in any dimension (approximately 2.5 weeks), at which point mice were euthanized, in accordance with institutional policy. Tumor diameters were measured 3 times per week with calipers, and tumor volumes were calculated as follows: Tumor volume=$0.5 \times [$(large diameter)$\times$(small diameter)$^2]$.

Evaluation of Lung Metastases

Lung metastases were evaluated by detection of mRNA for melanocyte-specific proteins within the lungs of tumor-bearing mice. B16F10 tumor-bearing mice were treated with GM-CSF and/or the disclosed HIF-2α stabilizer, as depicted in FIG. 3. At the time of sacrifice, lungs were excised and flash-frozen in liquid nitrogen. Frozen lungs were homogenized in liquid nitrogen and the pulverized material was dissolved in TRIzol™ reagent (Invitrogen). RNA was extracted in chloroform and purified using the RNeasy Minikit (Qiagen). cDNA was generated from 1 μg of RNA using the Superscript First Strand Synthesis System (Invitrogen) and used for real-time PCR using SYBR Green PCR Master-Mix (Applied Biosciences) according to the manufacturers' instructions. The melanocyte-specific Pmel17 was detected by nested PCR using a modification of the protocol described by Tsukamoto et al. For the initial reaction, 30 cycles of PCR were carried out (95° C. for 1 minute, 58° C. for 1 min, 72° C. for 1 min) in a 20 μL reaction volume containing 2 μL of cDNA. For reamplification with the nested primers, 1 μL of the first reaction product was amplified in a 20 μL reaction volume for a further 30 cycles. Data were analyzed according to the comparative threshold method and normalized against the GAPDH internal control transcript. Results are semi-quantitative and represent the fold difference in transcript levels in vehicle-treated control mice as compared with levels in mice treated with the disclosed HIF-2α stabilizer and/or GM-CSF.

Murine Breast Cancer Model

PyMT transgenic mice, in which the polyoma middle T antigen is expressed from the murine mammary tumor virus (MMTV) promoter, have been previously described (Lin EY, *Am J Pathol,* 2003 included herein by reference in its entirety). These mice spontaneously develop carcinoma of the mammary epithelium in all 10 mammary glands. An immortalized cell line derived from a late-stage tumor from a C57BL/6 PyMT transgenic mouse was utilized. $5 \times 10^5$ C57BL/6 PyMT tumor cells were injected orthotopically into the #4 mammary fat pad of wildtype C57BL/6 mice. Once tumors became palpable (approximately 3 weeks), mice were randomized to receive treatment with either vehicle control (20% PEG in 5% dextran) or 12 or 17.5 mg/kg of the disclosed HIF-2α stabilizer. Mice were treated 3 times per week and tumor volumes were calculated as described herein above.

FIG. 3 shows the results of this study for the high dose (17 mg/kg) of the HIF-2α stabilizer. These data indicate that the disclosed HIF-2α stabilizer reduces tumor growth alone (Δ) and is comparable to the reduction in tumor volume seen when animals are treated with GM-CSF alone (■). In addition, the reduction in tumor growth is additive when the disclosed HIF-2α stabilizer is used in combination with GM-CSF (X). These results are compared to control animals (♦) which only received the dosing vehicle phosphate buffered saline (PBS).

Figure 4:
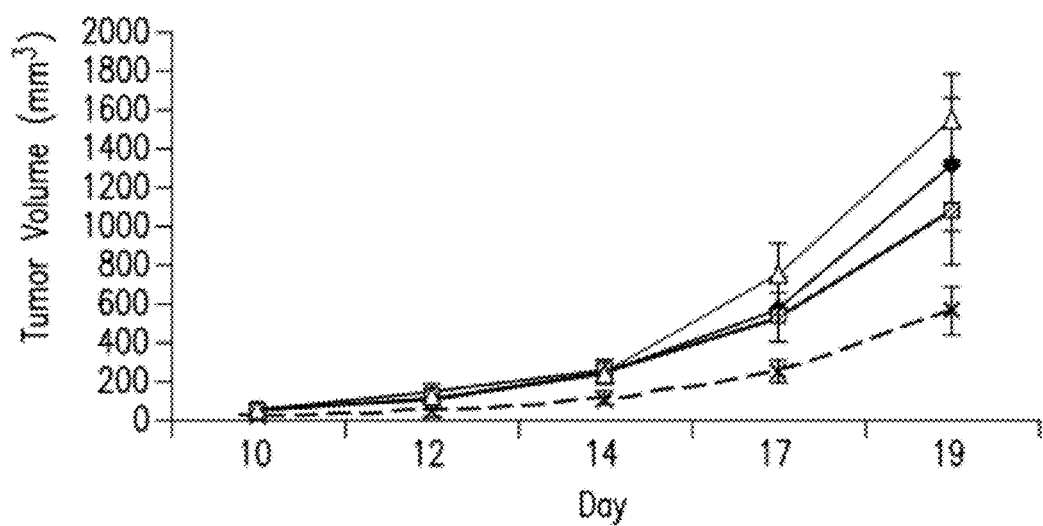
FIG. 4 depicts a comparison of GM-CSF delivery via intraperitoneal (I.P.) vs. intratumor (I.T.) in evaluating the effectiveness of delivery mode in reducing tumor volume. The disclosed HIF-2α stabilizer was delivered I.P. in all cases. The data depicted by (Δ) represents the disclosed HIF-2α stabilizer in combination with GM-CSF, both delivered I.P., data depicted by (♦) represents GM-CSF plus vehicle, both delivered I.P., data depicted by (■) represents GM-CSF delivered I.T. plus vehicle delivered I.P., and data depicted by (x) represent the disclosed HIF-2α stabilizer delivered I.P. in combination with GM-CSF delivered I.T.

This study was repeated comparing the dosing protocols, i.e., whether dosing was done via intraperitoneal (I.P.) or via intratumor (I.T.) injection. No control group was used for this repeated study. FIG. 4 shows the results of this study for the high dose (17 mg/kg) of the HIF-2α stabilizer. These data indicate that injections I.T. provide greater tumor volume reduction than injections I.P. For example, there was a greater reduction of tumor volume when GM-CSF was administered I.T. (♦) vs. administration I.P. (Δ). These results were confirmed for treatments constituting the disclosed HIF-2α stabilizer and GM-CSF when administered I.T. (x) vs. administration I.P. (■).

Figure 5:
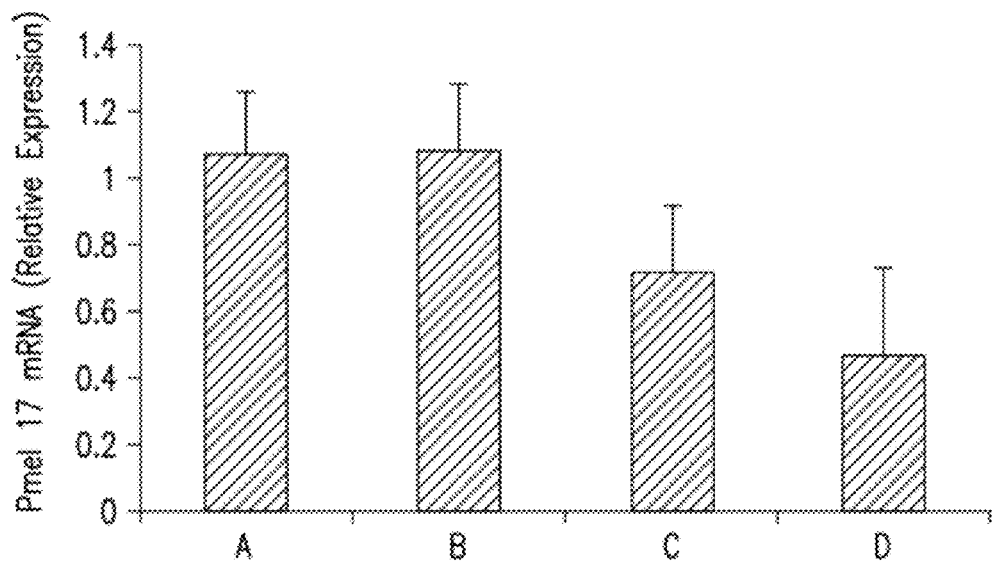
FIG. 5 depicts the amount of relative metastasis to the lung as determined using Pmel17 mRNA expression for the methods of injection depicted in FIG. 3 wherein the disclosed HIF-2α stabilizer was administered IP and the GM-CSF was administered IT. Group A is the vehicle control for both the disclosed HIF-2α stabilizer and GM-CSF. Group B represents GM-CSF plus 20% PEG in 5% dextran (vehicle for administration of the disclosed HIF-2α stabilizer). Group C represents the disclosed HIF-2α stabilizer plus PBS (vehicle for administration of GM-CSF). Group D represents the disclosed HIF-2α stabilizer and GM-CSF. The disclosed HIF-2α stabilizer was delivered in its vehicle (20% PEG in 5% dextran) and administered I.P. and GM-CSF was delivered in its vehicle (PBS) and administered I.T. Note that only the groups with the disclosed HIF-2α stabilizer showed reduced metastasis as measured by Pmel 17 mRNA expression.

FIG. 5 depicts the amount of relative metastasis to the lung as determined using Pmel17 mRNA expression for the methods of injection depicted in FIG. 3 wherein the disclosed HIF-2α stabilizer was administered IP and the GM-CSF was administered I.T. Group A is the vehicle control for both the disclosed HIF-2α stabilizer and GM-CSF. Group B represents GM-CSF plus 20% PEG in 5% dextran (vehicle for administration of the disclosed HIF-2α stabilizer). Group C represents the disclosed HIF-2α stabilizer plus PBS (vehicle for administration of GM-CSF). Group D represents the disclosed HIF-2α stabilizer and GM-CSF. The disclosed HIF-2α stabilizer was delivered in its vehicle (20% PEG in 5% dextran) and administered I.P. and GM-CSF was delivered in its vehicle (PBS) and administered I.T. Note that only the groups with the disclosed HIF-2α stabilizer showed reduced metastasis as measured by Pmel17 mRNA expression.

Figure 6:
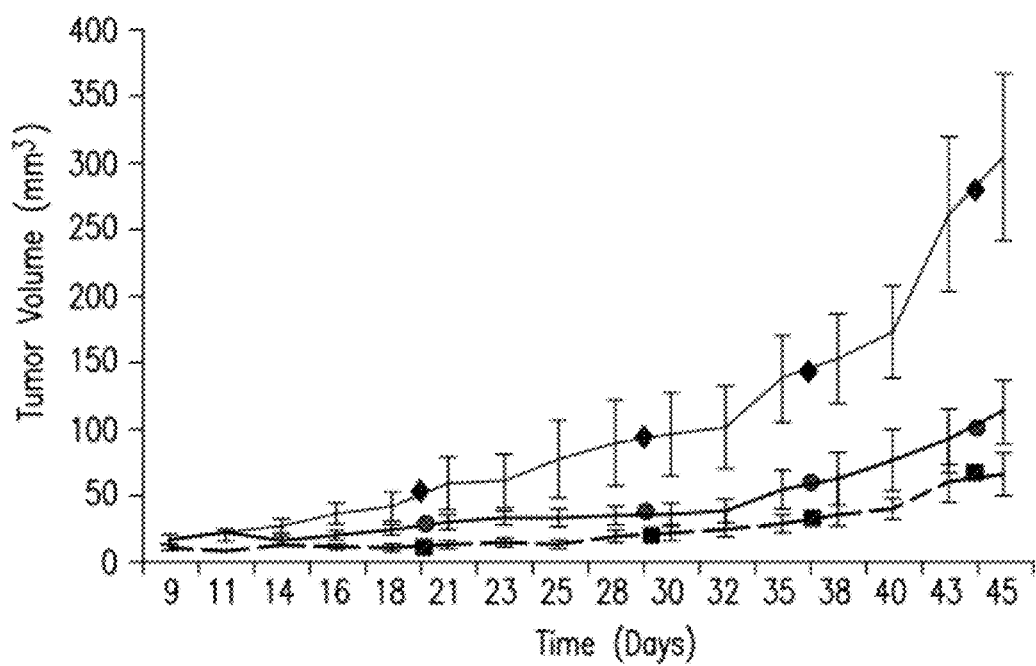
FIG. 6 depicts the reduction in tumor volume for C57BL/6 mice orthotopically injected with cells from MMTV-PyMT transgenic mice into a single mammary gland. Animals are treated three times a week with vehicle (♦), 12 mg/kg of the disclosed HIF-2α stabilizer (■), or 17.5 g/kg of the disclosed HIF-2α stabilizer (●).

FIG. 6 depicts the reduction in tumor volume for C57BL/6 mice orthotopically injected with cells from MMTV-PyMT transgenic mice into a single mammary gland. Animals are treated three times a week with vehicle (♦), 12 mg/kg of the disclosed HIF-2α stabilizer (■), or 17.5 g/kg of the disclosed HIF-2α stabilizer (●).

Human Ovarian Xenograft Study

Reagents and Test Compound

The compound tested, {[5-(3-fluorophenyl)-3-hydroxypyridine-2-carbonyl]-amino}acetic acid, was formulated in a 0.25% hydroxypropyl methyl cellulose/0.1% Tween™ 80 solution in reverse osmosis deionized water. The test compound was reconstituted at concentrations of 1.8 and 3.6 mg/ml as instructed on each vial to deliver doses of 18 and 36 mg/kg, respectively, at a 10 mg/kg dose volume. Solutions of the test compound were prepared weekly and stored at 4° C. protected from light. All formulations were removed from the refrigerator and stirred for 30 minutes before dosing, and continuously stirred during dosing.

The vehicle control was prepared by making a solution of 0.25% hydroxypropyl methyl cellulose/0.1% Tween™ 80 solution in reverse osmosis deionized water.

Cell Culture

A2780/CP ovarian tumor cell line was received from Sigma-Aldrich (St. Louis, Mo.). Cultures were maintained in RPMI 1640 (Hyclone, Logan, Utah), supplemented with 10% fetal bovine serum, and housed in a 5% $CO_2$ atmosphere. The cultures were expanded in tissue culture flasks at a 1:3 split ratio until a sufficient yield of cells was achieved.

Animals

Female athymic nude mice were supplied by Harlan (Indianapolis, Ind.). Mice were received at four to five weeks of age, 12-15 grams in weight, and were acclimated for seven days prior to handling. The mice were housed in microisolator cages and maintained under specific pathogen-free conditions. The mice were fed Tekland Global Diet™ 2920x irradiated laboratory animal diet (Harlan, Indianapolis, Ind.) and autoclaved water was freely available.

A2780/CP Ovarian Tumor Xenograft Model

Sixty female mice were inoculated subcutaneously in the right flank with 0.1 ml of a 50% RPMI/50% Matrigel™ (BD Biosciences, Bedford, Mass.) mixture containing a suspension of A2780/CP tumor cells (approximately $1.0 \times 10^7$ cells/mouse).

Three days following inoculation, tumors were measured using calipers and tumor weight was calculated using the animal study management software. Thirty mice with tumor sizes of 80.4-170.6 mg were randomized into three groups of ten mice (Groups 1-3) by random equilibration. Body weights were recorded when the mice were randomized and were taken twice per week thereafter in conjunction with tumor measurements.

Animals were treated until the study endpoint. Group I received only vehicle (control). Group II was given doses of 1.8 mg/mL {[5-(3-fluorophenyl)-3-hydroxypyridine-2-carbonyl]-amino}acetic acid while Group III was given doses of 3.6 mg/mL {[5-(3-fluorophenyl)-3-hydroxypyridine-2-carbonyl]-amino}acetic acid. All doses were given via oral administration (PO). The administered volume of each dose was approximately 1 mL/100 g body weight of animal.

Tumor mass (mg) was determined using the formula:

$$Mass = \frac{a \times b^2}{2}$$

where "a" is the largest diameter and "b" is the smallest diameter. Measurements were made using calipers. The mean tumor size when study began was 100-125 mg. On day one of the study, animals were randomly assigned to the three groups described above.

Figure 8:
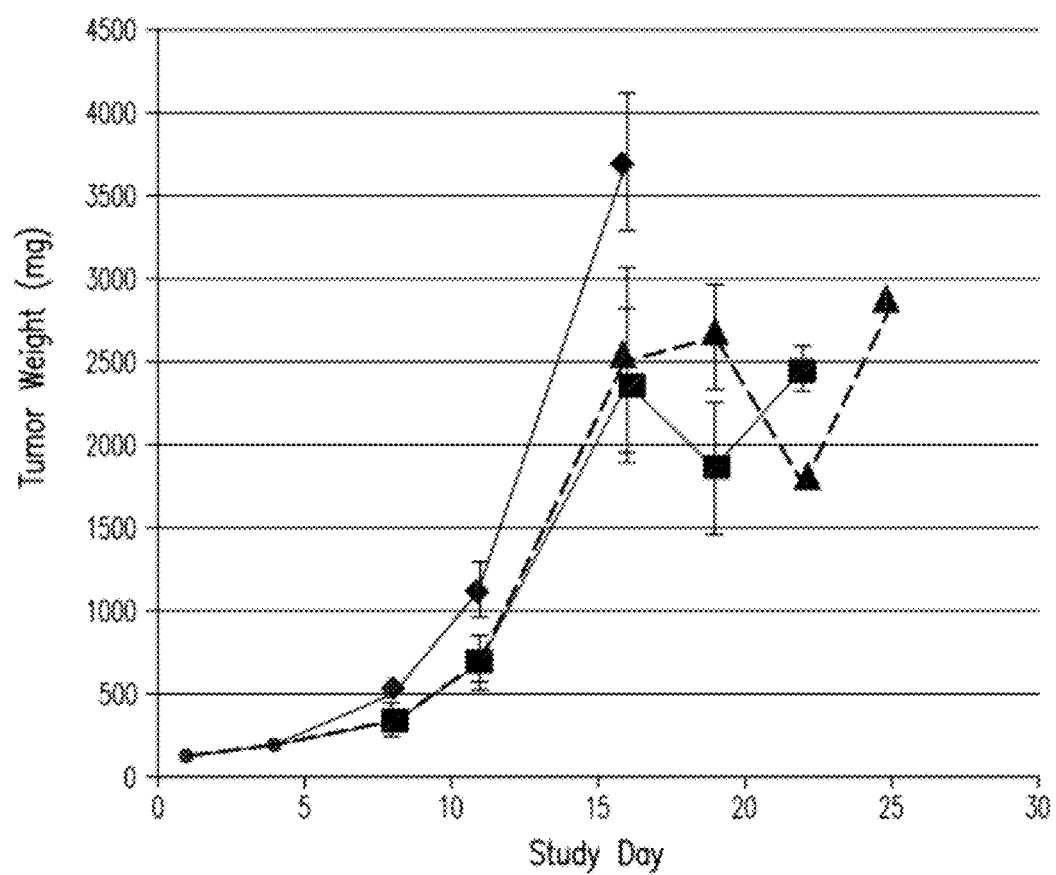
FIG. 8 depicts the change in tumor mass of A2780/CP treated mice over the course of the disclosed study. The control group is represented by (♦), the group receiving 18 mg/kg of disclosed HIF-2α stabilizer is represented by (▲) and the group receiving 36 mg/kg of disclosed HIF-2α stabilizer is represented by (■).
Figure 9:
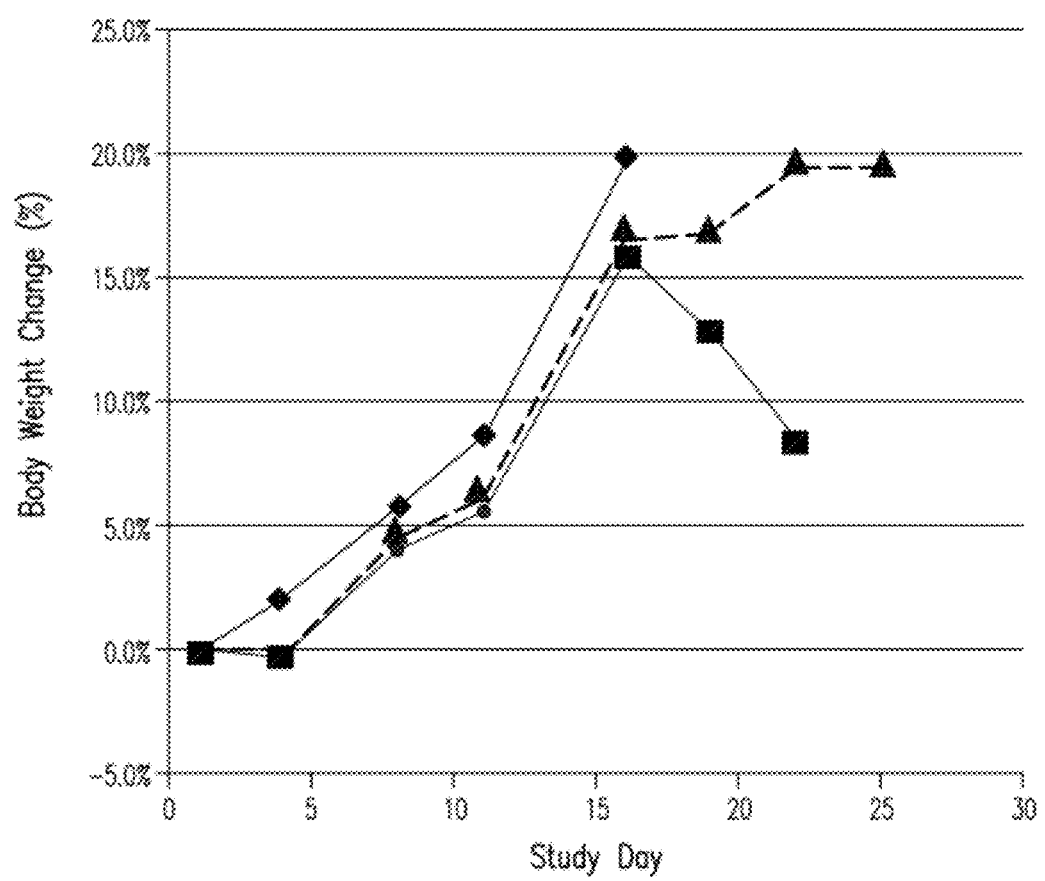
FIG. 9 depicts the change in percent body mass of A2780/CP treated mice over the course of the disclosed study. The control group is represented by (♦), the group receiving 18 mg/kg of disclosed HIF-2α stabilizer is represented by (▲) and the group receiving 36 mg/kg of disclosed HIF-2α stabilizer is represented by (■).

Tumors were collected from Groups 1-3 of the main study when individual tumors reached a tumor weight of ≥2000 mg by using the procedure above. Tumor size measurements and animal body weight were taken twice weekly. Table I below and FIGS. 7 to 9 summarize the results of this study.

TABLE I

| Study Day | Wgt % change | No. Surviving Animals | Mean Tumor Mass (mg) | Median Tumor Mass (mg) |
|---|---|---|---|---|
| CONTROL | | | | |
| 1 | — | — | 119.8 | 118.0 |
| 4 | 1.99 | 9 | 189.6 | 170.7 |
| 8 | 5.79 | 9 | 493.4 | 423.9 |
| 11 | 8.54 | 9 | 1124.5 | 962.4 |
| 16 | 19.71 | 9 | 3700.8 | 3231.1 |
| 18 mg/kg COMPOUND QD | | | | |
| 1 | — | — | 119.6 | 121.3 |
| 4 | −0.31 | 10 | 188.2 | 191.0 |
| 8 | 4.40 | 10 | 326.9 | 243.8 |
| 11 | 6.02 | 10 | 682.8 | 528.0 |
| 16 | 16.40 | 10 | 2508.0 | 1826.2 |
| 19 | 16.82 | 6 | 2647.4 | 3030.1 |
| 22 | 19.43 | 1 | 1761.6 | 1761.6 |
| 25 | 19.43 | 1 | 2838.3 | 2838.3 |
| 36 mg/kg COMPOUND QD | | | | |
| 1 | — | — | 120.3 | 123.3 |
| 4 | −0.41 | 10 | 186.4 | 182.8 |
| 8 | 4.04 | 10 | 312.8 | 323.4 |
| 11 | 5.48 | 10 | 708.1 | 830.4 |
| 16 | 15.86 | 10 | 2354.5 | 2441.8 |
| 19 | 12.79 | 4 | 1858.8 | 1568.0 |
| 22 | 8.50 | 3 | 2456.9 | 2384.6 |

Figure 7:
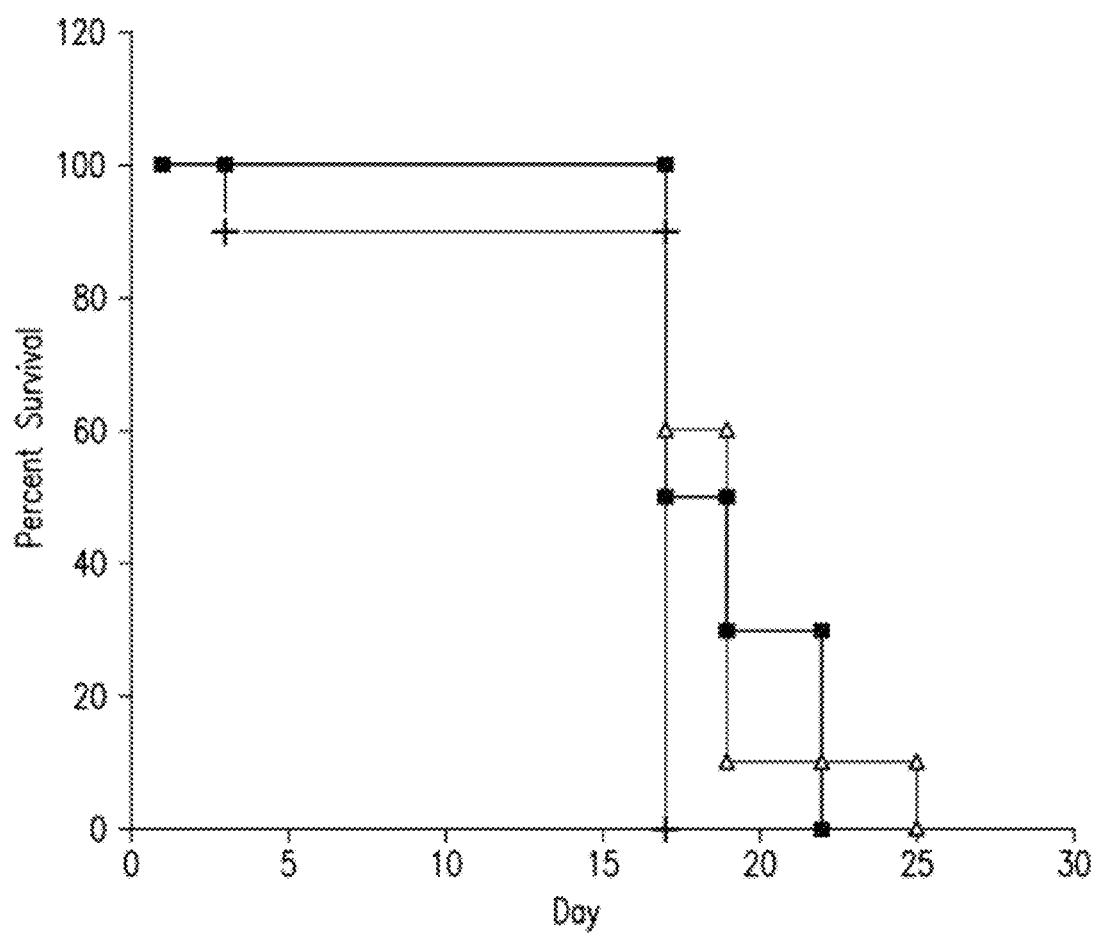
FIG. 7 depicts the number of surviving animals during the course of a study wherein mice are inoculated with approximately $10^7$ A2780/CP tumor cells as disclosed herein. The line indicated by (♦) represent the control group, the line indicated by (▲) represents the group that received 18 mg/kg of the disclosed HIF-2α stabilizer and the line indicated by (■) represents the group that received 36 mg/kg of the disclosed HIF-2α stabilizer.

FIG. 7 indicates the number of surviving animals at each evaluation point in the study. The line indicated by (♦) represent the control group, the line indicated by (▲) represents the group that received 18 mg/kg of compound and the line indicated by (●) represents the group that received 36 mg/kg of compound.

FIG. 8 depicts the change in tumor mass over the course of the study for the control group (♦), the group receiving 18 mg/kg of compound (▲) and the group receiving 36 mg/kg of compound (■).

FIG. 9 depicts the change in percent body mass for the control group (♦), the group receiving18 mg/kg of compound (▲) and the group receiving 36 mg/kg of compound (■).

As can be seen from FIGS. 7 to 9 and the above-data in Table I, the rate of tumor mass growth was significantly reduced compared to the control group, all of which had tumors masses exceeding 2,000 mg (study end point) by day 16.

Purification of Peripheral Blood Monocytes and Generation of Monocyte-Derived Macrophages.

Human peripheral blood mononuclear cells (PBMCs) were isolated from fresh peripheral blood leukocyte source packs (American Red Cross, Columbus Ohio) by density gradient centrifugation over Lymphocyte Separation Medium (Cellgro). Monocytes were purified from total PBMCs by layering over FBS. Monocytes were cultured in endotoxin-free RPMI-1640 supplemented with 1% fetal bovine serum (FBS), 0.1% human serum albumin (HSA), and 10 μg/mL of the endotoxin inhibitor polymyxin B. In some experiments, freshly isolated monocytes were differentiated into macrophages by three-day culture in media containing 10% FBS, 1% PSA (penicillin G sodium, streptomycin sulfate, and amphotericin B), and 20 ng/mL M-CSF. Macrophages were serum-starved for 2 hours prior to stimulation. Monocytes or monocyte-derived macrophages were treated for 24 hours with 10 ng/mL GM-CSF, 10 μM disclosed HIF-2α stabilizer, or an equivalent volume of the vehicle controls (PBS or DMSO, respectively). Cell-free culture supernatants were harvested and analyzed for VEGF or sVEGFR-1 by ELISA (R&D Systems).

Generation of HIF-2α$^{flox/flox}$/LysMcre Mice and Culture of Bone Marrow-Derived Macrophages.

HIF-2α$^{flox/flox}$ mice (originally developed by Dr. Celeste Simon, University of Pennsylvania) and LysMcre recombinase mice (originally developed by Irmgard Foerster, University of Duesseldorf) (both purchased from The Jackson Laboratory, Bar Harbor, Me.) were crossed to generate mice homozygous for both LysMcre and the floxed HIF-2α allele. LysMcre recombinase mice, which express no floxed alleles, were used as controls. Deletion of HIF-2α in HIF-2α$^{flox/flox}$/LysMcre macrophages, but not the LysMcre control macrophages, was confirmed at the transcript level by real-time PCR.

To generate bone marrow-derived macrophages (BDMs), femoral bone marrow was isolated and progenitor cells were plated in RPMI-1640 supplemented with 10% FBS, 1% PSA, 10 μg/mL of polymyxin B, and 20 ng/mL of recombinant murine M-CSF. Cells were cultured for 5 days with the addition of fresh M-CSF every other day. Differentiated BDM were serum-starved for 2 hours and then treated with 100 ng/mL of murine GM-CSF and/or 25 μM the disclosed HIF-2α stabilizer in RPMI-1640 containing 1% FBS and 10 μg/mL polymixin B. Culture supernatants were collected after 72 hours and assayed for VEGF and sVEGFR-1 content by ELISA (R&D Systems).

Real-Time PCR.

Human monocytes were left untreated or were stimulated with 100 ng/mL GM-CSF at normoxia or at 0.5% $O_2$. At various time-points, cells were harvested in Trizol reagent (Invitrogen) and RNA was extracted in chloroform and then purified using the RNeasy Minikit (Qiagen). In murine studies, organs harvested at the time of euthanasia were flash-frozen in liquid nitrogen, pulverized in liquid nitrogen, and then dissolved in Trizol. cDNA was generated from 1 μg of RNA using the Superscript First Strand Synthesis System (Invitrogen) and used for real-time PCR using previously described primers and SYBR Green PCR Master Mix (Applied Biosciences), according to the manufacturer's instructions. Data were analyzed according to the comparative threshold method and normalized against the β-actin internal control transcript. Results are semi-quantitative and represent the fold difference in transcript levels in a particular sample as compared with levels in untreated cells from the same donor.

Murine Melanoma Tumor Model.

6-8-week-old C57BL/6 mice were injected with 1×10$^5$ B16F10 murine melanoma cells murine subcutaneously on the left flank. Once tumors become palpable (approximately 5 days), mice were randomly allocated to receive treatment with either: 20% PEG-400 in 5% sucrose (vehicle for disclosed HIF-2α stabilizer) and PBS (vehicle for GM-CSF), 20% PEG-400 and GM-CSF (100 ng per mouse in a 50 μL volume), disclosed HIF-2α stabilizer (17.5 mg/kg mouse weight in a 100 μL volume) and PBS, or the disclosed HIF-2α stabilizer and GM-CSF (same concentrations). The disclosed HIF-2α stabilizer (or the vehicle control) was administered intraperitoneally, while GM-CSF (or the vehicle control) was administered intratumorally. Mice were treated intratumorally 3 times per week until tumors reached a size of 20 mm in any dimension (approximately 2.5 weeks), at which point mice were be euthanized, in accordance with institutional policy. Tumor diameters were measured 3 times per week with calipers, and tumor volumes will be calculated as follows: Tumor volume=0.5×[(large diameter)×(small diameter)$^2$]. For experiments analyzing the effect of neutralizing sVEGFR-1 in combination with disclosed HIF-2α stabilizer treatment, mice were treated intraperitoneally 3×/week with either disclosed HIF-2α stabilizer or vehicle control, and intratumorally with either 4 μg anti-VEGFR-1 neutralizing antibody (R&D Systems) or 4 μg polyclonal goat IgG isotype control (Santa Cruz Biotechnology) in a 50 μL volume. All protocols were approved by the Ohio State University Animal Care and Use Committee, and mice were treated in accordance with institutional guidelines for animal care.

Evaluation of Lung Metastases.

Lung metastases were evaluated by detection of mRNA for melanocyte-specific proteins within the lungs of tumor-bearing mice. B16F10 tumor-bearing mice were treated with intratumoral GM-CSF and/or the disclosed HIF-2α stabilizer, as described above. At the time of sacrifice, lungs were excised and flash-frozen in liquid nitrogen. Frozen lungs were homogenized in liquid nitrogen and the pulverized material was dissolved in Trizol reagent (Invitrogen). RNA was extracted in chloroform and purified using the RNeasy Minikit (Qiagen). cDNA was generated from 1 ng of RNA using the Superscript First Strand Synthesis System (Invitrogen) and used for real-time PCR using SYBR Green PCR MasterMix (Applied Biosciences) according to the manufacturers' instructions. The melanocyte-specific mRNAs TRP2 and Pmel17 were detected by nested PCR using a modification of the protocol described by Tsukamoto et al. For the initial reaction, 30 cycles of PCR were carried out (95° C. for 1 minute, 58° C. for 1 min, 72° C. for 1 min) in a 20 μl reaction volume containing 2 μl of cDNA. For reamplification with the nested primers, 1 μL of the first reaction product was amplified in a 20 μl reaction volume for a further 30 cycles. Data were analyzed according to the comparative threshold method and normalized against the β-actin internal control transcript. Results are semi-quantitative and represent the fold difference in transcript levels in the disclosed HIF-2α stabilizer and/or GM-CSF-treated mice as compared with levels in vehicle control mice.

Statistical Analyses.

The ANOVA test was used to compare independent measurements between multiple treatment groups. The data was log-transformed to normalize the variance across groups. P-values were adjusted using the Holm's procedure to conserve the type I error at 0.05 due to the multiple comparisons. For tumor growth data, changes in tumor volume over time were assessed via a longitudinal model. Tumor values were log-transformed, and estimated slopes (changes in tumor volume over time) were calculated with 95% confidence intervals. Estimated differences in tumor volume were calculated by a random-effects regression of the longitudinal data. For all analyses, p≤0.05 was considered statistically significant.

Inhibition of PHD3 with the Disclosed HIF-2α Stabilizer Enhances Monocyte and Macrophage Production of sVEGFR-1 but not VEGF.

Monocyte production of sVEGFR-1 in response to GM-CSF and hypoxia is dependent on HIF-2α, while HIF-1α controlled monocyte production of VEGF under the same conditions. While not wishing to be bound by theory, the inventors herein now believe that selective stabilization of HIF-2α would enhance sVEGFR-1 production from GM-CSF-stimulated monocytes, without affecting VEGF production.

Figure 11A:
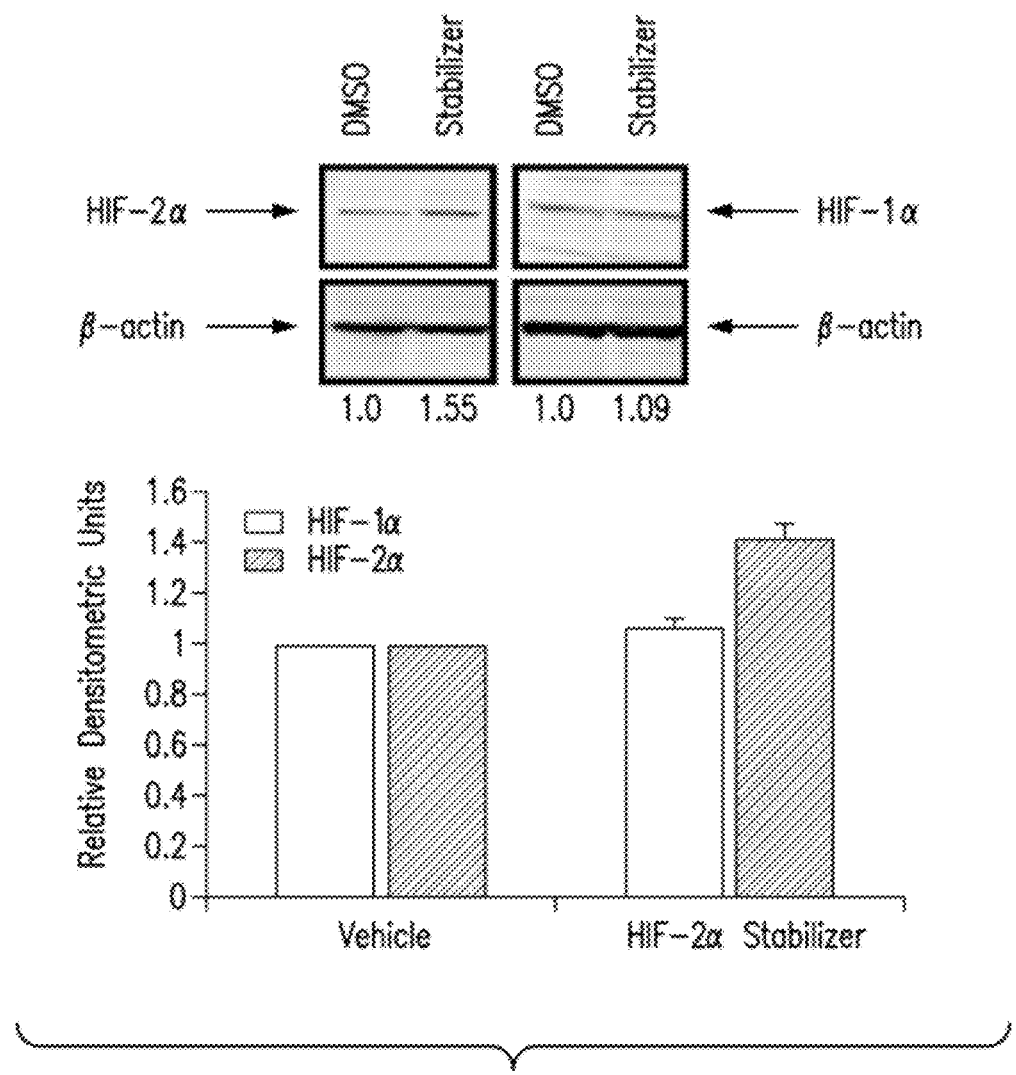
FIG. 11A—an increase in HIF-2α protein in cells treated with disclosed HIF-2α stabilizer ($p=0.001$), with no corresponding increase in HIF-1α ($p=0.105$).

In order to confirm the selective upregulation of HIF-2α by the disclosed HIF-2α stabilizer, murine bone marrow-derived macrophages were treated with the disclosed HIF-2α stabilizer for 18 hours, and cells were then lysed and immunoblotted for HIF-1α and HIF-2α. The inventors observed an increase in HIF-2α protein in cells treated with the disclosed HIF-2α stabilizer, with no corresponding increase in HIF-1α (FIG. 11A).

Figure 11B:
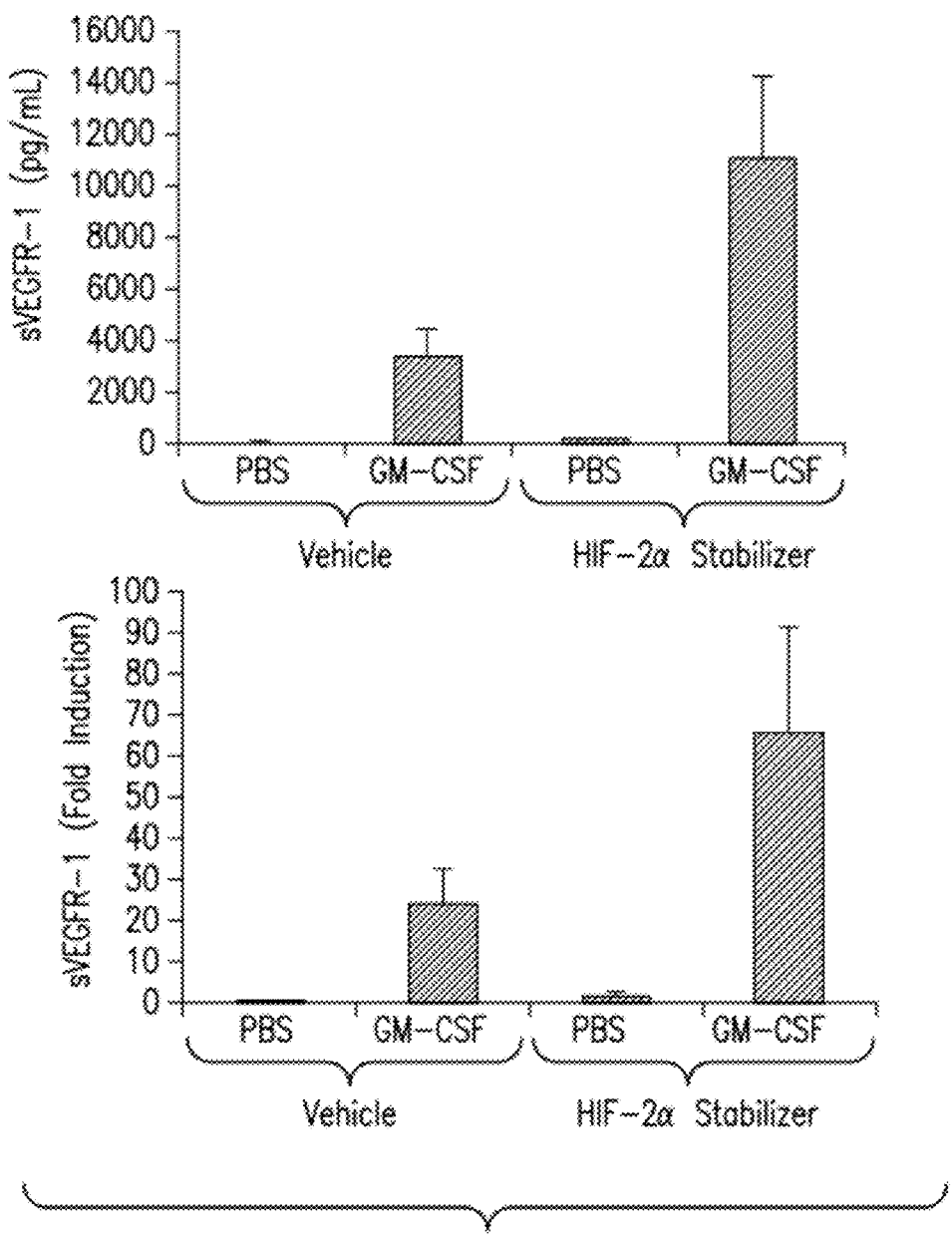
FIG. 11B—sVEGFR-1 production by GM-CSF-treated monocytes increased significantly when monocytes were also treated with disclosed HIF-2α stabilizer, at both the protein and the transcript level ($p=0.007$ and $p=0.033$, respectively).

In order to determine whether stabilization of HIF-2α increased sVEGFR-1 production, human peripheral blood monocytes were stimulated with 100 ng/mL GM-CSF in the presence or absence of 10 μM the disclosed HIF-2α stabilizer. sVEGFR-1 production by GM-CSF-treated monocytes increased significantly when monocytes were also treated with the disclosed HIF-2α stabilizer, at both the protein and the transcript level (p=0.007 and p=0.033, respectively) (FIG. 11B).

VEGF levels in the same supernatants were measured using an ELISA that detects free (bioavailable) VEGF, but does not detect VEGF bound to sVEGFR-1. Treatment of cells with the disclosed HIF-2α stabilizer did not significantly increase production of VEGF (p=0.133). VEGF protein was undetectable in the supernatants of GM-CSF-stimulated monocytes, due to neutralization of VEGF by sVEGFR-1 (FIG. 11C).

Figure 11C:
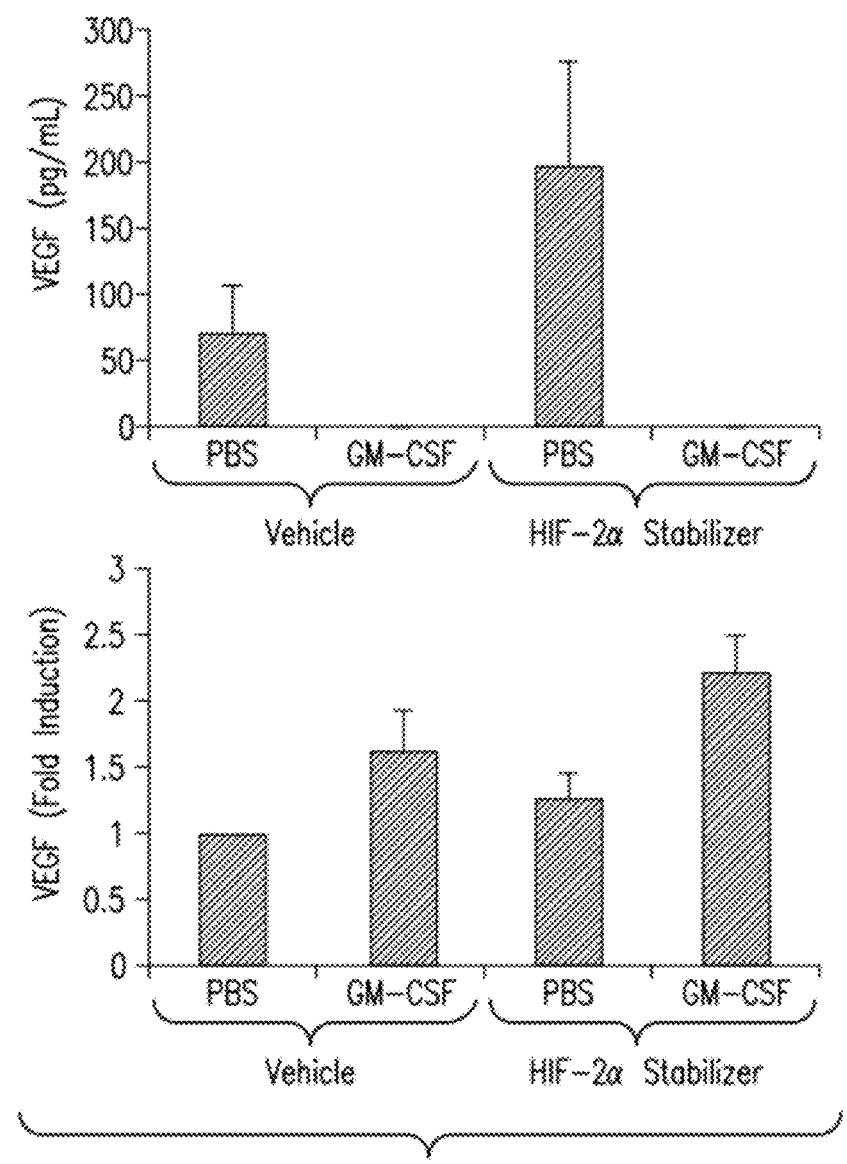
FIG. 11C—evaluation of VEGF transcript levels by real-time PCR revealed that while GM-CSF increased VEGF production, there was no difference in VEGF production between monocytes stimulated with GM-CSF alone or with GM-CSF and disclosed HIF-2α stabilizer, at either the protein or the transcript level ($p=0.133$ and $0.556$, respectively).

Evaluation of VEGF transcript levels by real-time PCR revealed that while GM-CSF increased VEGF production, there was no difference in VEGF production between monocytes stimulated with GM-CSF alone or with GM-CSF and the disclosed HIF-2α stabilizer (p=0.556) (FIG. 11C).

These results demonstrate that selective stabilization of HIF-2α enhances monocyte production of sVEGFR-1 but not VEGF.

Since monocyte production of VEGF was dependent on HIF-1α, the inventors herein determined whether selective stabilization of HIF-1α via inhibition of PHD2 would increase monocyte production of VEGF but not sVEGFR-1. In order to make such determination, human peripheral blood monocytes were stimulated with GM-CSF in the presence of a selective inhibitor of PHD2 which results in the stabilization of HIF-1α.

Figure 11D:
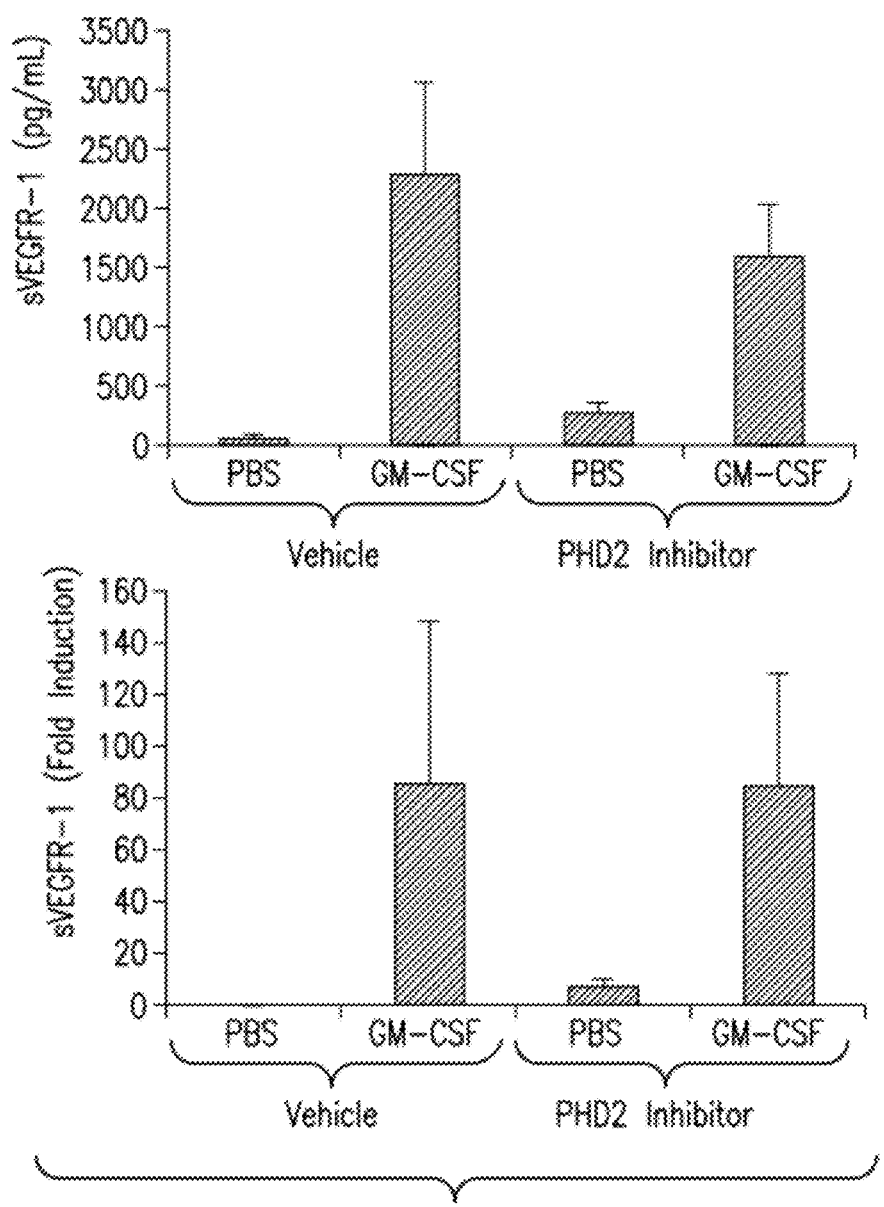
FIG. 11D—there was no difference in sVEGFR-1 production from monocytes stimulated with GM-CSF alone or monocytes co-stimulated with disclosed HIF-2α stabilizer, at either the protein or transcript level ($p=0.306$ and $p=0.566$, respectively).

GM-CSF induced monocyte production of sVEGFR-1. However, there was no difference in sVEGFR-1 production from monocytes stimulated with GM-CSF alone or monocytes co-stimulated with the selective inhibitor of PHD2, at either the protein or transcript level (p=0.306 and p=0.566, respectively) (FIG. 11D).

Figure 11E:
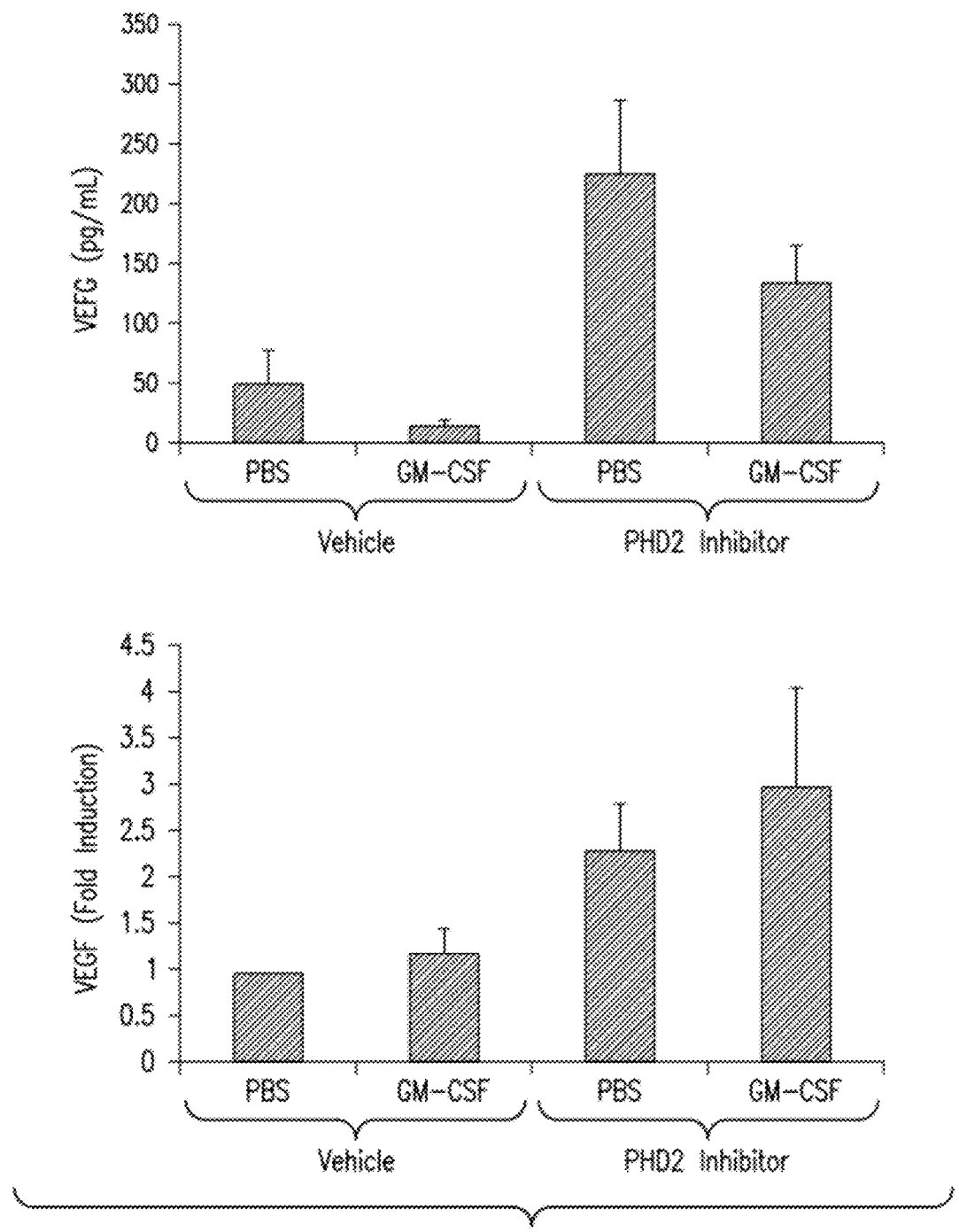
FIG. 11E—disclosed HIF-2α stabilizer increased monocyte production of VEGF protein and mRNA ($p=0.011$ and $p=0.007$, respectively).

However, the selective inhibitor of PHD3 increased monocyte production of VEGF protein and mRNA (p=0.011 and p=0.007, respectively) (FIG. 11E).

In order to confirm that sVEGFR-1 production was induced by stabilization of HIF-2α, bone marrow-derived macrophages from mice were utilized with a myeloid-specific deletion of HIF-2α (HIF-2α$^{flox/flox}$/LysMcre).

Figure 11F:
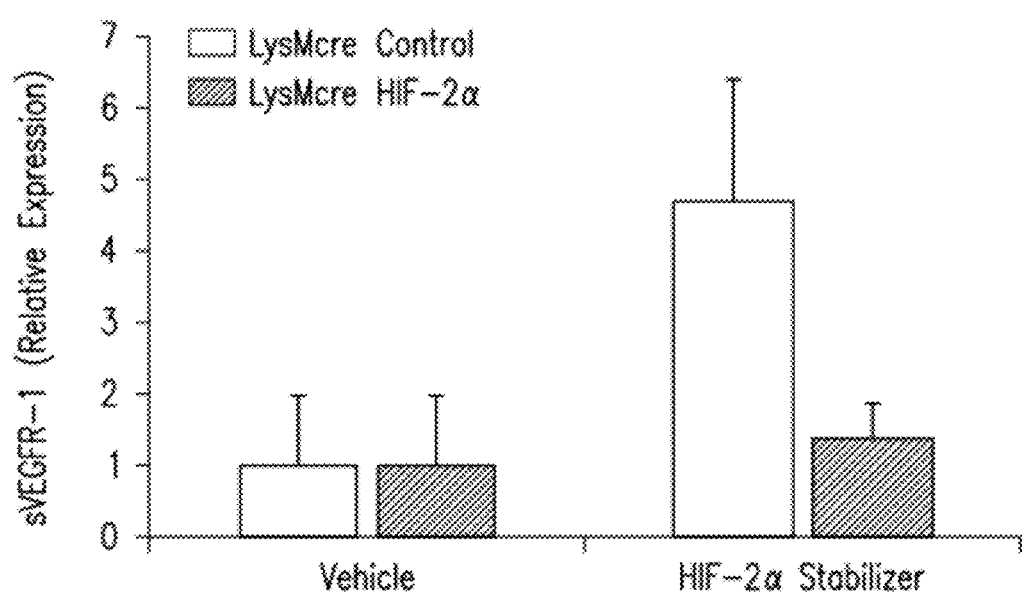
FIG. 11F—disclosed HIF-2α stabilizer induced sVEGFR-1 transcription from control macrophages ($p=0.036$), but not from HIF-2α-deficient macrophages ($p=0.881$).

The disclosed HIF-2α stabilizer induced sVEGFR-1 transcription from control macrophages (p=0.036), but not from HIF-2α-deficient macrophages (p=0.881) (FIG. 11F).

These results show that sVEGFR-1 production is a HIF-2α-dependent effect. Furthermore, these results demonstrate that inhibition of PHD3 with the disclosed HIF-2α stabilizer stabilizes HIF-2α and selectively induces sVEGFR-1, but not VEGF, from GM-CSF-stimulated monocytes.

Stabilization of HIF-2α Increases the Anti-Tumor Effects of GM-CSF and Enhances Survival in a Murine Melanoma Model.

The anti-tumor effects of GM-CSF are dependent on HIF-2α-mediated sVEGFR-1 production from tumor-associated macrophages in a murine melanoma model (Roda et al., *J. Immunol*, "Hypoxia-Inducible Factor-2α Regulates GM-CSF-Derived Soluble Vascular Endothelial Growth Factor Receptor 1 Production from Macrophages and Inhibits Tumor Growth and Angiogenesis", published on line before print Jul. 15, 2011, doi: 10.4049/jimmunol.1100841).

It was then determined whether the chemical stabilization of HIF-2α might increase sVEGFR-1 production from tumor-associated macrophages and therefore enhance the anti-tumor effects of GM-CSF.

Figure 12A:
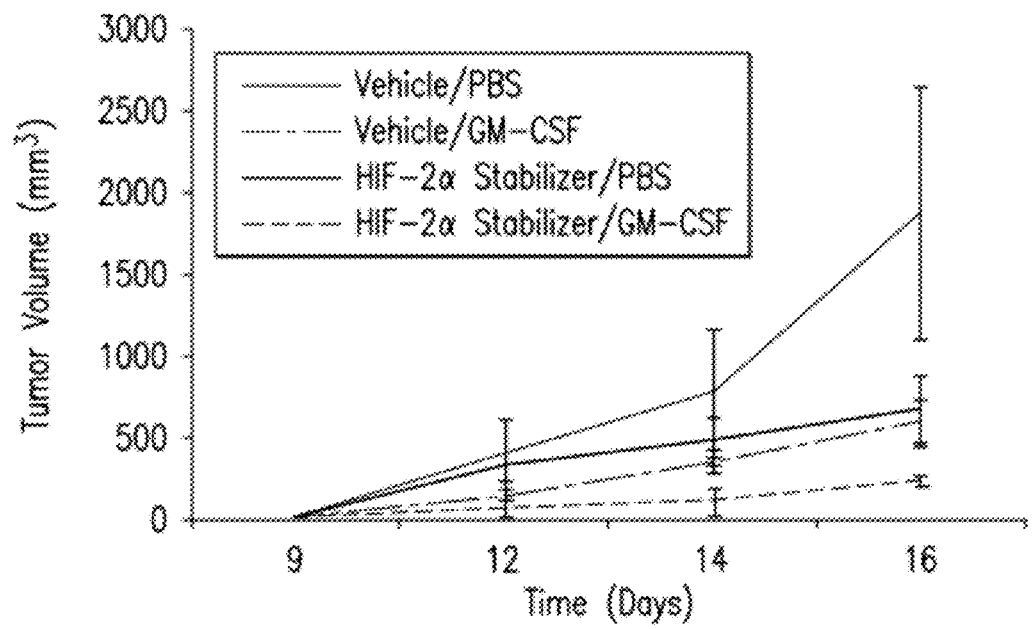
FIG. 12A—combined treatment with GM-CSF and disclosed HIF-2α stabilizer disclosed HIF-2α stabilizer further decreased tumor growth compared to either treatment alone ($p<0.001$).
Figure 12B:
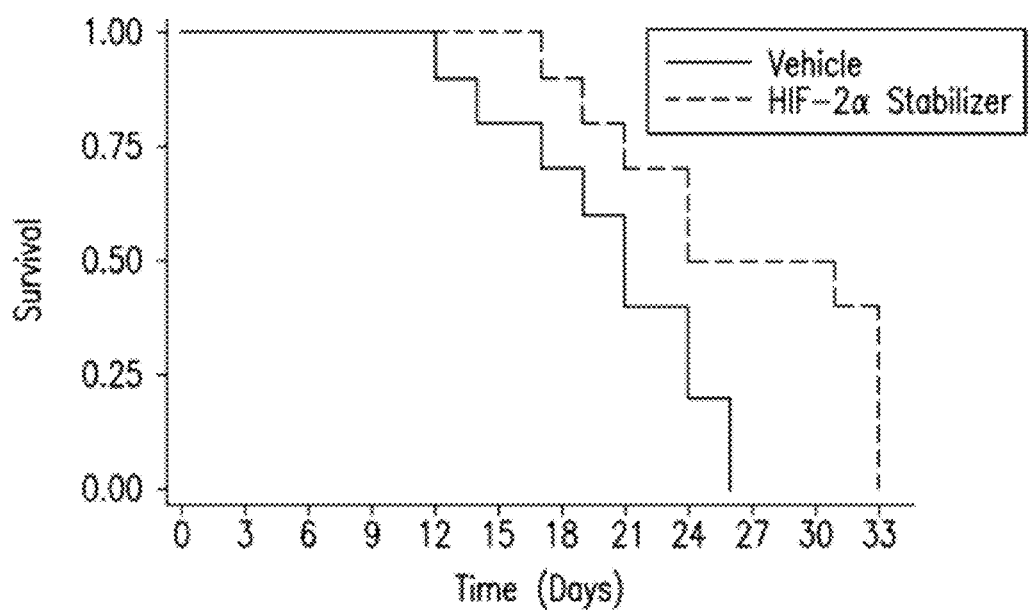

Mice bearing subcutaneous B16F10 melanomas were treated 3×/week with GM-CSF (100 ng/mouse, intratumoral), the disclosed HIF-2α stabilizer (17.5 mg/kg, intraperitoneal), or the combination (or the appropriate vehicle controls). Based on a longitudinal model using log-transformed values, no significant differences in tumor volume were found between the four groups at baseline. However, at day 16 of treatment, the average tumor volumes for mice receiving either GM-CSF or the disclosed HIF-2α stabilizer were significantly smaller than for mice treated with the vehicle controls (each p<0.001). Furthermore, combined treatment with GM-CSF and the disclosed HIF-2α stabilizer further decreased tumor growth compared to either treatment alone (FIG. 12A) (p<0.001). These data demonstrate that the disclosed HIF-2α stabilizer can enhance the anti-tumor effects of GM-CSF in a melanoma model. The disclosed HIF-2α stabilizer alone also enhanced the survival of B16F10 melanoma-bearing mice. FIG. 12B shows a 3-day increase in median survival (which was defined as the time to a tumor diameter of 20 mm$^3$) in mice treated with the disclosed HIF-2α stabilizer (p=0.023).

The Disclosed HIF-2α Stabilizer Enhances sVEGFR-1 Production and Decreases Tumor Angiogenesis in Response to GM-CSF.

Again, while not wishing to be bound by theory, the inventors herein now believe that chemical stabilization of HIF-2α with the disclosed HIF-2α stabilizer would increase sVEGFR-1 production in response to GM-CSF, thereby reducing tumor growth and angiogenesis. Real-time PCR was used to evaluate the levels of sVEGFR-1 and VEGF mRNA within tumors from mice treated with GM-CSF, the disclosed HIF-2α stabilizer, or the combination.

Figure 13A:
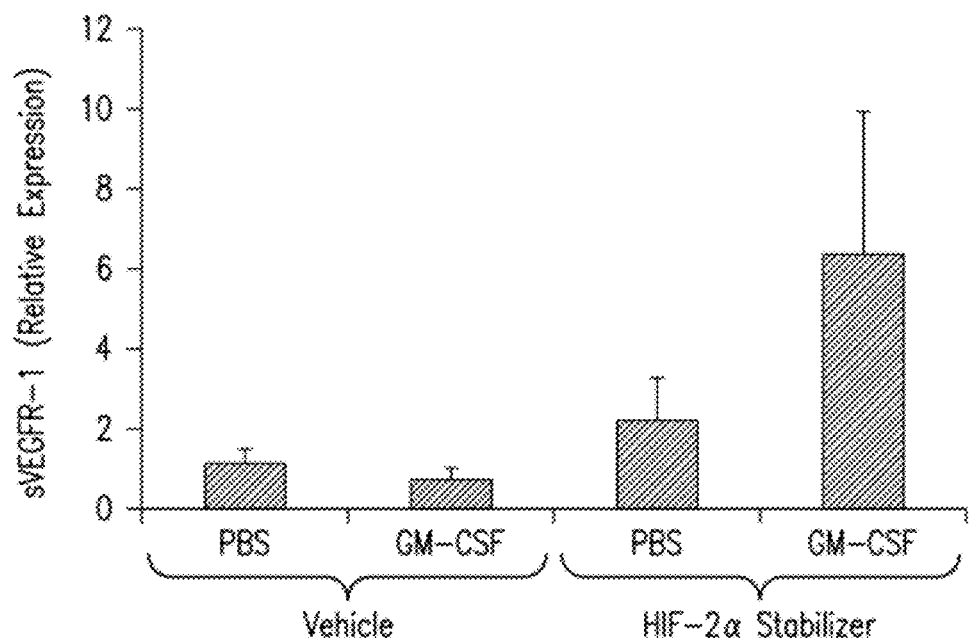
FIG. 13A—Increased levels of sVEGFR-1 were detected within the tumors of mice treated with both GM-CSF and disclosed HIF-2α stabilizer ($p=0.031$).
Figure 13B:
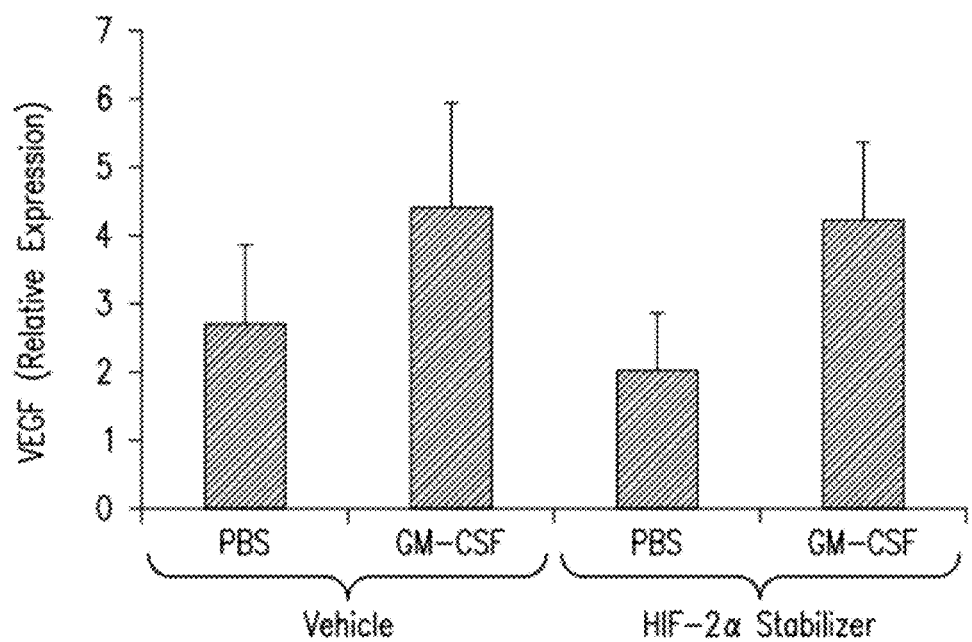
FIG. 13B—GM-CSF (alone or in combination with disclosed HIF-2α stabilizer failed to increase levels of intratumoral VEGF over the levels observed in vehicle control-treated mice ($p=0.490$).
Figure 13C:
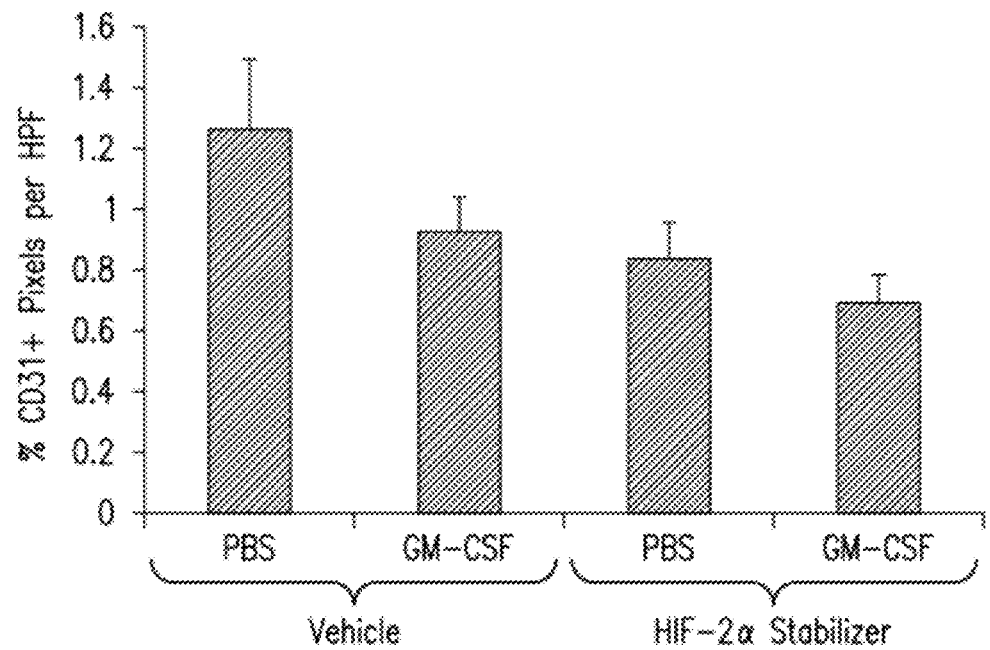
FIG. 13C—combination treatment with GM-CSF and disclosed HIF-2α stabilizer significantly reduced tumor vascularity in melanoma-bearing mice, possibly through the induction of sVEGFR-1 ($p<0.001$).

Increased levels of sVEGFR-1 were detected within the tumors of mice treated with both GM-CSF and the disclosed HIF-2α stabilizer (FIG. 13A) (p=0.031). Conversely, GM-CSF (alone or in combination with the disclosed HIF-2α stabilizer) failed to increase levels of intratumoral VEGF over the levels observed in vehicle control-treated mice (FIG. 13B) (p=0.490). To confirm that the increased sVEGFR-1 production resulted in decreased tumor angiogenesis, tumors from each of the mice were stained by immunohistochemistry for the endothelial cell marker CD31. As shown in FIG. 13C, combination treatment with GM-CSF and the disclosed HIF-2α stabilizer significantly reduced tumor vascularity in melanoma-bearing mice, possibly through the induction of sVEGFR-1 (p<0.001).

Figure 13D:
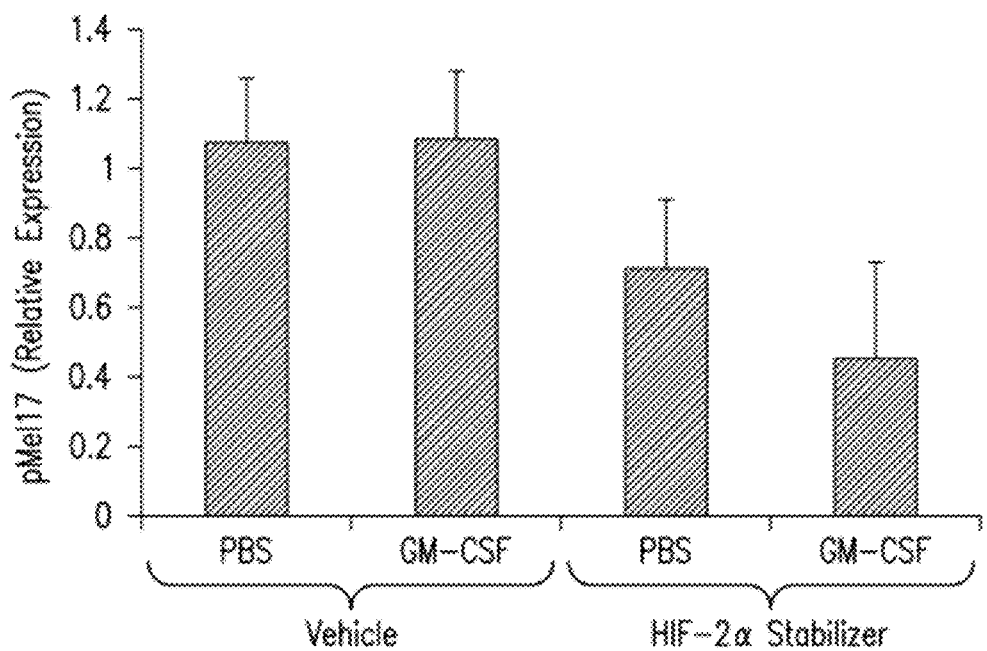
FIG. 13D—significantly reduced levels of the melanoma-specific gene Pmel17 were detected within the lungs of mice treated with GM-CSF and the disclosed HIF-2α stabilizer, as compared to vehicle control-treated mice.

Because increased angiogenesis is associated with an increased risk of metastasis, the inventors herein evaluated lung metastasis in mice treated with GM-CSF, the disclosed HIF-2α stabilizer, or the combination. Significantly reduced levels of the melanoma-specific gene Pmel17 were detected within the lungs of mice treated with GM-CSF and the disclosed HIF-2α stabilizer, as compared to vehicle control-treated mice (FIG. 13D).

These results demonstrate that the disclosed HIF-2α stabilizer enhances the anti-angiogenic effects of GM-CSF, by increasing sVEGFR-1 production from tumor-associated macrophages.

The Anti-Tumor Effects of the Disclosed HIF-2α Stabilizer are Dependent on sVEGFR-1 Production.

Increased sVEGFR-1 levels in the tumors of mice treated with GM-CSF and the disclosed HIF-2α stabilizer, correlating with decreased tumor growth and angiogenesis. To confirm that the modulation of tumor growth and angiogenesis was due to sVEGFR-1 production in response to the disclosed HIF-2α stabilizer, mice were treated with the disclosed HIF-2α stabilizer in the presence or absence of an sVEGFR-1 neutralizing Ab.

Figure 14A:
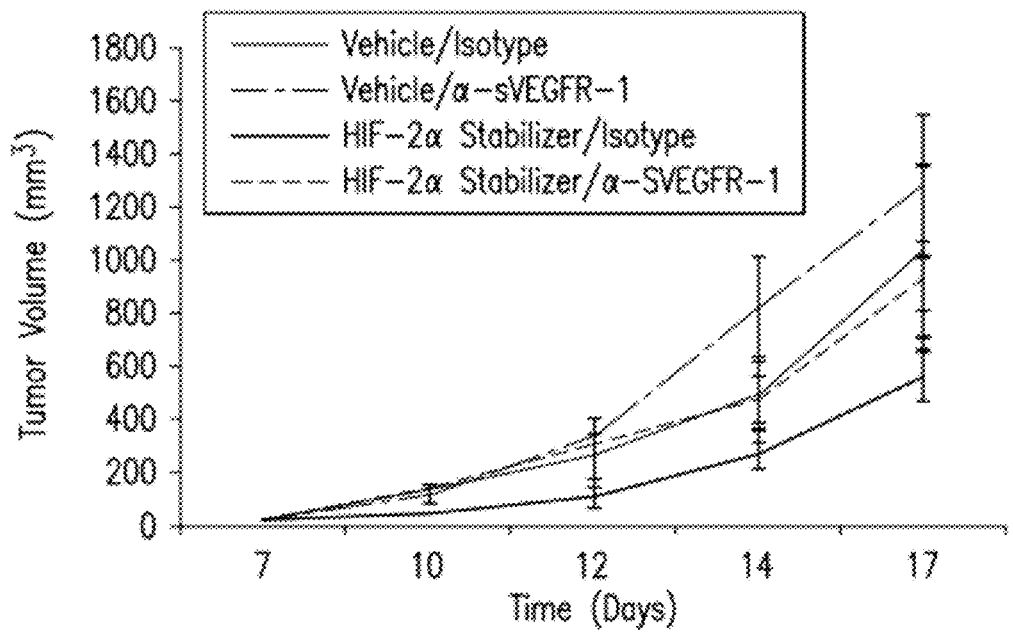
FIG. 14A—disclosed HIF-2α stabilizer decreased tumor growth in mice treated with an isotype control antibody ($p<0.001$), but had no effect on tumor growth in mice also treated with the anti-sVEGFR-1 neutralizing antibody ($p=0.245$).

The disclosed HIF-2α stabilizer decreased tumor growth in mice treated with an isotype control antibody (p<0.001), but had no effect on tumor growth in mice also treated with the anti-sVEGFR-1 neutralizing antibody (p=0.245) (FIG. 14A).

Figure 14B:
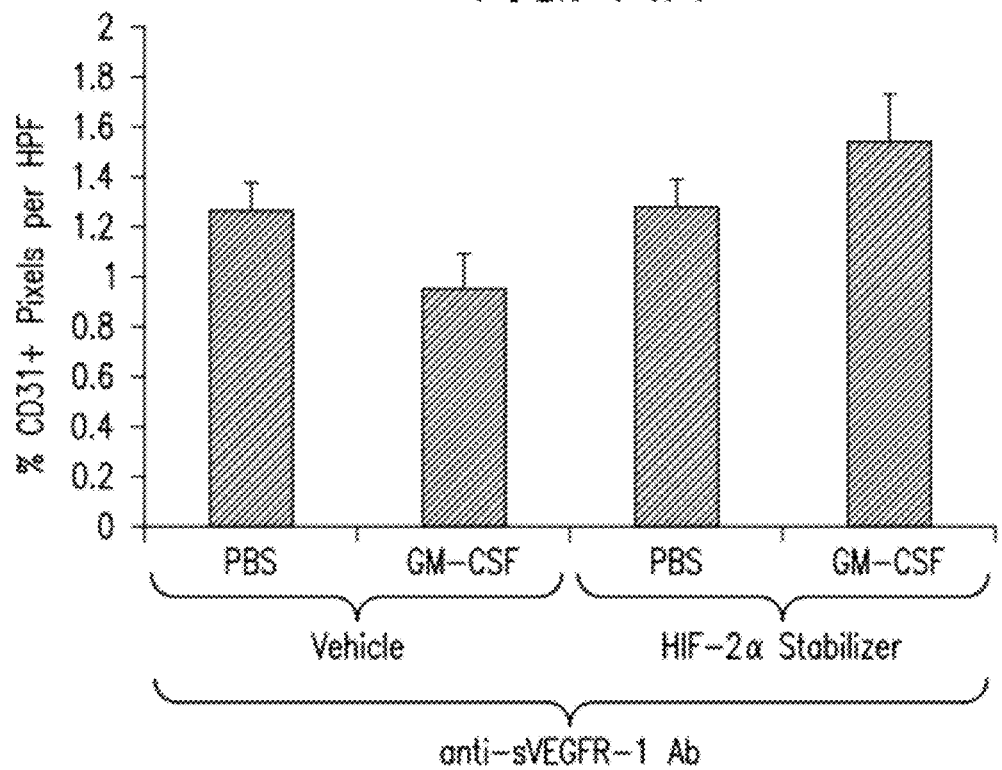
FIG. 14B—disclosed HIF-2α stabilizer decreased tumor vascularity in the mice treated with the control antibody ($p=0.022$) but not in the mice treated with the sVEGFR-1 neutralizing Ab.

To confirm the role of sVEGFR-1 production in tumor angiogenesis, the inventors herein immunostained the tumors for the endothelial cell marker CD31. As shown in FIG. 14B, the disclosed HIF-2α stabilizer decreased tumor vascularity in the mice treated with the control antibody (p=0.022) but not in the mice treated with the sVEGFR-1 neutralizing Ab.

These results demonstrate that the disclosed HIF-2α stabilizer decreases tumor angiogenesis by inducing sVEGFR-1.
sVEGFR-1 Production in Response to the Disclosed HIF-2α Stabilizer is Dependent on Macrophage Production of HIF-2α.

The disclosed HIF-2α stabilizer is not targeted specifically to macrophages, and will stabilize HIF-2α in all tissues, not only the tumor-associated macrophages. In order to determine the role of macrophages in the anti-tumor response to the disclosed HIF-2α stabilizer, mice with a myeloid-specific deletion of HIF-2α (HIF-2α$^{flox/flox}$/LysMcre mice) were utilized.

Figure 15:
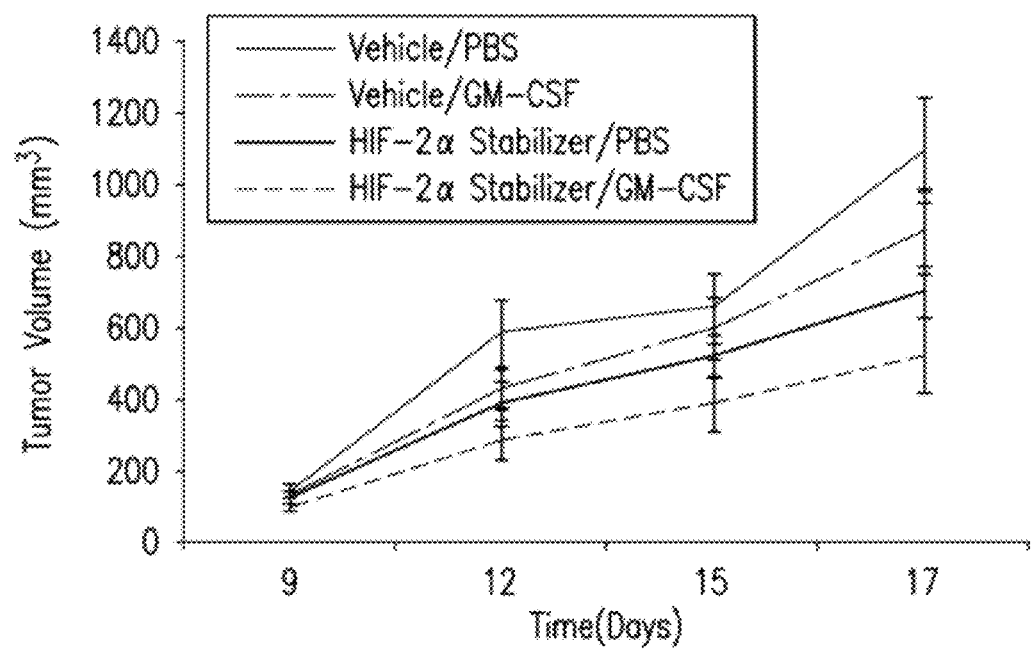
FIG. 15—disclosed HIF-2α stabilizer inhibited tumor growth in LysMcre control mice (which contain LysM-driven cre recombinase but no floxed alleles).

The disclosed HIF-2α stabilizer inhibited tumor growth in LysMcre control mice (which contain LysM-driven cre recombinase but no floxed alleles). Although the disclosed HIF-2α stabilizer reduced tumor growth in mice with HIF-2α-deficient macrophages, the magnitude of the anti-tumor response was much less than in control mice (FIG. 15).

These results demonstrate that the disclosed HIF-2α stabilizer inhibits tumor growth and angiogenesis, at least in part, by stabilizing HIF-2α in tumor-associated macrophages and inducing sVEGFR-1 production.

Human Melanoma Cell Line (A375)

Immunodeficient mice with a human melanoma cell line (A375) and treated with GM-CSF, the disclosed HIF-2α stabilizer, or the combination, as the inventor did for the B16F10 murine melanoma model. The combination of GM-CSF and the disclosed HIF-2α stabilizer significantly reduced tumor growth in this model (p=0.05). This data confirms the inventors' finding of the efficacy of GM and the disclosed HIF-2α stabilizer in an additional murine model, and is also highly biologically relevant to human cancer, at least in part because a human cancer cell line grown in mice is tested. See FIG. 15.

Murine Melanoma Tumor Models.

6-8-week-old C57BL/6 mice or SCID mice were injected with 1×10$^5$ B16F10 murine melanoma cells or 1×10$^6$ A375 human melanoma cells, respectively, subcutaneously on the left flank. Once tumors become palpable (approximately 5 days), mice were randomly allocated to receive treatment with either: 20% PEG-400 in 5% sucrose (vehicle for the disclosed HIF-2α stabilizer) and PBS (vehicle for GM-CSF), 20% PEG-400 and GM-CSF (100 ng per mouse in a 50 µL volume), the disclosed HIF-2α stabilizer (17.5 mg/kg mouse weight in a 100 µL volume) and PBS, or the disclosed HIF-2α stabilizer and GM-CSF (same concentrations). The disclosed HIF-2α stabilizer (or the vehicle control) was administered intraperitoneally, while GM-CSF (or the vehicle control) was administered intratumorally. Mice were treated intratumorally 3 times per week until tumors reached a size of 20 mm in any dimension (approximately 2.5 weeks), at which point mice were be euthanized, in accordance with institutional policy. Tumor diameters were measured 3 times per week with calipers, and tumor volumes will be calculated as follows: Tumor volume=0.5×[(large diameter)×(small diameter)$^2$].

In the study, immunocompromised SCID mice were inoculated with A375 human melanoma tumors subcutaneously. Starting when the tumors became palpable (7 days after injection), mice were treated with either the cytotoxic chemotherapy docetaxel or with the disclosed HIF-2α stabilizer. The disclosed HIF-2α stabilizer was given at a dose of 17 mg/kg, and the docetaxel was given at 1 mg/kg. Both drugs were given IP 3 times per week. The combination of docetaxel and the disclosed HIF-2α stabilizer significantly inhibited tumor growth compared to either drug alone. At the time of sacrifice, the tumors in the mice that received only the disclosed HIF-2α stabilizer were approximately 78% of the size of the control tumors, the tumors of the mice that received only chemotherapy were approximately 50% of the size of the control tumors, and the tumors of the mice that received both drugs were approximately 16% of the size of the control tumors.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A composition for stabilizing hypoxia inducible factor-2 alpha (HIF-2α) comprising:

A) an effective amount of a compound having the formula:

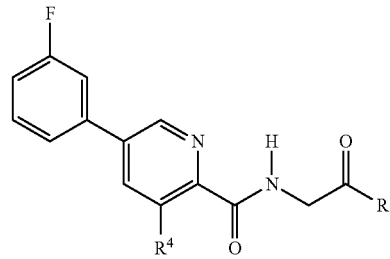

wherein R is chosen from:
i) —OR$^1$;
ii) —NR$^2$R$^3$; or
iii) —OM$^1$;
R$^1$ is:
i) hydrogen; or
ii) C$_1$-C$_6$ linear, C$_3$-C$_6$ branched or C$_3$-C$_6$ cyclic alkyl;
R$^2$ and R$^3$ are independently:
i) hydrogen;
ii) C$_1$-C$_6$ linear, C$_3$-C$_6$ branched or C$_3$-C$_6$ cyclic alkyl; or
iii) R$^2$ and R$^3$ can be taken together to form a ring having from 2 to 7 carbon atoms and from 1 to 3 heteroatoms chosen from nitrogen, oxygen and sulfur including the nitrogen atom to which R$^2$ and R$^3$ are bonded; and
M$^1$ is a cation; and
R$^4$ is:
i) —OH; or
ii) —OM$^2$; and
M$^2$ is a cation; and B) one or more pharmaceutically acceptable ingredients; and C) Granulocyte-Macrophage Colony-Stimulating Factor (GM-CSF).

2. The composition according to claim 1, wherein R is —OR¹.

3. The composition according to claim 1, wherein R¹ is hydrogen.

4. The composition according to claim 1, wherein R¹ is methyl.

5. The composition according to claim 1, wherein R⁴ is —OH.

6. The composition according to claim 1, wherein R is M¹.

7. The composition according to claim 1, having the formula:

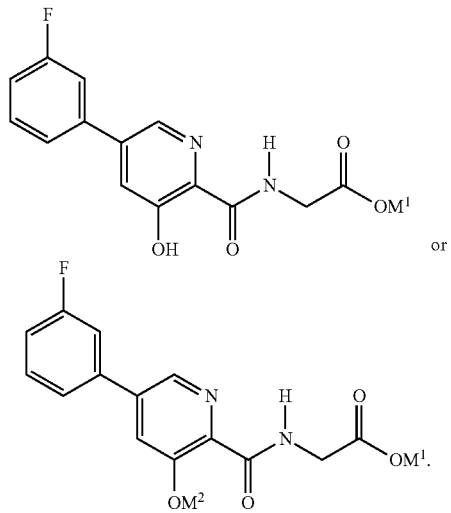

or

8. The composition according to claim 7, wherein M¹ is chosen from sodium, lithium, potassium, ammonium, and silver and M² is hydrogen or a cation chosen from sodium, lithium, potassium, ammonium, and silver.

9. The composition according to claim 7, having the formula:

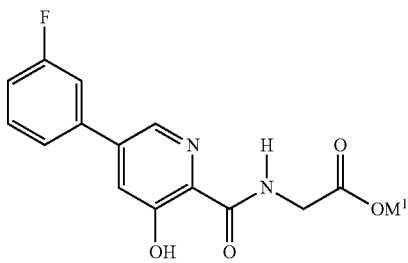

wherein M¹ is sodium or ammonium.

10. The composition according to claim 1, wherein M¹ is a cation having the formula:

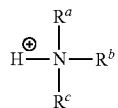

wherein $R^a$, $R^b$ and $R^c$ are each independently:
i) hydrogen;
ii) substituted or unsubstituted $C_1$-$C_{12}$ linear, $C_3$-$C_{12}$ branched, or $C_3$-$C_{12}$ cyclic alkyl;
iii) substituted or unsubstituted benzyl;
wherein one or more of $R^a$, $R^b$ and $R^c$ can be independently substituted by one or more units chosen from:
i) $C_1$-$C_{12}$ linear, $C_3$-$C_{12}$ branched, or $C_3$-$C_{12}$ alkoxy;
ii) $C_1$-$C_{12}$ linear, $C_3$-$C_{12}$ branched, or $C_3$-$C_{12}$ haloalkoxy;
iii) halogen;
iv) hydroxyl;
v) thio; or
vi) one or more of $R^a$, $R^b$ and $R^c$ can contain one or more units capable of forming a cation, anion, or zwitterions.

11. The composition according to claim 10, wherein the cation M¹ is chosen from:
i) 2-hydroxyethyl ammonium [HN⁺H₂(CH₂CH₂OH)];
ii) methyl-2-hydroxyethyl ammonium [H₂N⁺(CH₃)(CH₂CH₂OH)];
iii) di-(2-hydroxyethyl) ammonium [H₂N⁺(CH₂CH₂OH)₂];
iv) tri-(2-hydroxyethyl) ammonium [HN⁺(CH₂CH₂OH)₃]; and
v) tris-(hydroxymethyl)methyl ammonium [H₃N⁺C[(CH₂OH)]₃].

12. The composition according to claim 1, wherein the composition is a salt of an amino acid chosen from lysine, ornithine, arginine, and glutamine.

13. The composition according to claim 1, having the formula:

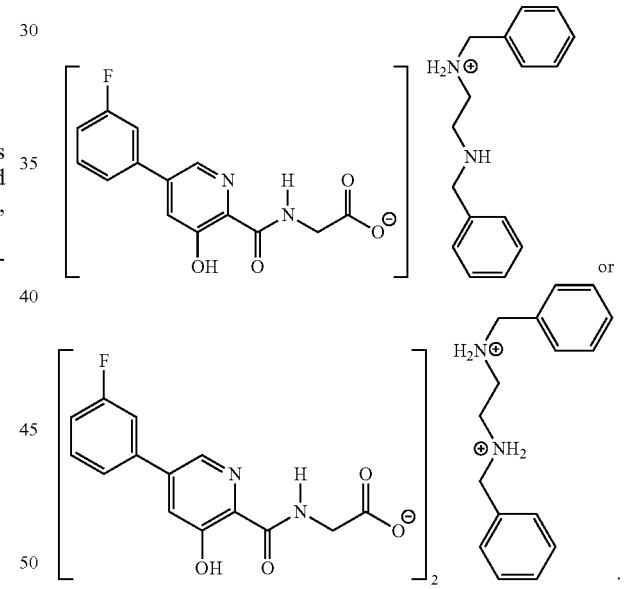

14. The composition according to claim 1, wherein the compound is chosen from:
sodium {[5-(3-fluorophenyl)-3-hydroxypyridine-2-carbonyl]-amino}acetate; disodium {[5-(3-fluorophenyl)-3-oxidopyridine-2-carbonyl]-amino}acetate; potassium {[5-(3-fluorophenyl)-3-hydroxypyridine-2-carbonyl]-amino}acetate; dipotassium {[5-(3-fluorophenyl)-3-oxidopyridine-2-carbonyl]-amino}acetate; ammonium {[5-(3-fluorophenyl)-3-hydroxypyridine-2-carbonyl]-amino}acetate; diammonium {[5-(3-fluorophenyl)-3-oxidopyridine-2-carbonyl]-amino}acetate; sodium potassium {[5-(3-fluorophenyl)-3-oxidopyridine-2-carbonyl]-amino}acetate; sodium ammonium {[5-(3-fluorophenyl)-3-oxidopyridine-2-carbonyl]-amino}acetate; potassium ammonium {[5-(3-fluorophenyl)-3-oxidopyridine-2-carbonyl]-amino}acetate; calcium bis{[5-(3-fluorophenyl)-3-hydroxypyridine-2-carbonyl]-amino}acetate; magnesium bis{[5-(3-fluorophenyl)-3-hydroxypyridine-2-carbonyl]-amino}acetate; barium bis{[5-(3-fluorophenyl)-3-hydroxypyridine-2-carbonyl]-amino}acetate; methyl ammonium {[5-(3-fluorophenyl)-3-hydroxypyridine-2-carbonyl]-amino}acetate; calcium {[5-(3-fluorophenyl)-3-oxidopyridine-2-carbonyl]-amino}acetate; magnesium {[5-(3-fluorophenyl)-3-oxidopyridine-2-carbonyl]-amino}acetate; barium {[5-(3-fluorophenyl)-3-oxidopyridine-2-carbonyl]-amino}acetate; dimethyl ammonium {[5-(3-fluorophenyl)-3-hydroxypyridine-2-carbonyl]-amino}acetate; diethyl ammonium {[5-(3-fluorophenyl)-3-hydroxypyridine-2-carbonyl]-amino}acetate; triethyl ammonium {[5-(3-fluorophenyl)-3-hydroxypyridine-2-carbonyl]-amino}acetate; dimethylethyl ammonium {[5-(3-fluorophenyl)-3-hydroxypyridine-2-carbonyl]-amino}acetate; methyldiethyl ammonium {[5-(3-fluorophenyl)-3-hydroxypyridine-2-carbonyl]-amino}acetate; 2-hydroxyethyl ammonium {[5-(3-fluorophenyl)-3-hydroxypyridine-2-carbonyl]-amino}acetate; methyl-2-hydroxyethyl ammonium {[5-(3-fluorophenyl)-3-hydroxypyridine-2-carbonyl]-amino}acetate; di(2-hydroxyethyl) ammonium {[5-(3-fluorophenyl)-3-hydroxypyridine-2-carbonyl]-amino}acetate; tri(2-hydroxyethyl) ammonium {[5-(3-fluorophenyl)-3-hydroxypyridine-2-carbonyl]-amino}acetate; tris(hydroxymethyl)methyl ammonium {[5-(3-fluorophenyl)-3-hydroxypyridine-2-carbonyl]-amino}acetate; and N-benzyl-2-(benzylamino)ethanaminium {[5-(3-fluorophenyl)-3-hydroxypyridine-2-carbonyl]-amino}acetate.

15. The composition according to claim 1, wherein R is —NR$^2$R$^3$.

16. The composition according to claim 1, wherein R$^2$ and R$^3$ are each independently hydrogen or methyl.

17. The composition according to claim 1, wherein R is —NH$_2$.

18. The composition according to claim 1, comprising a compound chosen from:

- {[5-(3-fluorophenyl)-3-hydroxypyridine-2-carbonyl]amino}acetic acid;
- methyl {[5-(3-fluorophenyl)-3-hydroxypyridine-2-carbonyl]amino}acetate;
- ethyl {[5-(3-fluorophenyl)-3-hydroxypyridine-2-carbonyl]amino}acetate;
- 5-(3-fluorophenyl)-N-(2-amino-2-oxoethyl)-3-hydroxypyridin-2-yl amide;
- 5-(3-fluorophenyl)-N-(2-methylamino-2-oxoethyl)-3-hydroxypyridin-2-yl amide; and
- 5-(3-fluorophenyl)-N-(2-dimethylamino-2-oxoethyl)-3-hydroxypyridin-2-yl amide.

\* \* \* \* \*